(12) United States Patent
Wong et al.

(10) Patent No.: US 10,183,956 B2
(45) Date of Patent: Jan. 22, 2019

(54) LANTHANIDE TOOLBOX FOR ORGANELLE SPECIFIC MOLECULAR IMAGING

(71) Applicant: New Life Medicine Technology Company Limited, Hong Kong (HK)

(72) Inventors: Ka Leung Wong, Hong Kong (HK); Hongguang Li, Hong Kong (HK); Chi Fai Chan, Hong Kong (HK); Rongfeng Lan, Hong Kong (HK)

(73) Assignee: New Life Medicine Technology Company Limited, Hong Kong (HK)

( * ) Notice: Subject to any disclaimer, the term of this patent is extended or adjusted under 35 U.S.C. 154(b) by 2 days.

(21) Appl. No.: 15/604,660

(22) Filed: May 25, 2017

(65) Prior Publication Data
US 2017/0342090 A1 Nov. 30, 2017

Related U.S. Application Data

(60) Provisional application No. 62/342,603, filed on May 27, 2016.

(51) Int. Cl.
| | |
|---|---|
| *C12Q 1/527* | (2006.01) |
| *G01N 21/00* | (2006.01) |
| *C07F 5/00* | (2006.01) |
| *G01N 33/50* | (2006.01) |
| *G01N 33/58* | (2006.01) |
| *A61K 47/48* | (2006.01) |

(52) U.S. Cl.
CPC ........ *C07F 5/003* (2013.01); *A61K 47/48076* (2013.01); *C12Q 1/527* (2013.01); *G01N 33/5076* (2013.01); *G01N 33/582* (2013.01); *G01N 2333/988* (2013.01); *G01N 2458/40* (2013.01)

(58) Field of Classification Search
CPC combination set(s) only.
See application file for complete search history.

(56) References Cited

U.S. PATENT DOCUMENTS

2018/0078564 A1* 3/2018 Wong .................. A61K 31/555

OTHER PUBLICATIONS

Li et al. "Real-time in situ monitoring via europium emission of the photo-release of antitumor cisplatin from a Eu—Pt complex" Chem . Commun. 2015, 51, 14022-14025. (Year: 2015).*
Dai et al. "New Class of Bright and Highly Stable Chiral Cyclen Europium Complexes for Circularly Polarized Luminescence Applications" Inorg. Chem. 2016, 55, 9065-9070. (Year: 2016).*
Li et al. "Real Time Detection of Cell Cycle Regulator Cyclin A on Living Tumor Cells with Europium Emission" Dalton Trans. 2013, 42, 13495. (Year: 2013).*
L. Huang et. al., "Cilia and Polycystic Kidney Disease, Kith and Kin", Birth Defects Res. C Embryo Today, (2014), 102, 174-185, p. 1-19.
U. R. Anoop, et. al., "Primary Cilia in the Pathogenesis of Dentigerous Cyst: a New Hypothesis Based on Role of Primary Cilia in Autosomal Dominant Polycystic Kidney Disease", Oral Surg. Oral Med. Oral Pathol. Oral Radiol. Endod., (2011), 111, p. 608-617.
S. G. Basten, et. al., "Functional Aspects of Primary Cilia in Signaling, Cell Cycle and Tumorigenesis", Cilia, (2013), 2, 6, p. 1-23.
V. Singla et. al., "The Primary Cilium as the Cell's Antenna: Signaling at a Sensory Organelle", Science, (2006), 313, p. 629-633.
K. Nobutani, et. al., "Absence of Primary Cilia in Cell Cycle-Arrested Human Breast Cancer Cells", Genes Cells, (2014), 19, p. 141-152.
I. R. Veland, et. al., "Primary Cilia and Signaling Pathways in Mammalian Development, Health and Disease", Nephron Physiology, (2009), 111, p. 39-53.
W. Zhang, et. al., "Real-Time Monitoring of the Mitophagy Process by a Photostable Fluorescent Mitochondrion-Specific Bioprobe with AIE Characteristics", Chem. Commun., (2015), 51, p. 9022-9025.
J. X. Zhang, et. al., "A Potential Water-Soluble Ytterbium-Based Porphyrin-Cyclen Dual Bio-Probe for Golgi Apparatus Imaging and Photodynamic Therapy", Chem. Commun. (2012), 48, p. 9646-9648.
D. G. Smith, et. al., "Live Cell imaging of Lysosomal pH Changes with pH Responsive Ratiometric Lanthanide Probes", Chem. Commun., (2012), 48, p. 8520-8522.
C. Ott, et. al., "Visualization of Live Primary Cilia Dynamics Using Fluorescence Microscopy", Curr. Protoc. Cell Biol., (2012), Chapter 4:Unit 4.26. doi: 10.1002/0471143030.cb0426s57, p. 1-24.
E. S. Swenson, et. al., "Limitations of Green Fluorescent Protein as a Cell Lineage Marker", Stem Cells, (2007), 25, p. 2593-2600.
B. N. Giepmans, et. al., "The Fluorescent Toolbox for Assessing Protein Location and Function", Science, (2006), 312, p. 217-224.
K. Hanaoka, et. al., "Time-Resolved Long-Lived Luminescence Imaging Method Employing Luminescent Lanthanide Probes with a New Microscopy System", J. Am. Chem. Soc., (2007), 129, p. 13502-13509.
Z. H. Liang, et. al., "The Effects of the Increasing Number of the Same Chromophore on Photosensitization of Water-Soluble Cyclen-Based Europium Complexes with Potential for Biological Applications", RSC Adv.5, (2015), p. 13347-13356.
M. Delling, et. al., "Primary Cilia are Specialized Calcium Signalling Organelles", Nature, (2013), 504, 311-314, p. 1-12.

(Continued)

*Primary Examiner* — Amanda L Aguirre
(74) *Attorney, Agent, or Firm* — Spruson & Ferguson (Hong Kong) Limited

(57) ABSTRACT

The present invention relates to a water-soluble, simple, stable tris(N-(tert-butyl)acetamide) cyclen-based europium complex HGEu001 which exhibits the specific subcellular localization in the primary cilium with a quantum yield as high as 10% in water and a lifetime of 0.56 ms lifetime. In particular, the present invention provides simplicity of the design and synthesis of a complex. Comprehensive studies were performed in numerous cell lines, such as HeLa, SN-K-SH and MRC5; the motif structure, HGEu002, has also been synthesized as the negative control for in vitro imaging studies. The two photon in vitro imaging were done in three dimensions to emphasize on the specific localization in primary cilium of HGEu001. This is one of the very limited examples for direct primary cilium imaging.

13 Claims, 76 Drawing Sheets

(56) References Cited

OTHER PUBLICATIONS

C. E. Larkins, et. al., "Arl13b Regulates Ciliogenesis and the Dynamic Localization of Shh Signaling Proteins", Cell, (2011), 22, p. 4694-4703.

D. C. Barral, et. al., "Arl13b Regulates Endocytic Recycling Traffic", Proc. Natl. Acad. Sci. USA, (2012), 109, p. 21354-21359.

B. Delaval, et. al., "The Cilia Protein IFT88 is Required for Spindle Orientation in Mitosis", Nature Cell Biology, (2011), 13, 461-468, p. 1-21.

M. He, et. al., "The Kinesin-4 Protein KIF7 Regulates Mammalian Hedgehog Signaling by Organizing the Cilia Tip Compartment", Nature Cell Biology, (2014), 16, 663-672, p. 1-21.

A. Beeby, et. al., "Non-Radiative Deactivation of the Excited States of Europium, Terbium and Ytterbium Complexes by Proximate Energy-matched OH, NH and CH oscillators: an Improved Luminescence Method for Establishing Solution Hydration States", J. Chem. Soc., Perkin Trans., (1999), 2, p. 493-503.

A. Aebischer, et. al., "Intrinsic Quantum Yields and Radiative Lifetimes of Lanthanide Tris (Dipicolinates)", Physical Chemistry Chemical Physics, (2009), 11, p. 1346-1353.

Y.W. Yip, et. al., "Increased Antenna Effect of the Lanthanide Complexes by Control of a Number of Terdentate N-Donor Pyridine Ligands", Inorganic Chemistry, (2012), 51, p. 7013-7015.

J. C. Bunzli, "Lanthanide Luminescence for Biomedical Analyses and Imaging", Chemical Reviews, (2010), 110, p. 2729-2755.

H. Li, et. al., "Real-Time in Situ Monitoring Via Europium Emission of the Photo- Release of Antitumor Cisplatin from a Eu-Pt Complex", Chemical Communications, (2015), 51, p. 14022-14025.

R. Katoono, et. al., "Chiroptical Molecular Propellers Based on Hexakis (phenylethynyl) Benzene through the Complexation-Induced Intramolecular Transmission of Local Point Chirality", Organic and Biomolecular Chemistry, (2014), 12, p. 9532-9538.

T. Mani, et. al., "Effect of the Regiochemistry of Butyl Amide Substituents on the Solution-State Structures of Lanthanide(III) DOTA-Tetraamide Complexes", Inorganic Chemistry, (2009), 48, p. 10338-10345.

M. H. V. Werts, et. al., "The Emission Spectrum and the Radiative Lifetime of Eu 3+ in Luminescent Lanthanide Complexes", Phys. Chem. Chem. Phys. (2002), 4, p. 1542-1548.

International Search Report of PCT/CN2017/086101 dated Aug. 18, 2017.

* cited by examiner

LANTHANIDE TOOLBOX FOR ORGANELLE SPECIFIC MOLECULAR IMAGING

CROSS-REFERENCE TO RELATED APPLICATIONS

This application claims priority from and the benefit of U.S. Provisional Patent Application Ser. No. 62/342,603 filed on May 27, 2016, the disclosure of which is hereby incorporated by reference in its entirety.

FIELD OF INVENTION

The present invention relates to a serious of water-soluble, simple, stable cyclen-based lanthanide complex HGEu001 and the derivatives thereof. In particular, the present invention provides simplicity of the design and synthesis of a tris(N-(tert-butyl)acetamide) cyclen-based europium complex HGEu001 which exhibits the specific subcellular localization in the primary cilium with a quantum yield as high as 10% in water and a lifetime of 0.56 ms lifetime. The present invention has applications in organelle specific imaging.

BACKGROUND OF INVENTION

The primary cilium is a solitary, non-motile microtubule-based organelle that protrudes outwards from the surface of most normal eukaryotic cells. Upon in-depth investigation, it has been found to participate actively in various intercellular signaling pathways in mammals, e.g. Hedgehog (Hh), Wingless (Wnt) and PDGFRa, for cell migration, homeostasis, and cell cycle regulation. It also functions as the multisensory antenna of the cells towards external stimuli, such as chemical, temperature, and pressure stimuli.

Recently, a renaissance on the research of its structure was initiated by substantial new and overwhelming evidence in support of its significant correlation with many human diseases and developmental disorders (collectively known as ciliopathies). For instance, dysfunctions of primary cilium signaling have been found to correlate strongly in human polycystic kidney diseases, epithelial ovarian cancer, as well as aberrant skeletal development; the absence of primary cilia and overexpression of proteins nearby have also well been observed throughout the stages of pancreatic, breast, and prostate tumorigenesis.

That said, very little have the roles of primary cilium been clearly and fully known so far, with the lack of direct and specific imaging methods, for example visible-to-near-infrared fluorescence imaging and magnetic resonance imaging, being a critical factor. There are so many organelle-specific markers currently available for mitochondria, Golgi apparatus, and lysosome; however, visualization of primary cilia, to date, can only be achieved through immunostaining using antibodies or green fluorescent proteins, as no primary cilium-specific probes have been reported in literature. Such two indirect means are always challenged with fixation and delivery issues, while auto-fluorescence is inevitable and the amount of information obtained through them is limited.

To address all the above problems, using a direct and specific imaging tool incorporated with lanthanide ions is a promising solution. The long emission lifetimes (micro to millisecond region), hypersensitive, sharp and fingerprint spectral profile of europium, paired with a time-gated system, can effectively eliminate the interfering autofluorescence as well as allowing the specific imaging of primary cilium in a time-resolved manner in vitro or in vivo.

Therefore, it turns out to be a need for simplicity of the design and synthesis of a complex which exhibits the specific subcellular localization in the primary cilium.

Citation or identification of any reference in this section or any other section of this application shall not be construed as an admission that such reference is available as prior art for the present application.

SUMMARY OF INVENTION

Accordingly, the first objective of the presently claimed invention relates to a water-soluble, simple, stable tris(N-(tert-butyl)acetamide) cyclen-based europium complex HGEu001 which exhibits the specific subcellular localization in the primary cilium with a quantum yield as high as 10% in water and a lifetime of 0.56 ms lifetime. In particular, the present invention provides simplicity of the design and synthesis of a complex HGEu001 that is the very salient point of one embodiment of the present invention. Comprehensive studies were performed in numerous cell lines, such as HeLa, SN-K-SH and MRC5; the motif structure, HGEu002, has also been synthesized as the negative control for in vitro imaging studies. The two photons in vitro imaging were done in three dimensions to emphasize on the specific localization in primary cilium of HGEu001. This is one of the very limited examples for direct primary cilium imaging.

In a first aspect of the present invention there is provided a compound for imaging rod-like organelle in biological cells comprising a molecule of formula (I):

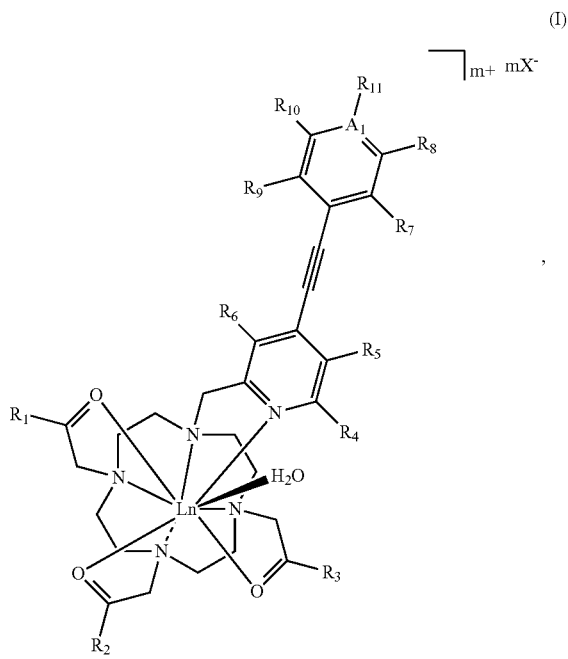

wherein Ln is selected from Eu, Tb, Gd, Yb, Er, Dy, Sm, La, Ce, Pr, Nd, Pm, Tm and Y; $X^-$ is selected from $Cl^-$, $NO_3^-$, $CH_3COO^-$, $ClO_4^-$ or other anions; $A_1$ is selected from C, N or Si; $R_1$, $R_2$ and $R_3$ are jointly or separately selected from NH(tert)Bu, $OH^-$ or other amine; $R_4$, $R_5$, $R_6$, $R_7$, $R_8$, $R_9$ and $R_{10}$ are jointly or separately selected from H, $CF_3$, OMe, OEt, OH or $NMe_2$; $R_{11}$ is selected from alkyl, aryl ether, ester, amide or aromatic rings; m is an integer selected from 0, 1, 2 or 3. More specifically, the derivatives of the molecule of the formula (I) is shown in formula (II):

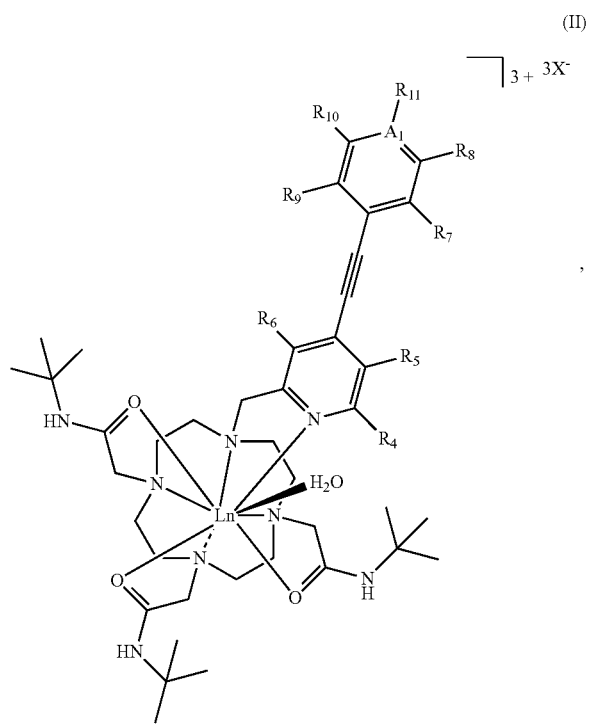

wherein $R_{11}$ is selected from:

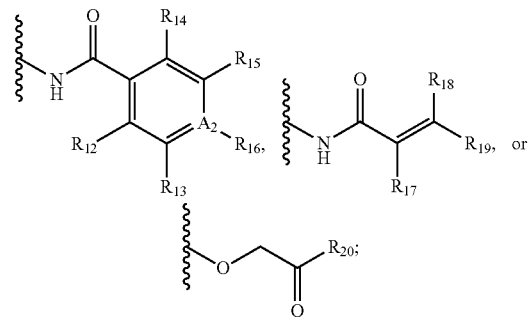

and
wherein $R_{12}$, $R_{13}$, $R_{14}$, $R_{15}$, $R_{16}$, $R_{17}$, $R_{18}$, $R_{19}$, and $R_{20}$ are jointly or separately selected from H, $CF_3$, OMe, OEt, OH or $NMe_2$; $A_2$ is selected from C, N, or Si. Alternatively, the corresponding substituents for X, $A_2$ and $R_n$ (where n=4-20) in each of the derivatives are defined as follows:
HGL001: X=Cl, $A_2$=C, $R_n$=H (n=4-10, 12-16);
HGL002: X=Cl, $A_2$=C, $R_n$=H (n=4-10, 12-15), $R_{16}$=$CF_3$;
HGL003: X=Cl, $A_2$=C, $R_n$=H (n=4-10, 12-15), $R_{16}$=OMe;
HGL004: X=Cl, $A_2$=C, $R_n$=H (n=4-10, 12-15), $R_{16}$=$NMe_2$;
HGL005: X=Cl, $A_2$=N, $R_n$=H (n=4-10, 12-15);
HGL006: X=Cl, $R_n$=H (n=4-10, 17-19);
HGL007: X=Cl, $R_n$=H (n=4-10), $R_{20}$=OH;
HGL008: X=Cl, $R_n$=H (n=4-10), $R_{20}$=OEt;
HGL009: X=Cl, $A_2$=C, $R_n$=H (n=4-6, 8, 10, 12-16), $R_7$=$R_9$=OMe;
HGL010: X=Cl, $A_2$=C, $R_n$=H (n=4-6, 8, 10, 12-15), $R_7$=$R_9$=OMe, $R_{16}$=$CF_3$;
HGL011: X=Cl, $A_2$=C, $R_n$=H (n=4-6, 8, 10, 12-15), $R_7$=$R_9$=$R_{16}$=OMe;
HGL012: X=Cl, $A_2$=C, $R_n$=H (n=4-6, 8, 10, 12-15), $R_7$=$R_9$=OMe, $R_{16}$=$NMe_2$;
HGL013: X=Cl, $A_2$=N, $R_n$=H (n=4-6, 8, 10, 12-15), $R_7$=$R_9$=OMe;
HGL014: X=Cl, $A_2$=C, $R_n$=H (n=4-6, 8, 10, 17-19), $R_7$=$R_9$=OMe;
HGL015: X=Cl, $A_2$=C, $R_n$=H (n=4-6, 8, 10), $R_7$=$R_9$=OMe, $R_{20}$=OH;
HGL016: X=Cl, $A_2$=C, $R_n$=H (n=4-6, 8, 10), $R_7$=$R_9$=OMe, $R_{20}$=OEt;
where Ln refers to lanthanide; OMe refers to a methoxy group; $NMe_2$ refers to a nitro-dimethyl group; OEt refers to ethoxy group.

In a first embodiment of the first aspect of the present invention there is provided a compound for imaging rod-like organelle in biological cells comprising a molecule of the formula (I) or (II) wherein the rod-like organelle in biological cells is primary cilium.

In a second embodiment of the first aspect of the present invention there is provided a compound for imaging rod-like organelle in biological cells comprising a molecule of the formula (I) or (II) wherein the imaging is done in living cells.

In a third embodiment of the first aspect of the present invention there is provided a compound for imaging rod-like organelle in biological cells comprising a molecule of the formula (I) or (II) wherein the imaging is performed using a linear fluorescence microscopy under UV light excitation or a two-photon confocal laser scanning microscope.

In a fourth embodiment of the first aspect of the present invention there is provided a compound for imaging rod-like organelle in biological cells comprising a molecule of the formula (I) wherein the molecule comprising a compound of HGEu001. HGEu001 can also be represented by formula (III):

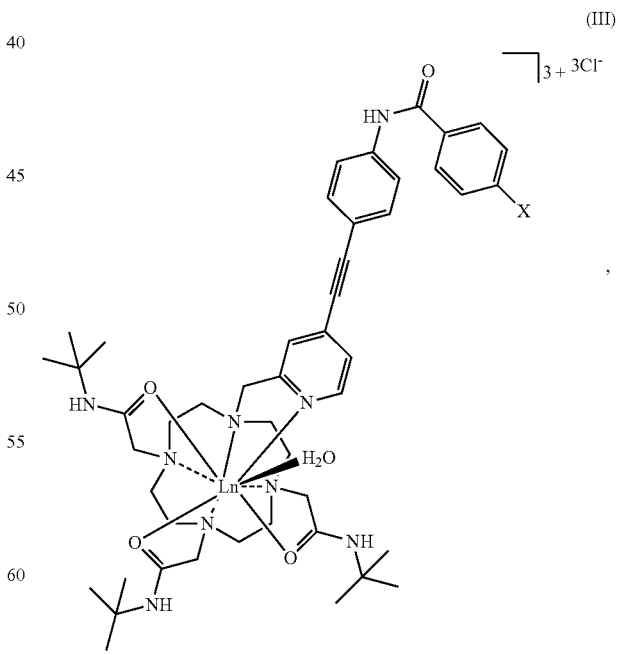

wherein X is H; Ln is Eu.

In a fifth embodiment of the first aspect of the present invention there is provided a compound for imaging rod-like organelle in biological cells comprising a molecule of the formula (I), (II) or (III) can selectively bind to proteins in cells.

In a sixth embodiment of the first aspect of the present invention there is provided a compound for imaging rod-like organelle in biological cells comprising a molecule of the formula (I), (II) or (III) can be primary cilium related proteins.

In a seventh embodiment of the first aspect of the present invention there is provided a compound for imaging rod-like organelle in biological cells comprising a molecule of the formula (I), (II), or (III) being used for quantitative analysis of primary cilium related proteins.

In an eighth embodiment of the first aspect of the present invention there is provided a compound for imaging rod-like organelle in biological cells comprising a molecule of the formula (I), (II) or (III) being used as a disease diagnosis probes.

In a ninth embodiment of the first aspect of the present invention there is provided a compound for imaging rod-like organelle in biological cells comprising a molecule of the formula (I), (II) or (III) being used as an organelle targeting specific vector.

In a tenth embodiment of the first aspect of the present invention there is provided a compound for imaging rod-like organelle in biological cells comprising a molecule of the formula (I), (II) or (III) being conjugated with drugs for combined disease treatment.

In a eleventh embodiment of the first aspect of the present invention, said using of the molecule of formula (I), (II) or (III) comprises dissolving said compound in an aqueous solution before accumulating in the rod-like organelle in biological cells for said imaging.

In a second aspect of the present invention there is provided a method for imaging rod-like organelle in biological cells comprising accumulating the compound of formula (I), (II) or (III) in the rod-like organelle in biological cells directly.

In a first embodiment of the second aspect of the present invention there is provided a method for imaging rod-like organelle in biological cells wherein the rod-like organelle in biological cells is primary cilium.

In a second embodiment of the second aspect of the present invention there is provided a method for imaging rod-like organelle in biological cells comprising accumulating the compound of formula (I), (II) or (III) wherein the imaging is performed using a linear fluorescence microscopy under UV light excitation or a two-photon confocal laser scanning microscope.

In a third embodiment of the second aspect of the present invention there is provided a method for imaging rod-like organelle in biological cells comprising accumulating the compound of formula (I), (II) or (III) wherein the imaging is done in living cells.

In a third aspect of the present invention there is provided a method for quantitatively analyzing primary cilium related proteins comprising accumulating the compound of formula (I), (II) or (III) in the rod-like organelle in biological cells directly.

In a fourth aspect of the present invention there is provided a method for diagnosing primary cilium related disease comprising using the compound of formula (I), (II) or (III) as a disease diagnosis probe.

In a fifth aspect of the present invention there is provided a method for targeting primary cilium in biological cells comprising using the compound of formula (I), (II) or (III) as an organelle targeting specific vector or agent.

In a sixth aspect of the present invention there is provided a method for treating primary cilium related disease comprising administering a compound of formula (I), (II) or (III) in conjugation with drugs for combined treatment.

Throughout this specification, unless the context requires otherwise, the word "include" or "comprise" or variations such as "includes" or "comprises" or "comprising", will be understood to imply the inclusion of a stated integer or group of integers but not the exclusion of any other integer or group of integers. It is also noted that in this disclosure and particularly in the claims and/or paragraphs, terms such as "included", "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the present invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the present invention and apply throughout. Unless otherwise defined, all other technical terms used herein have the same meaning as commonly understood to one of ordinary skill in the art to which the present invention belongs.

Other aspects and advantages of the present invention will be apparent to those skilled in the art from a review of the ensuing description.

BRIEF DESCRIPTION OF DRAWINGS

The above and other objects and features of the present invention will become apparent from the following description of the present invention, when taken in conjunction with the accompanying drawings, in which:

FIG. 2I shows Linear fluorescence microscopy merged images for FIGS. 2C and 2F.

FIG. 6B shows the three dimensional (by z stack) two-photon confocal in vitro images of HGEu002 (negative control) with co-localization of green GFP-ARL14B/GFP-IFT88/MitoTracker® Green FM (M-7514) in HeLa cells. ($\lambda_{ex}$=700 nm) HeLa cells were first transfected with GFP-ARL13B/GFP-IFT88 or incubated with MitoTracker® Green FM (M-7514) for 15 minutes and further incubated 6 hours with 10 μM of HGEu002.

DETAILED DESCRIPTION OF THE INVENTION

Figure 1A:
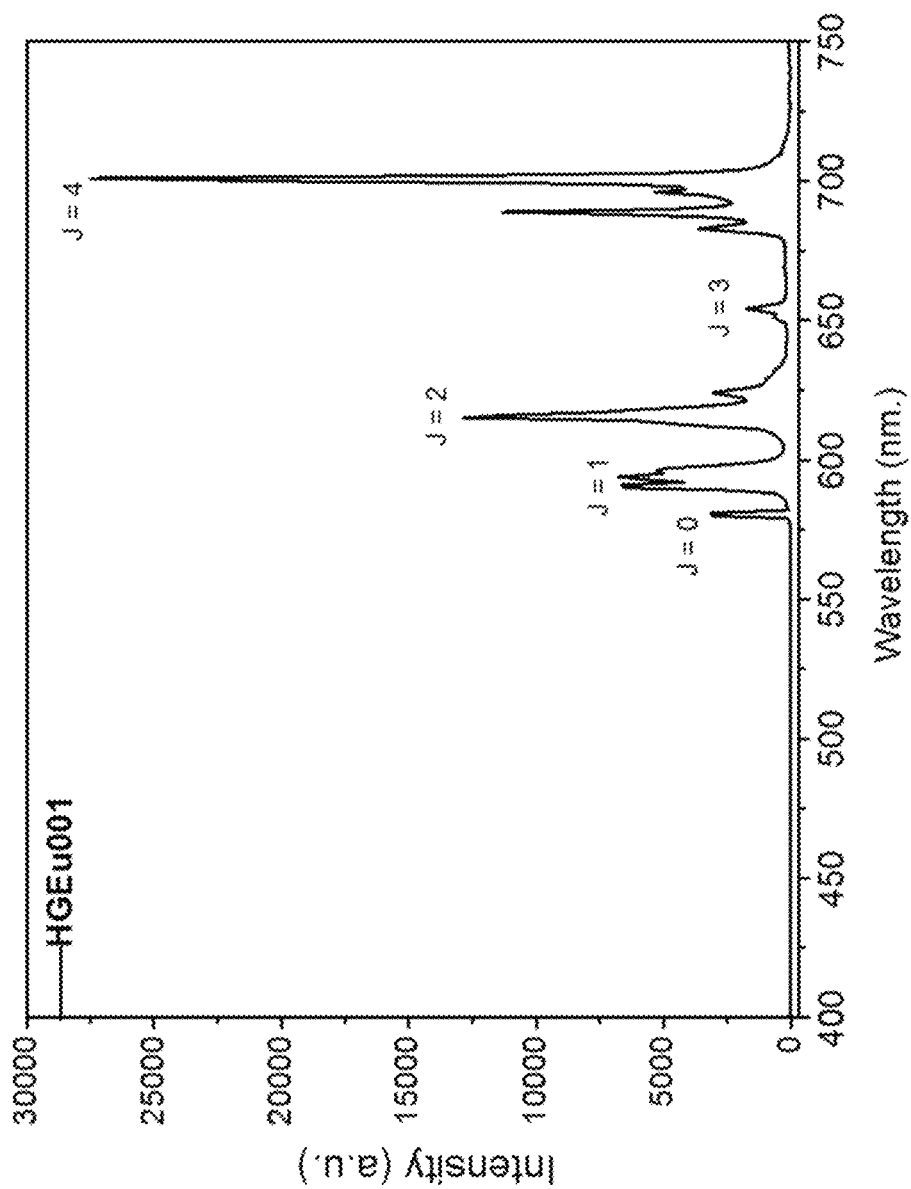
FIG. 1A shows the chemical structures and emission spectra of HGEu001 in aqueous solution (10 μM and $\lambda_{ex}$=340 nm).
Figure 1B:
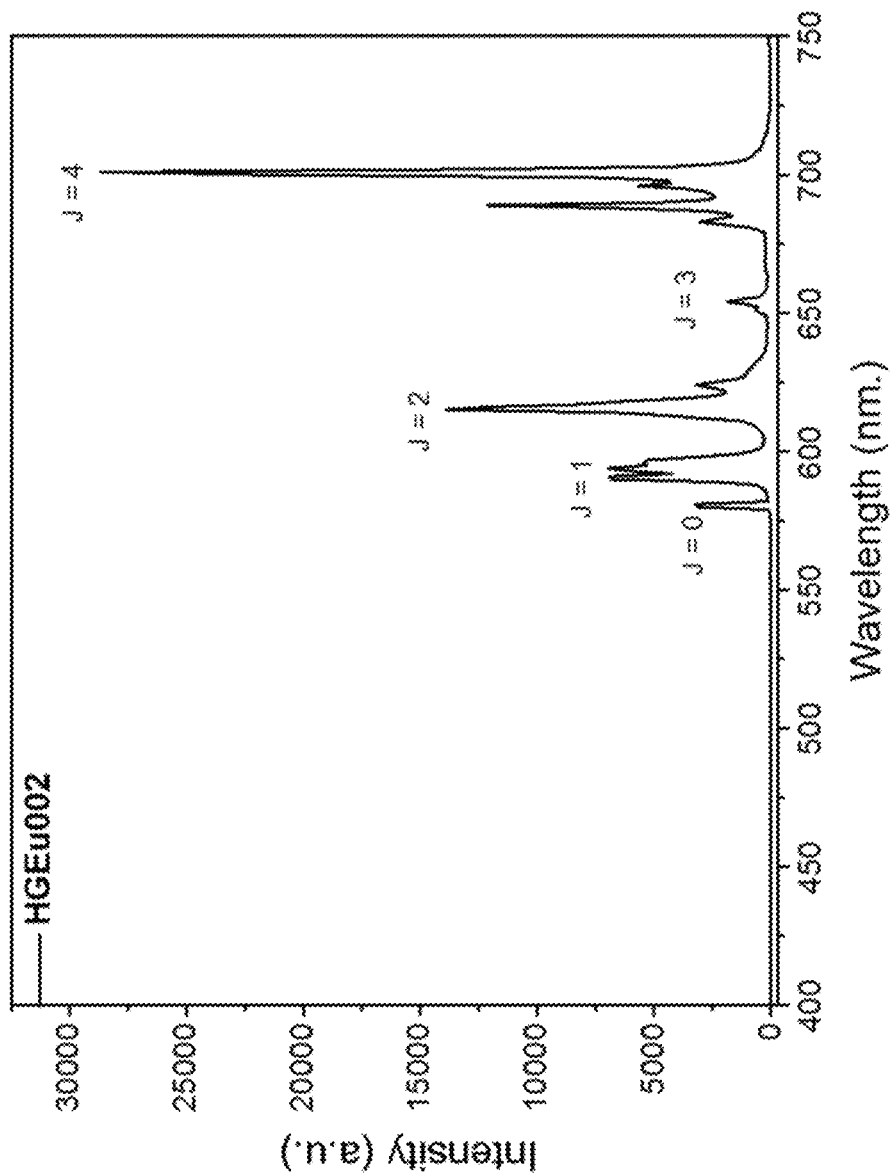
FIG. 1B shows the chemical structures and emission spectra of HGEu002 in aqueous solution (10 μM and $\lambda_{ex}$=340 nm).
Figure 2A:
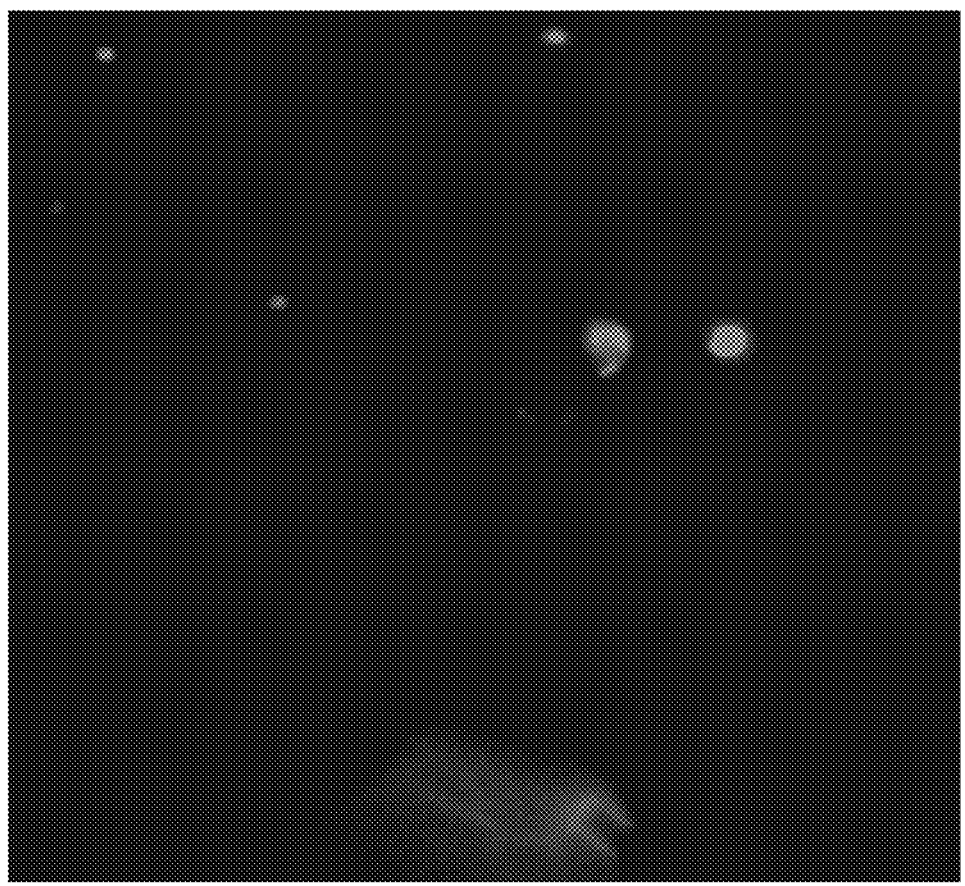
FIG. 2A shows Linear fluorescence microscopy images of the red emission from HGEu001 (dosage concentration=10 μM, $\lambda_{ex}$=375 nm, band pass=610-630 nm) after 6 hours exposure in HeLa cells.
Figure 2B:
FIG. 2B shows Linear fluorescence microscopy images of the red emission from HGEu001 (dosage concentration=10 μM, $\lambda_{ex}$=375 nm, band pass=610-630 nm) after 6 hours exposure in HeLa cells.
Figure 2C:
FIG. 2C shows Linear fluorescence microscopy images of the red emission from HGEu001 (dosage concentration=10 μM, $\lambda_{ex}$=375 nm, band pass=610-630 nm) after 6 hours exposure in HeLa cells.
Figure 2D:
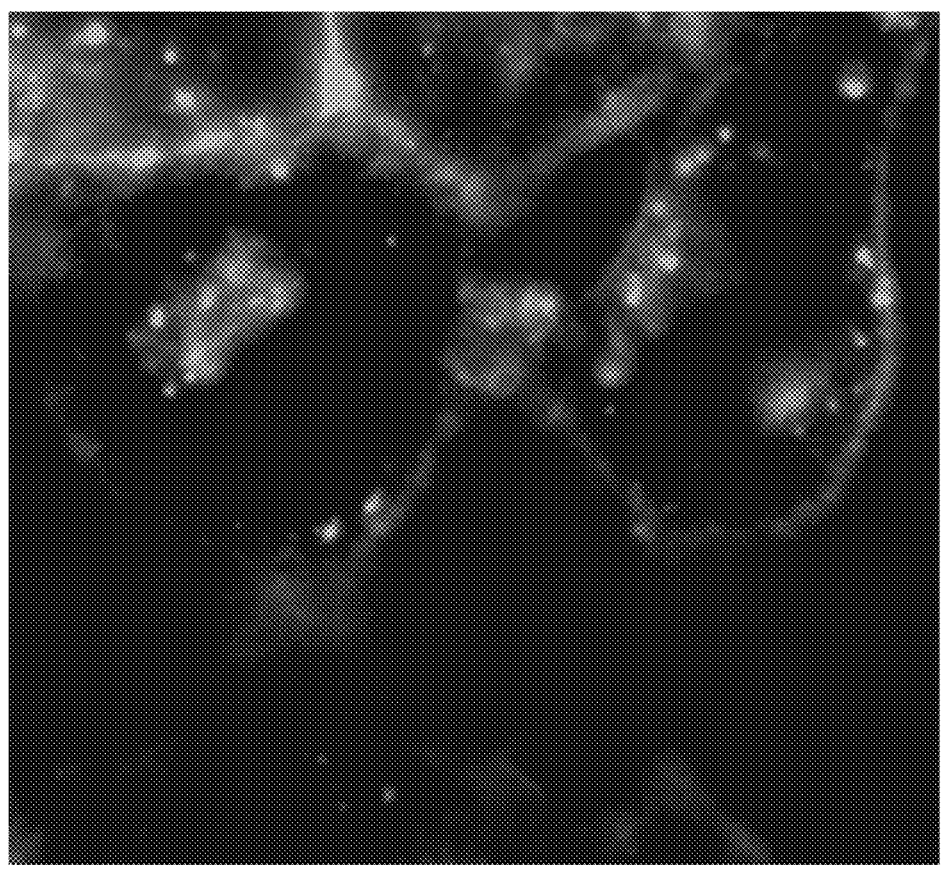
FIG. 2D shows Linear fluorescence microscopy images of the GolgiTracker® Oregon Green (W6748, Wheat Germ Agglutinin) dosed in HeLa cells (50 nM, $\lambda_{ex}$=488 nm, band pass=505-555 nm.
Figure 2E:
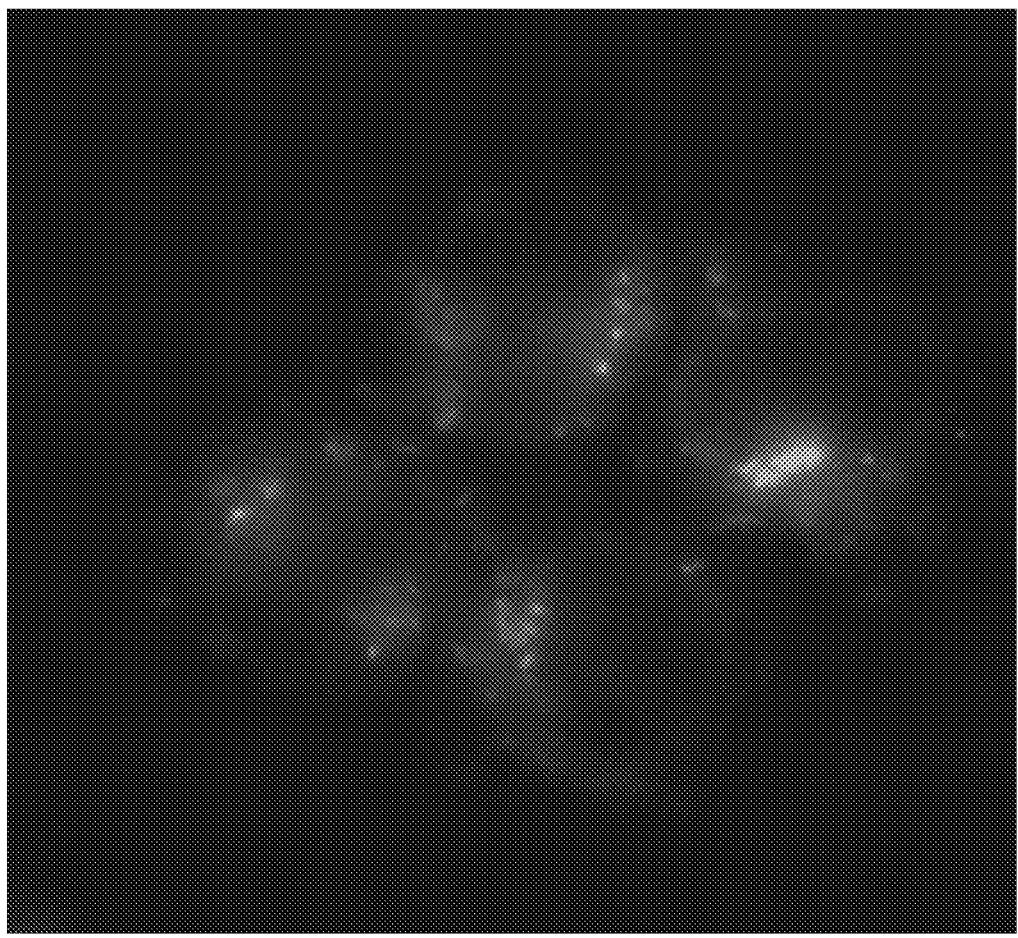
FIG. 2E shows Linear fluorescence microscopy images of the LysoTracker® Green DND-26 (L-7526) dosed in HeLa cells (50 nM, $\lambda_{ex}$=488 nm, band pass=505-555 nm).
Figure 2F:
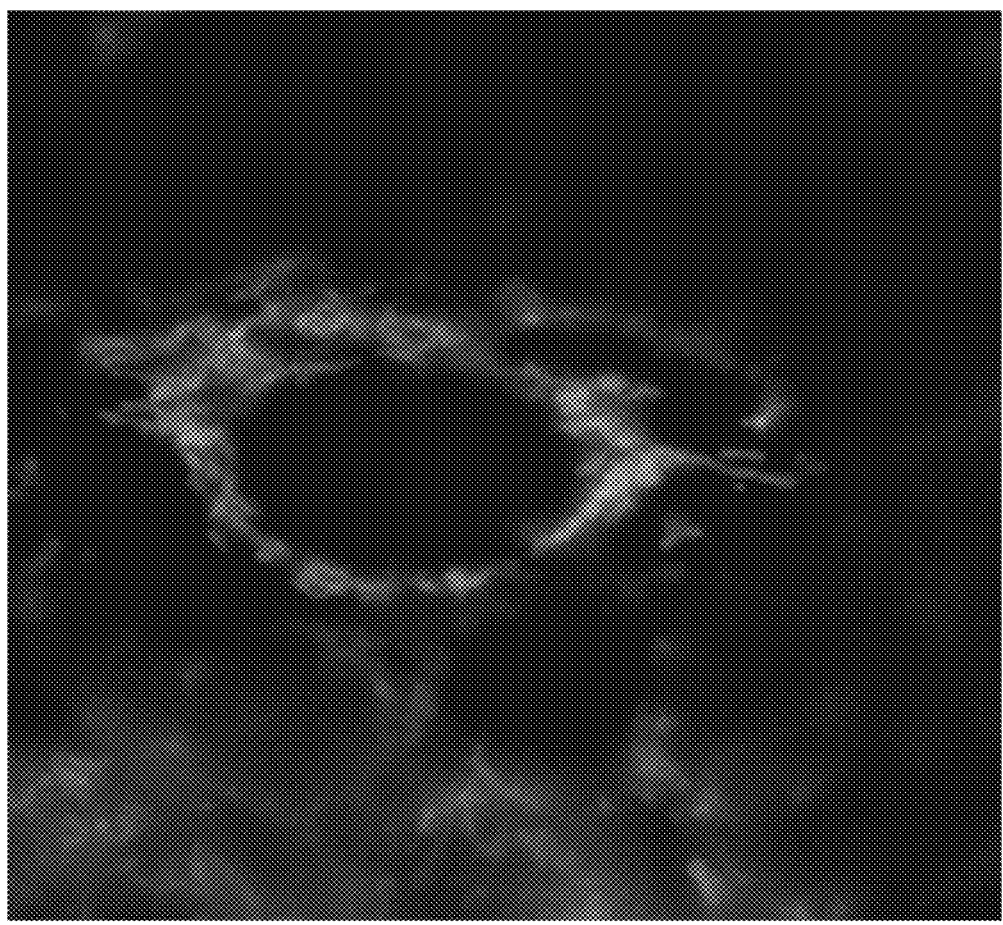
FIG. 2F shows Linear fluorescence microscopy images of the MitoTracker® Green FM (M-7514) dosed in HeLa cells (50 nM, $\lambda_{ex}$=488 nm, band pass=505-555 nm).
Figure 2G:
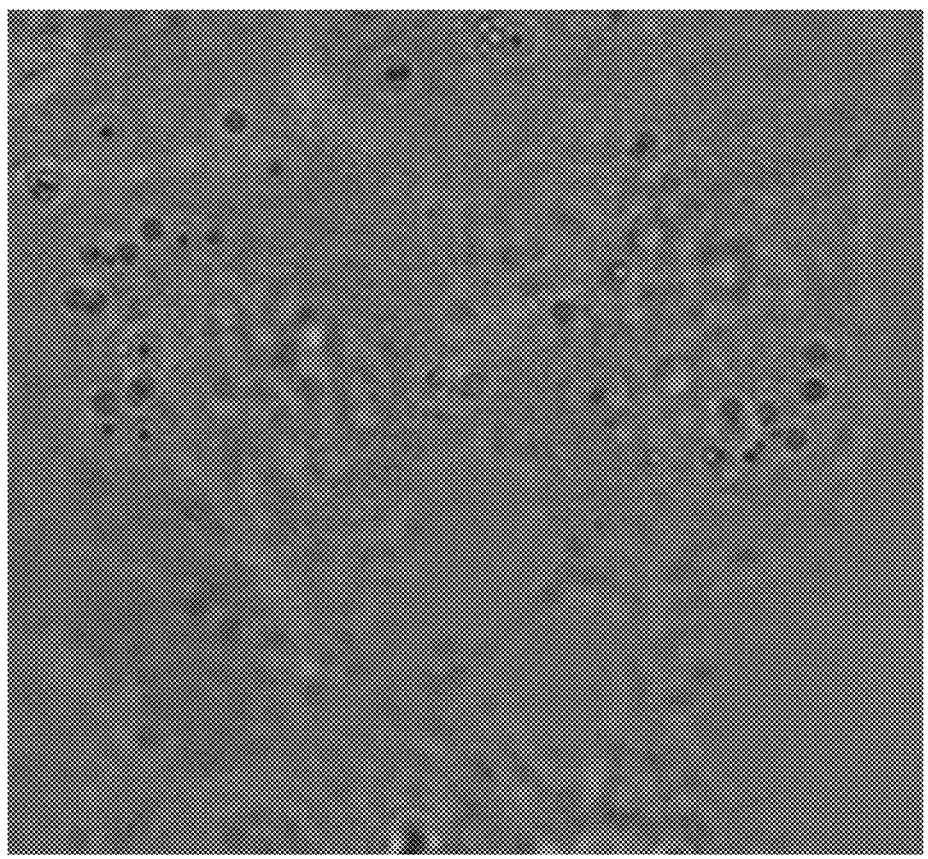
FIG. 2G shows Linear fluorescence microscopy merged images for FIGS. 2A and 2D.
Figure 2H:
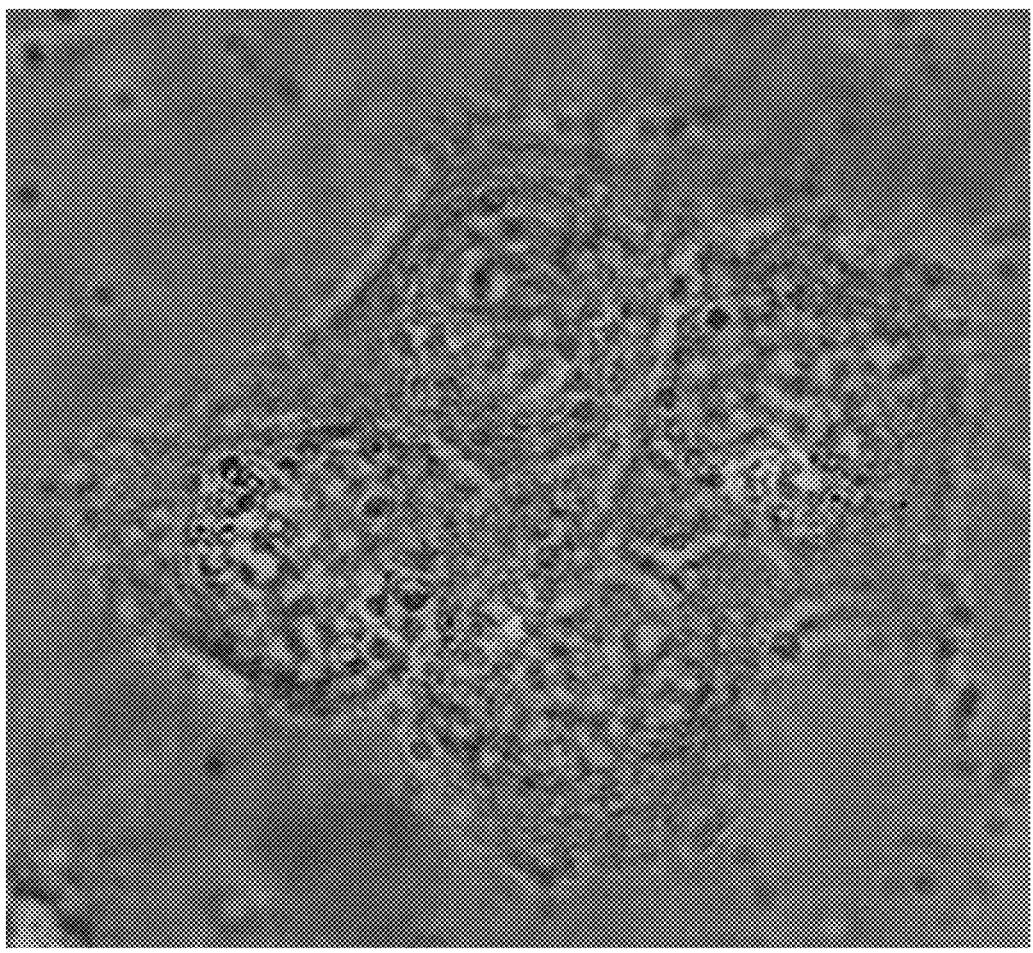
FIG. 2H shows Linear fluorescence microscopy merged images for FIGS. 2B and 2E.

The first objective of the presently claimed invention relates to a water-soluble, simple, stable tris(N-(tert-butyl) acetamide) cyclen-based europium complex HGEu001 which exhibits the specific subcellular localization in the primary cilium with a quantum yield as high as 10% in water and a lifetime of 0.56 ms lifetime. In particular, the present invention provides simplicity of the design and synthesis of a complex HGEu001 that is the very salient point of one embodiment of the present invention. Comprehensive studies were performed in numerous cell lines, such as HeLa, SN—K—SH and MRC5; the motif structure, HGEu002, has also been synthesized as the negative control for in vitro imaging studies. The two photons in vitro imaging were done in three dimensions to emphasize on the specific localization in primary cilium of HGEu001. This is one of the very limited examples for direct primary cilium imaging.

In a first aspect of the present invention there is provided a compound for imaging rod-like organelle in biological cells comprising a molecule of formula (I):

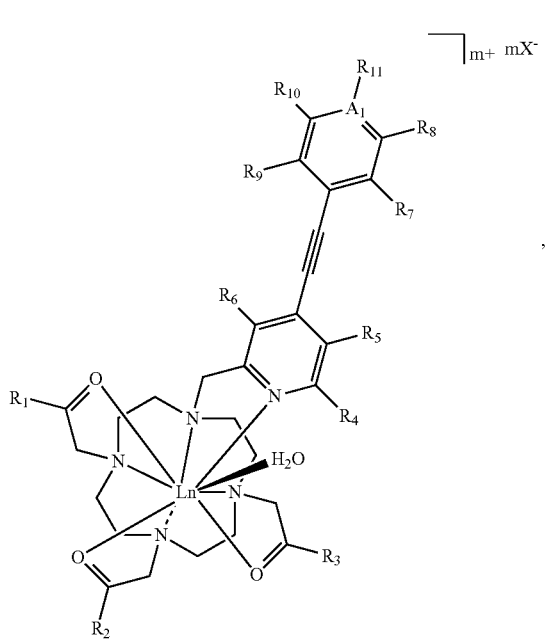

(I)

wherein Ln is selected from Eu, Tb, Gd, Yb, Er, Dy, Sm, La, Ce, Pr, Nd, Pm, Tm and Y, $X^-$ is selected from $Cl^-$, $NO_3^-$, $CH_3COO^-$, $ClO_4^-$ or other anions; $A_1$ is selected from C, N or Si; $R_1$, $R_2$ and $R_3$ are jointly or separately selected from NH(tert)Bu, $OH^-$ or other amine; $R_4$, $R_5$, $R_6$, $R_7$, $R_8$, $R_9$ and $R_{10}$ are jointly or separately selected from H, $CF_3$, OMe, OEt, OH or $NMe_2$; $R_{11}$ is selected from alkyl, aryl ether, ester, amide or aromatic rings; m is an integer selected from 0, 1, 2 or 3. More specifically, the derivatives of the molecule of the formula (I) is shown in formula (II):

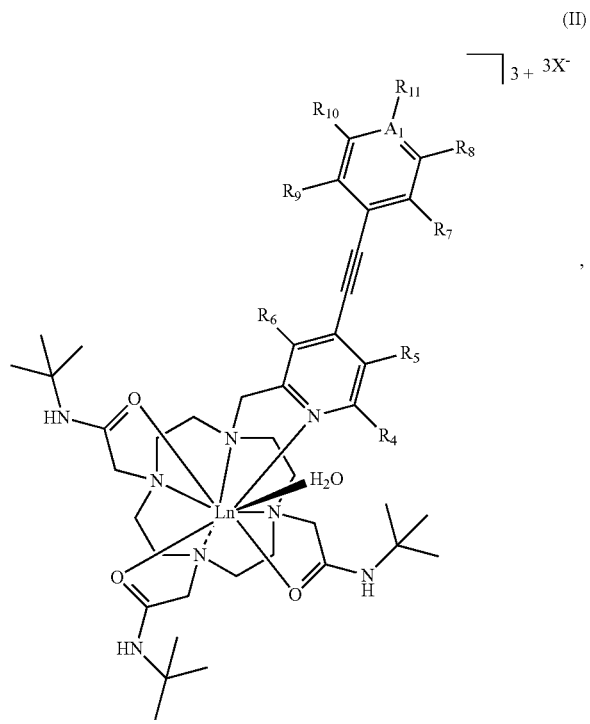

(II)

wherein $R_{11}$ is selected from:

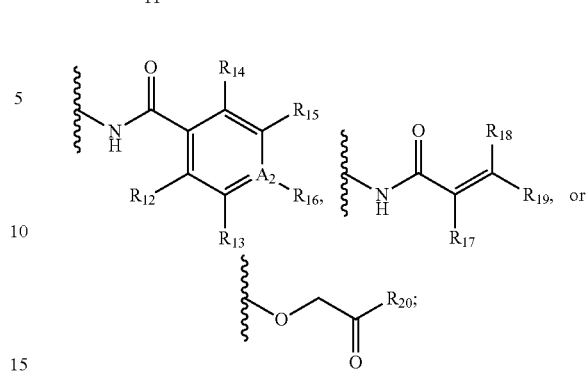

and
wherein $R_{12}$, $R_{13}$, $R_{14}$, $R_{15}$, $R_{16}$, $R_{17}$, $R_{18}$, $R_{19}$, and $R_{20}$ are jointly or separately selected from H, $CF_3$, OMe, OEt, OH or $NMe_2$; $A_2$ is selected from C, N, or Si. Alternatively, the corresponding substituents for X, $A_2$ and $R_n$ (where n=4-20) in each of the derivatives are defined as follows:
HGL001: X=Cl, $A_2$=C, $R_n$=H (n=4-10, 12-16);
HGL002: X=Cl, $A_2$=C, $R_n$=H (n=4-10, 12-15), $R_{16}$=$CF_3$;
HGL003: X=Cl, $A_2$=C, $R_n$=H (n=4-10, 12-15), $R_{16}$=OMe;
HGL004: X=Cl, $A_2$=C, $R_n$=H (n=4-10, 12-15), $R_{16}$=$NMe_2$;
HGL005: X=Cl, $A_2$=N, $R_n$=H (n=4-10, 12-15);
HGL006: X=Cl, $R_n$=H (n=4-10, 17-19);
HGL007: X=Cl, $R_n$=H (n=4-10), $R_{20}$=OH;
HGL008: X=Cl, $R_n$=H (n=4-10), $R_{20}$=OEt;
HGL009: X=Cl, $A_2$=C, $R_n$=H (n=4-6, 8, 10, 12-16), $R_7$=$R_9$=OMe;
HGL010: X=Cl, $A_2$=C, $R_n$=H (n=4-6, 8, 10, 12-15), $R_7$=$R_9$=OMe, $R_{16}$=$CF_3$;
HGL011: X=Cl, $A_2$=C, $R_n$=H (n=4-6, 8, 10, 12-15), $R_7$=$R_9$=$R_{16}$=OMe;
HGL012: X=Cl, $A_2$=C, $R_n$=H (n=4-6, 8, 10, 12-15), $R_7$=$R_9$=OMe, $R_{16}$=$NMe_2$;
HGL013: X=Cl, $A_2$=N, $R_n$=H (n=4-6, 8, 10, 12-15), $R_7$=$R_9$=OMe;
HGL014: X=Cl, $A_2$=C, $R_n$=H (n=4-6, 8, 10, 17-19), $R_7$=$R_9$=OMe;
HGL015: X=Cl, $A_2$=C, $R_n$=H (n=4-6, 8, 10), $R_7$=$R_9$=OMe, $R_{20}$=OH;
HGL016: X=Cl, $A_2$=C, $R_n$=H (n=4-6, 8, 10), $R_7$=$R_9$=OMe, $R_{20}$=OEt;
where Ln refers to lanthanide; OMe refers to a methoxy group; $NMe_2$ refers to a nitro-dimethyl group; OEt refers to ethoxy group.

In a first embodiment of the first aspect of the present invention there is provided a compound for imaging rod-like organelle in biological cells comprising a molecule of the formula (I) or (II) wherein the rod-like organelle in biological cells is primary cilium.

In a second embodiment of the first aspect of the present invention there is provided a compound for imaging rod-like organelle in biological cells comprising a molecule of the formula (I) or (II) wherein the imaging is done in living cells.

In a third embodiment of the first aspect of the present invention there is provided a compound for imaging rod-like organelle in biological cells comprising a molecule of the formula (I) or (II) wherein the imaging is performed using a linear fluorescence microscopy under UV light excitation or a two-photon confocal laser scanning microscope.

In a fourth embodiment of the first aspect of the present invention there is provided a compound for imaging rod-like organelle in biological cells comprising a molecule of the formula (I) wherein the molecule comprising a compound of HGEu001. HGEu001 can also be represented by formula (III):

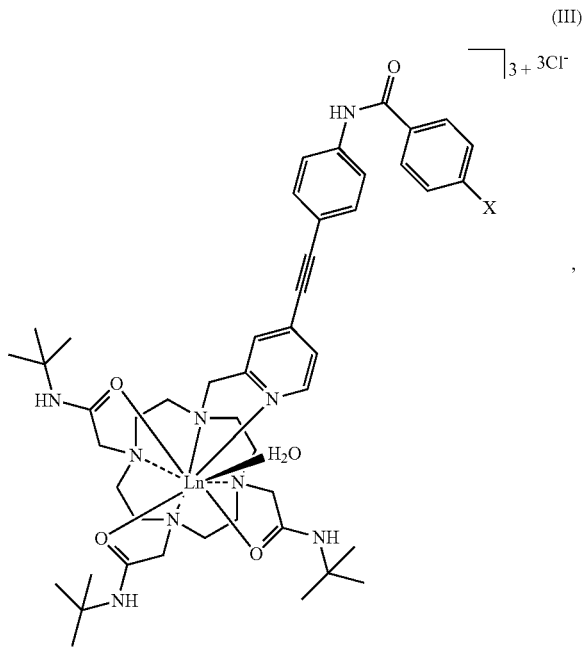

wherein X is H; Ln is Eu.

In a fifth embodiment of the first aspect of the present invention there is provided a compound for imaging rod-like organelle in biological cells comprising a molecule of the formula (I), (II) or (III) can selectively bind to proteins in cells.

In a sixth embodiment of the first aspect of the present invention there is provided a compound for imaging rod-like organelle in biological cells comprising a molecule of the formula (I), (II) or (III) can be primary cilium related proteins.

In a seventh embodiment of the first aspect of the present invention there is provided a compound for imaging rod-like organelle in biological cells comprising a molecule of the formula (I), (II), or (III) being used for quantitative analysis of primary cilium related proteins.

In an eighth embodiment of the first aspect of the present invention there is provided a compound for imaging rod-like organelle in biological cells comprising a molecule of the formula (I), (II) or (III) being used as a disease diagnosis probes.

In a ninth embodiment of the first aspect of the present invention there is provided a compound for imaging rod-like organelle in biological cells comprising a molecule of the formula (I), (II) or (III) being used as an organelle targeting specific vector.

In a tenth embodiment of the first aspect of the present invention there is provided a compound for imaging rod-like organelle in biological cells comprising a molecule of the formula (I), (II) or (III) being conjugated with drugs for combined disease treatment.

In a eleventh embodiment of the first aspect of the present invention, said using of the molecule of formula (I), (II) or (III) comprises dissolving said compound in an aqueous solution before accumulating in the rod-like organelle in biological cells for said imaging.

In a second aspect of the present invention there is provided a method for imaging rod-like organelle in biological cells comprising accumulating the compound of formula (I), (II) or (III) in the rod-like organelle in biological cells directly.

In a first embodiment of the second aspect of the present invention there is provided a method for imaging rod-like organelle in biological cells wherein the rod-like organelle in biological cells is primary cilium.

In a second embodiment of the second aspect of the present invention there is provided a method for imaging rod-like organelle in biological cells comprising accumulating the compound of formula (I), (II) or (III) wherein the imaging is performed using a linear fluorescence microscopy under UV light excitation or a two-photon confocal laser scanning microscope.

In a third embodiment of the second aspect of the present invention there is provided a method for imaging rod-like organelle in biological cells comprising accumulating the compound of formula (I), (II) or (III) wherein the imaging is done in living cells.

In a third aspect of the present invention there is provided a method for quantitatively analyzing primary cilium related proteins comprising accumulating the compound of formula (I), (II) or (III) in the rod-like organelle in biological cells directly.

In a fourth aspect of the present invention there is provided a method for diagnosing primary cilium related disease comprising using the compound of formula (I), (II) or (III) as a disease diagnosis probe.

In a fifth aspect of the present invention there is provided a method for targeting primary cilium in biological cells comprising using the compound of formula (I), (II) or (III) as an organelle targeting specific vector or agent.

In a sixth aspect of the present invention there is provided a method for treating primary cilium related disease comprising administering a compound of formula (I), (II) or (III) in conjugation with drugs for combined treatment.

The presently claimed invention is further illustrated by the following experiments or embodiments which should be understood that the subject matters disclosed in the experiments or embodiments may only be used for illustrative purpose but are not intended to limit the scope of the presently claimed invention:

Materials and Methods

Synthesis and Characterization of HGEu001 and HGEu002

General Information for the Synthesis.

Figure 29:
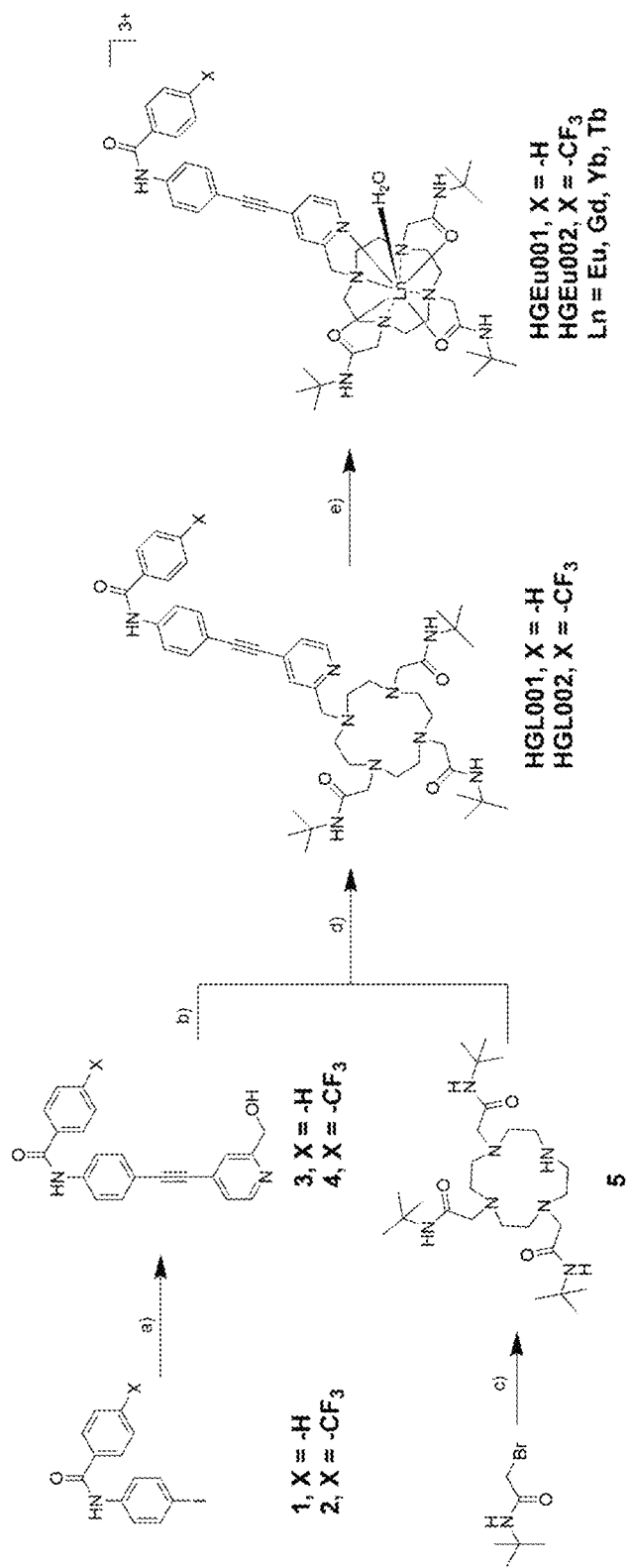
FIG. 29 shows the synthesis scheme (Scheme 1) of HGEu001 and its motif complex HGEu002: (a) (4-ethynylpyridin-2-yl)methanol, Pd(PPh$_3$)$_4$, CuI, DIPEA, THF; (b) MsCl, DIPEA, DCM; (c) cyclen, NaHCO$_3$, CH$_3$CN; (d) K$_2$CO$_3$, MeCN, 60° C.; (e) EuCl$_3$.6H$_2$O, H$_2$O, MeOH, rt., 24 hours.

Tetrahydrofuran (THF), dichloromethane (DCM), acetonitrile ($CH_3CN$) and N,N-Diisopropylethylamine (DIPEA) were dried over calcium hydride ($CaH_2$). All reactions were carried out with anhydrous solvents under nitrogen atmosphere, unless otherwise specified. All the reagents were obtained commercially with high quality and used without further purification. Reactions were monitored by thin-layer chromatography (TLC) which was carried out on silica gel plates (0.25 mm, 60E-254) by using UV light as visualizing method. Flash column chromatography was carried out on 200-300 mesh silica gel. $^1H$ and $^{13}C$ NMR spectra were recorded on a 400 ($^1H$: 400 MHz, $^{13}C$: 100 MHz) spectrometer. The following abbreviations were used to explain the multiplicities: s=singlet, d=doublet, t=triplet, q=quartet, dd=doublet of doublets, m=multiplet, br=broad. High resolution mass spectra were obtained from an ESI or MALDI-TOF mass spectrometer. The synthetic route for the primary cilium specific probe HGEu001 and its motif complex HGEu002 is shown in FIG. 29.

Synthesis of N-(4-iodophenyl)-4-(trifluoromethyl)benzamide (Compound 2)

Figure 16:
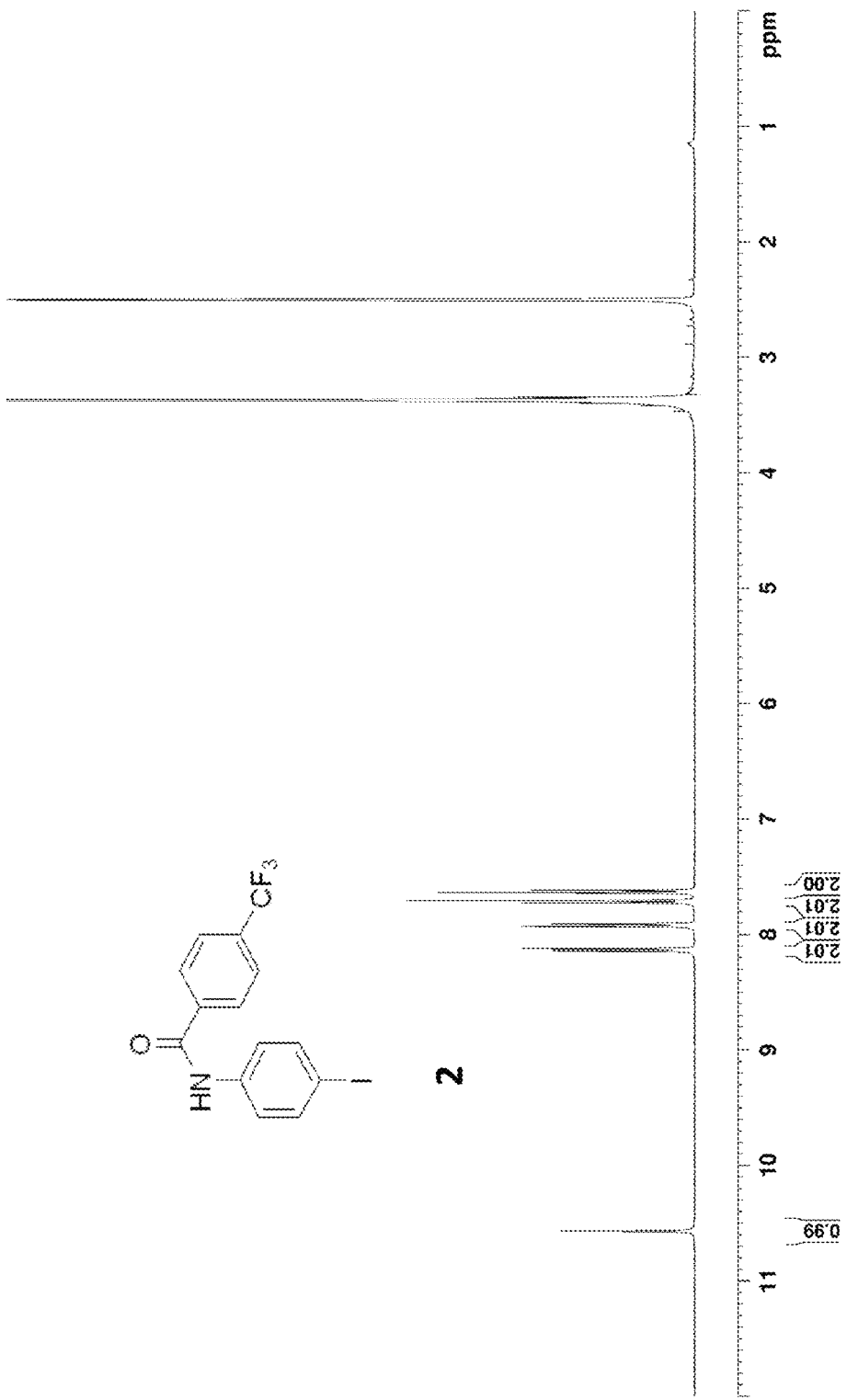
FIG. 16 shows H NMR spectrum of compound 2. (400 MHz, DMSO-d$_6$).
Figure 17:
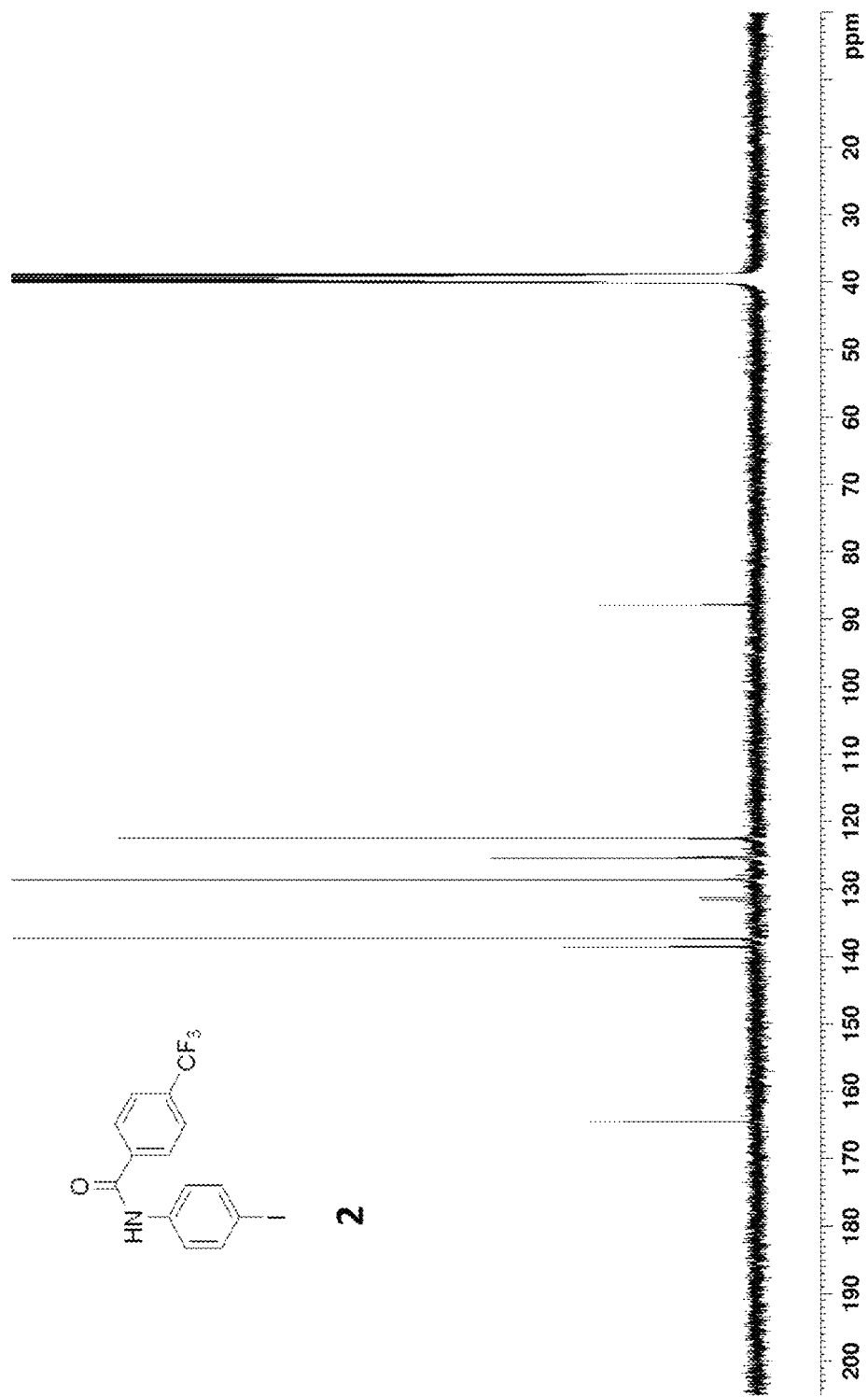
FIG. 17 shows C NMR spectrum of compound 2. (100 MHz, DMSO-d$_6$).

The solution of 4-iodoaniline (5 g, 46.23 mmol) and DIPEA (13.42 mL, 77.06 mmol) in DCM (200 mL), 4-(trifluoromethyl)benzoyl chloride (5.72 mL, 38.53 mmol) was added dropwise at 0° C. in 30 min. The resulting solution was stirred for 12 hours at room temperature. The solvent of the resulting mixture was concentrated to 100 mL, and the white precipitate was collected as product after filtration. (13.41 g, 34.29 mmol, yield=89%) $^1$H NMR (400 MHz, DMSO-d$_6$): δ 10.57 (s, 1H), 8.13 (d, J=4 Hz, 2H), 7.92 (d, J=4 Hz, 2H), 7.72 (d, J=4 Hz, 2H), 7.63 (d, J=4 Hz, 2H); (FIG. 16) $^{13}$C NMR (100 MHz, DMSO-d$_6$): δ 164.5, 138.6, 138.5, 137.3, 131.6, 131.3, 128.6, 125.4, 125.3, 125.2, 122.5, 87.9; (FIG. 17) HRMS (MALDI-TOF) m/z calcd. for $C_{14}H_{10}F_3INO$ [M+H]$^+$ 391.9759 found 391.9761.

Synthesis of N-(4-((2-(hydroxymethyl)pyridin-4-yl)ethynyl)phenyl)benzamide (Compound 3)

Figure 18:
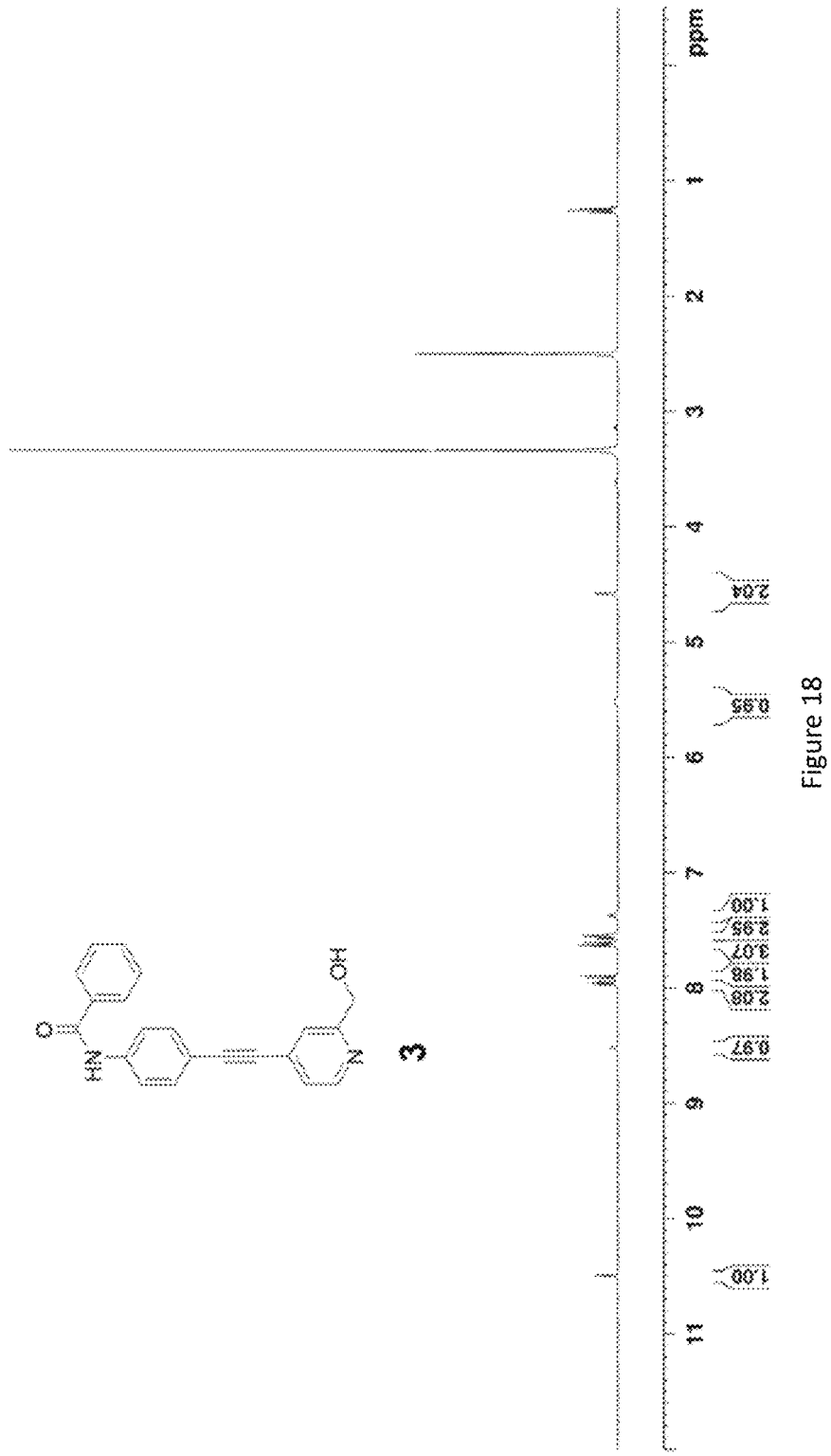
FIG. 18 shows H NMR spectrum of compound 3. (400 MHz, DMSO-d$_6$).
Figure 19:
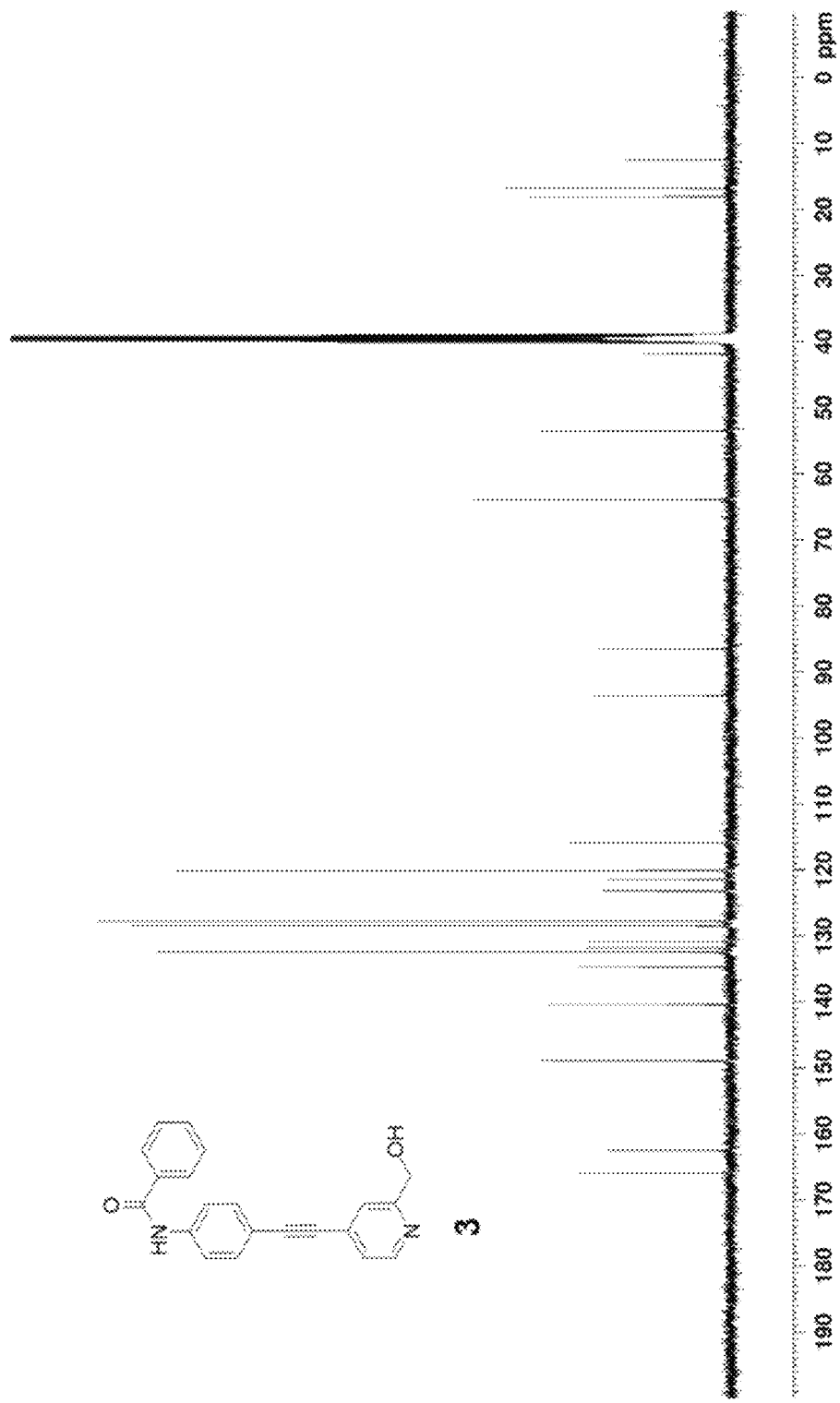
FIG. 19 shows C NMR spectrum of compound 3. (100 MHz, DMSO-d$_6$)

(4-ethynylpyridin-2-yl)methanol (0.92 g, 6.8 mmol) was added into the solution of N-(4-iodophenyl)benzamide (Compound 1) (3.36 g, 10.4 mmol), Pd(PPh$_3$)$_2$Cl$_2$ (136 mg, 0.21 mmol), CuI (80 mg, 0.42 mmol) and DIPEA (20 mL) in freshly distilled THF (200 mL). The resulting mixture was stirred at 45° C. for 6 hours under protection of N$_2$ gas. Silica gel flash column chromatography (DCM:MeOH=30:1) of the concentrated residue gave a white solid as the product. (2.16 g, 6.4 mmol, yield=94%) $^1$H NMR (400 MHz, DMSO-d$_6$): δ 10.49 (s, 1H), 8.52 (d, J=2 Hz, 1H), 7.96 (d, J=4 Hz, 2H), 7.90 (dd, =4 Hz, J$_2$=8 Hz, 2H), 7.63-7.60 (m, 3H), 7.57-7.53 (m, 3H), 7.38 (d, J=2 Hz, 1H), 5.52 (br, 1H), 4.58 (s, 2H); (FIG. 18) $^{13}$C NMR (100 MHz, DMSO-d$_6$): δ 165.8, 162.5, 148.9, 140.4, 134.7, 132.4, 131.8, 130.8, 128.4, 127.7, 123.2, 121.4, 120.1, 115.9, 93.6, 86.6, 63.9, 53.5; (FIG. 19) HRMS (MALDI-TOF) m/z calcd. for $C_{21}H_{17}N_2O_2$ [M+H]$^+$ 329.1290 found 329.1295.

Synthesis of N-(4-((2-(hydroxymethyl)pyridin-4-yl)ethynyl)phenyl)-4-(trifluoromethyl)benzamide (Compound 4)

Figure 21:
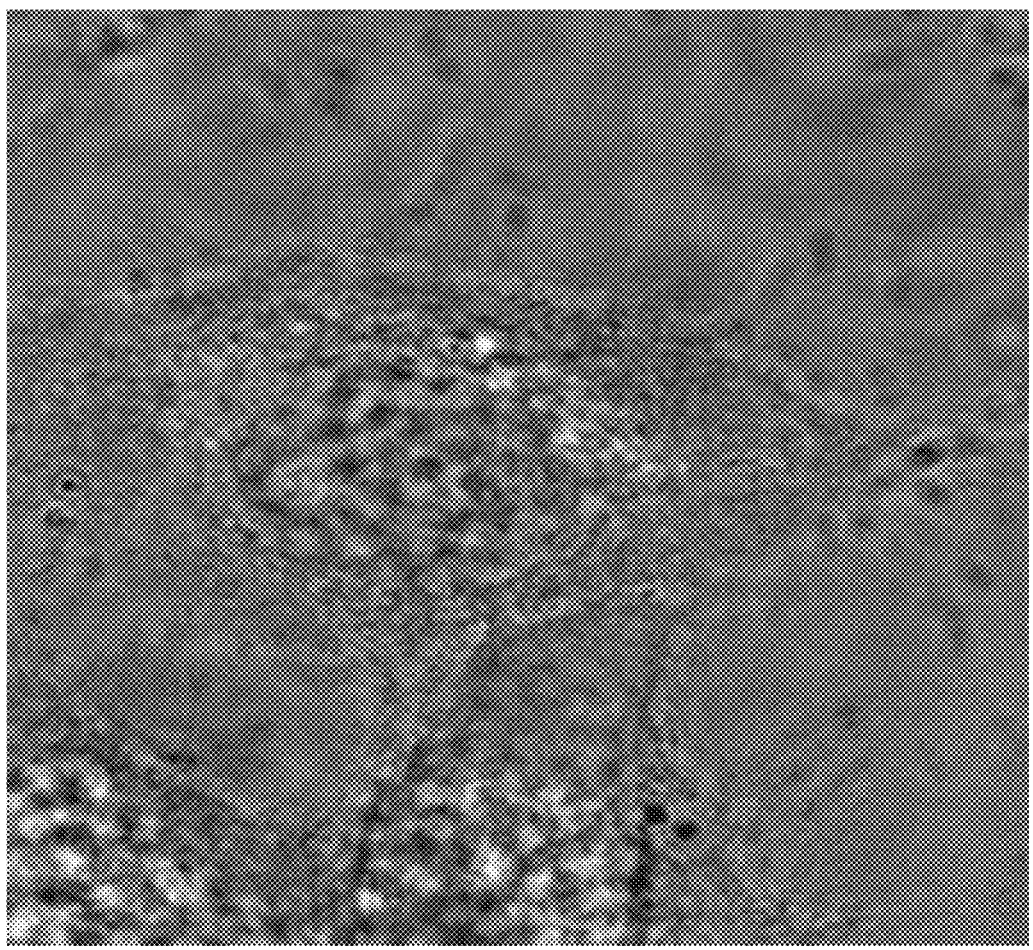
FIG. 21 shows C NMR spectrum of compound 4. (100 MHz, DMSO-d$_6$)
Figure 3A:
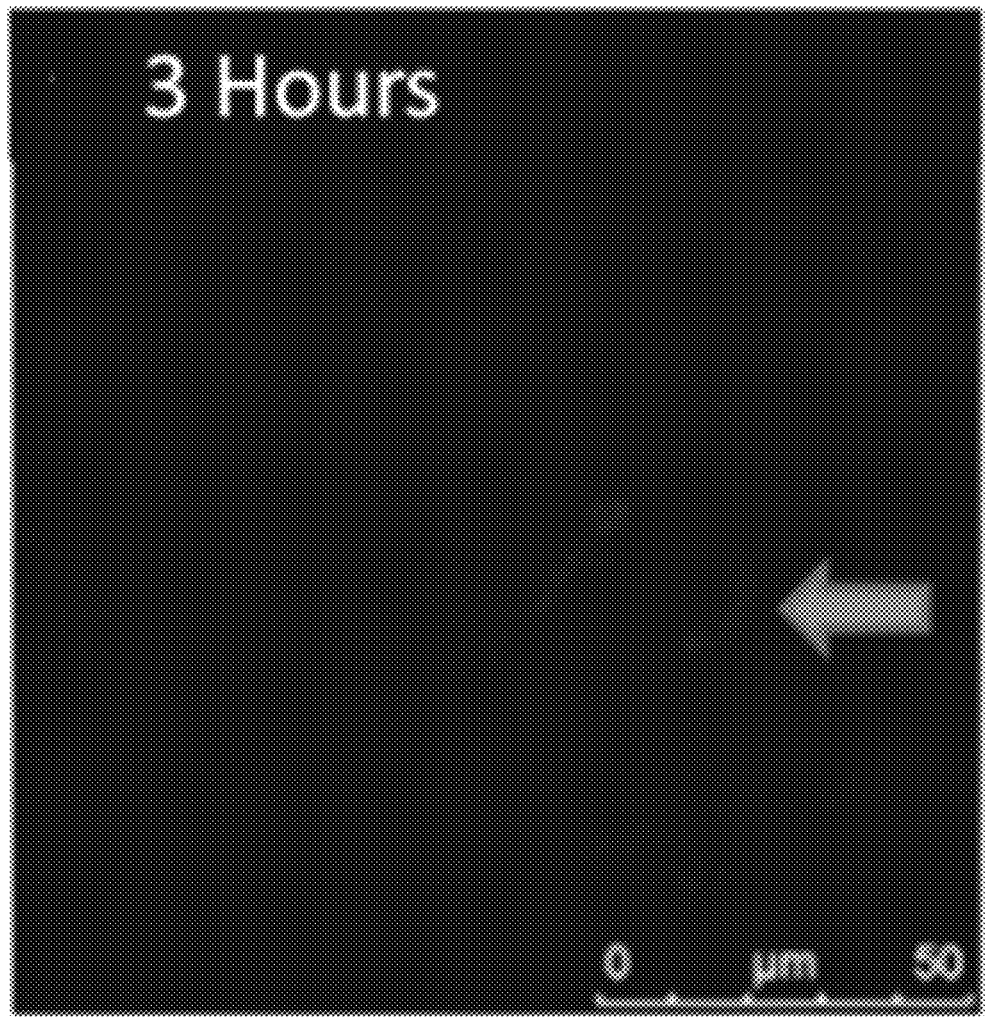
FIG. 3A shows the two-photon time lapses in vitro images of HGEu001 in HeLa cells of which the images were taken at 3 hours incubation time points. The red emission of HGEu001 (arrows) is localized in primary cilium.
Figure 3B:
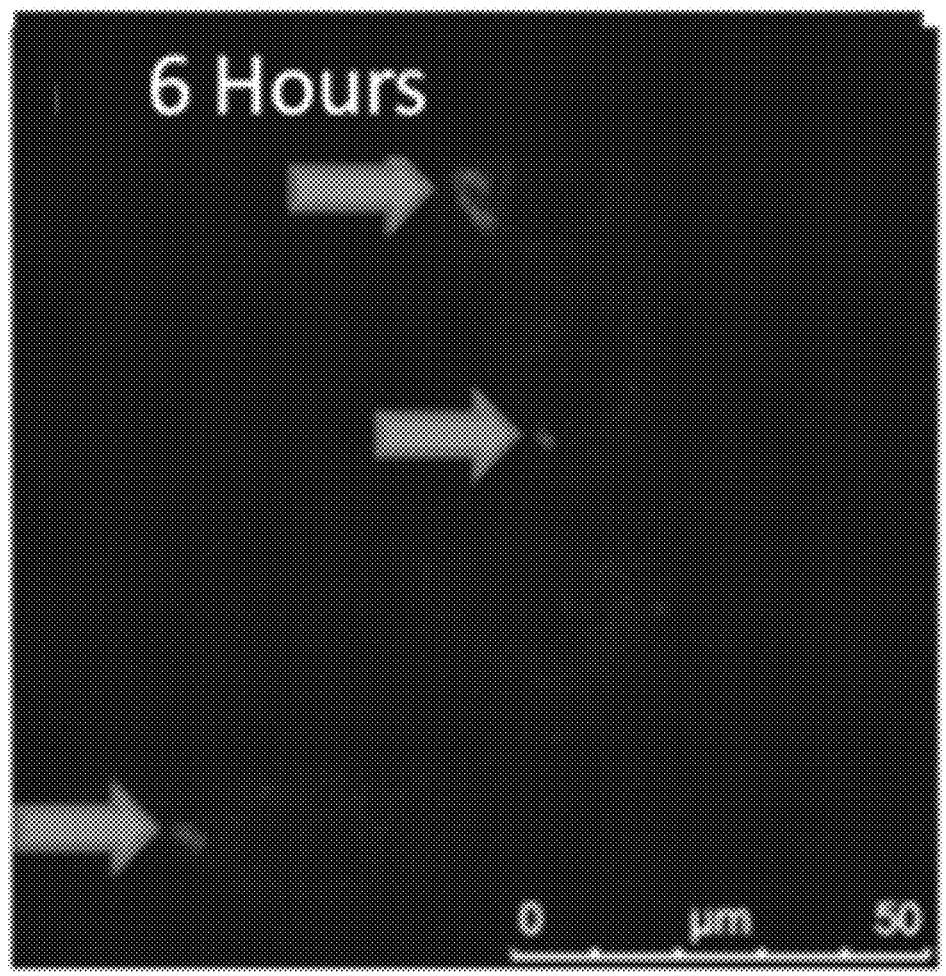
FIG. 3B shows the two-photon time lapses in vitro images of HGEu001 in HeLa cells of which the images were taken at 6 hours incubation time points. The red emission of HGEu001 (arrows) is localized in primary cilium.
Figure 3C:
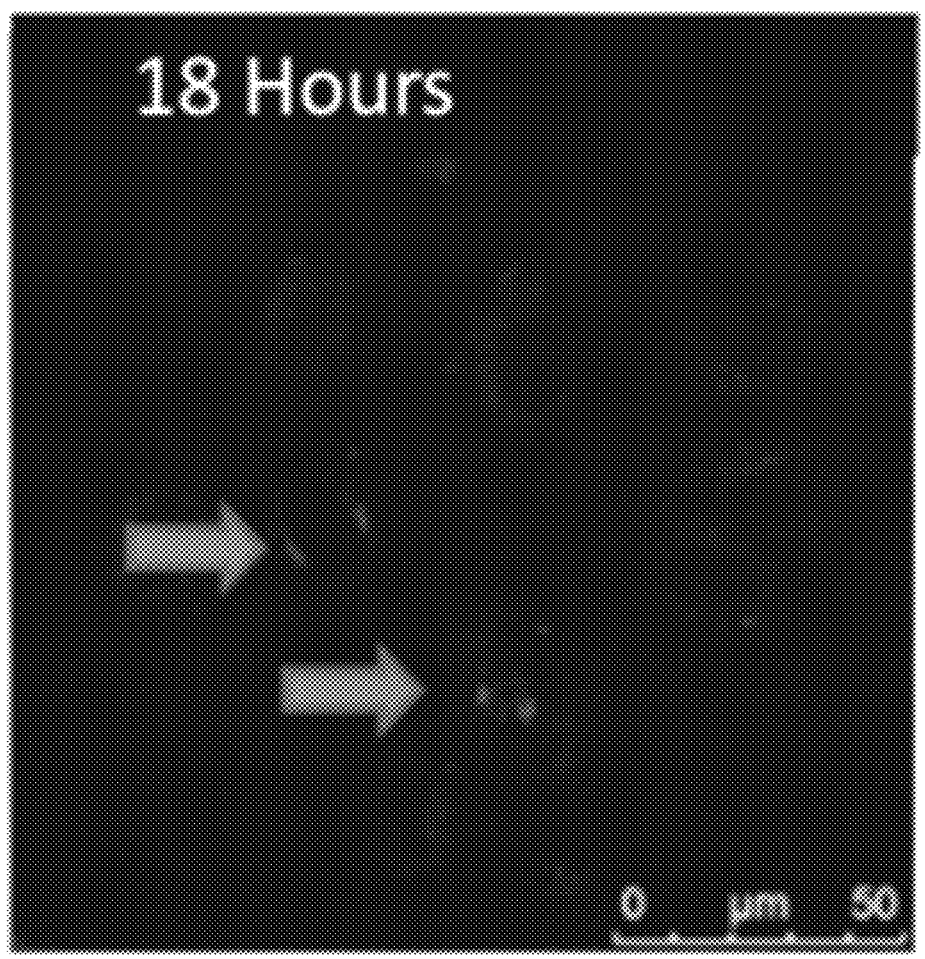
FIG. 3C shows the two-photon time lapses in vitro images of HGEu001 in HeLa cells of which the images were taken at 18 hours incubation time points. The red emission of HGEu001 (arrows) is localized in primary cilium.
Figure 3D:
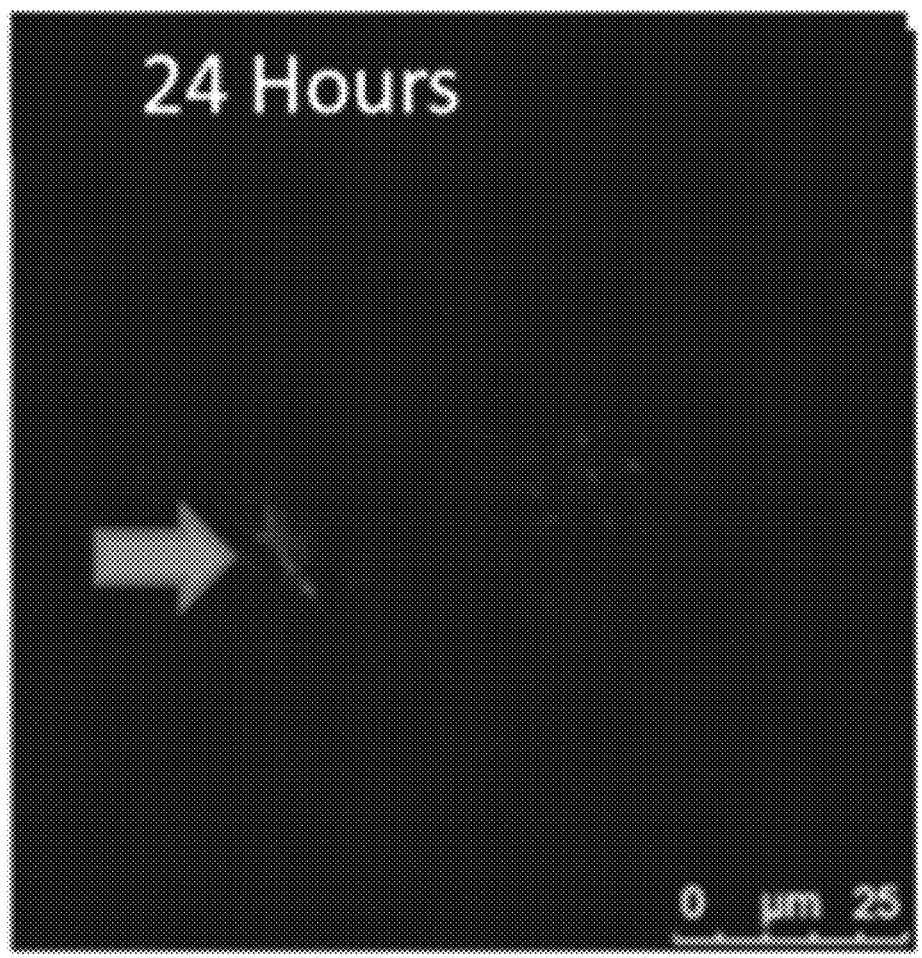
FIG. 3D shows the two-photon time lapses in vitro images of HGEu001 in HeLa cells of which the images were taken at 24 hours incubation time points. The red emission of HGEu001 (arrows) is localized in primary cilium.
Figure 3E:
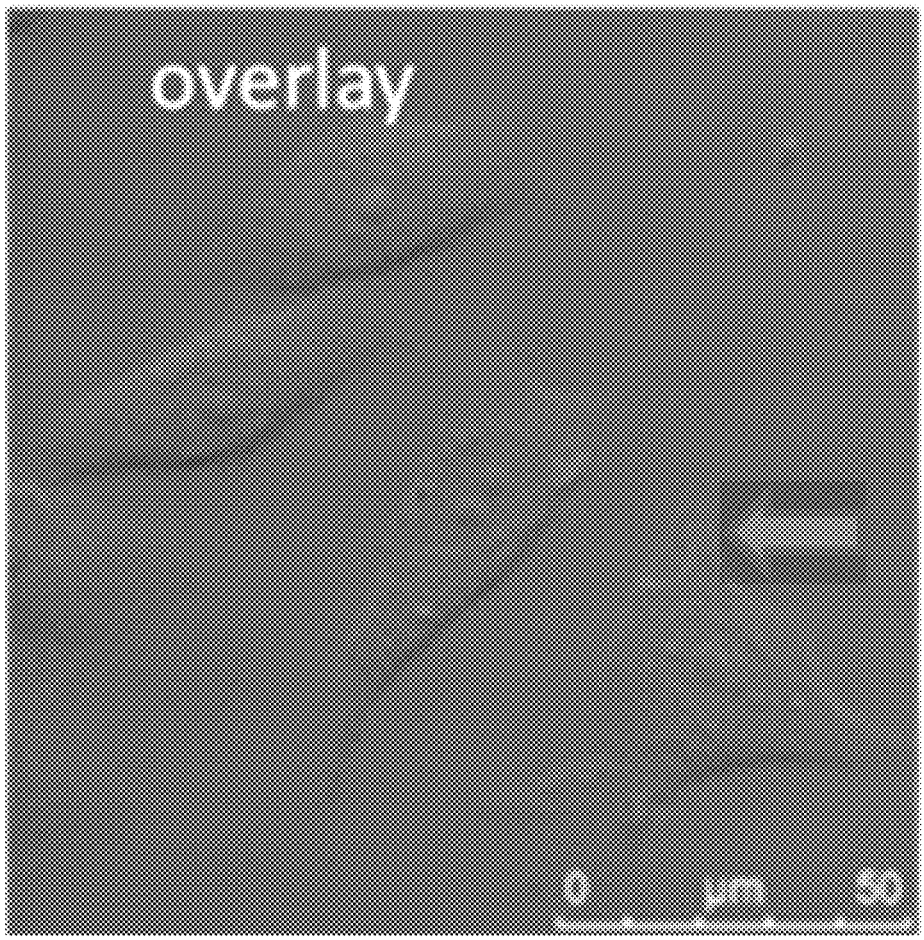
FIG. 3E shows the overlay images of fluorescence channel shown in FIG. 3A and bright field channel (Dosed concentration=10 μM, $\lambda_{ex}$=700 nm, filter Bandpass=550-665 nm). The red emission of HGEu001 (arrows) is localized in primary cilium.
Figure 3F:
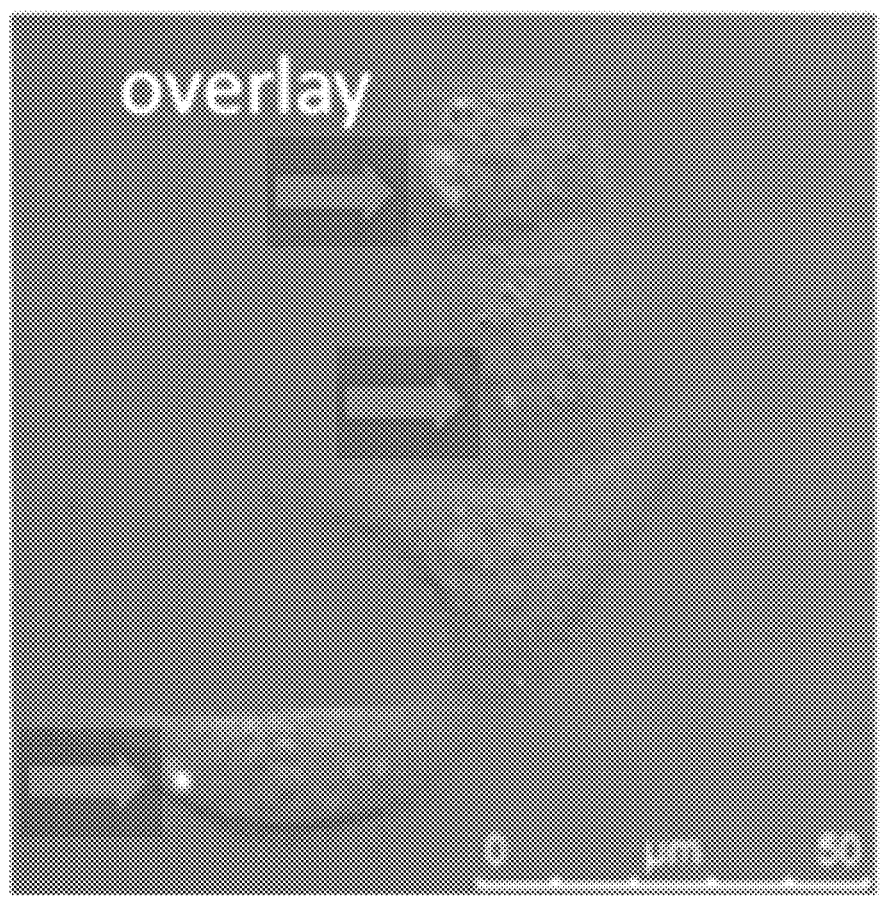
FIG. 3F shows the overlay images of fluorescence channel shown in FIG. 3B and bright field channel (Dosed concentration=10 μM, $\lambda_{ex}$=700 nm, filter Bandpass=550-665 nm). The red emission of HGEu001 (arrows) is localized in primary cilium.
Figure 3G:
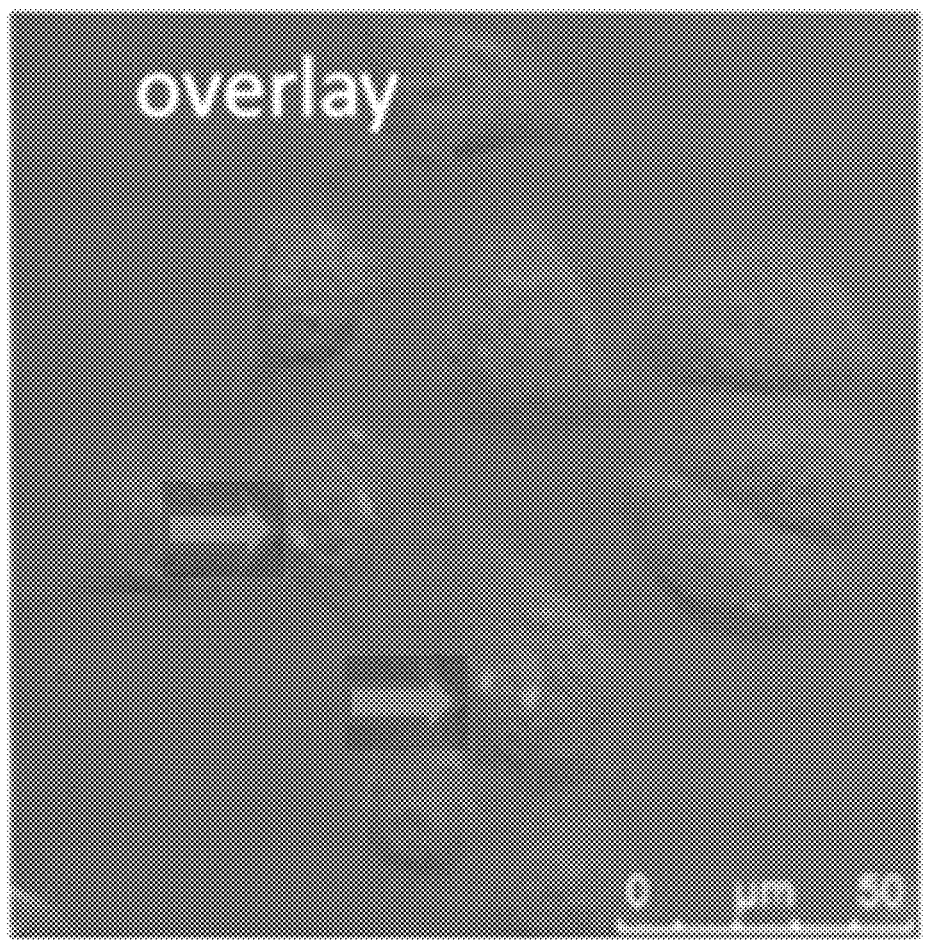
FIG. 3G shows the overlay images of fluorescence channel shown in FIG. 3C and bright field channel (Dosed concentration=10 μM, $\lambda 0_{ex}$=700 nm, filter Bandpass=550-665 nm). The red emission of HGEu001 (arrows) is localized in primary cilium.
Figure 3H:
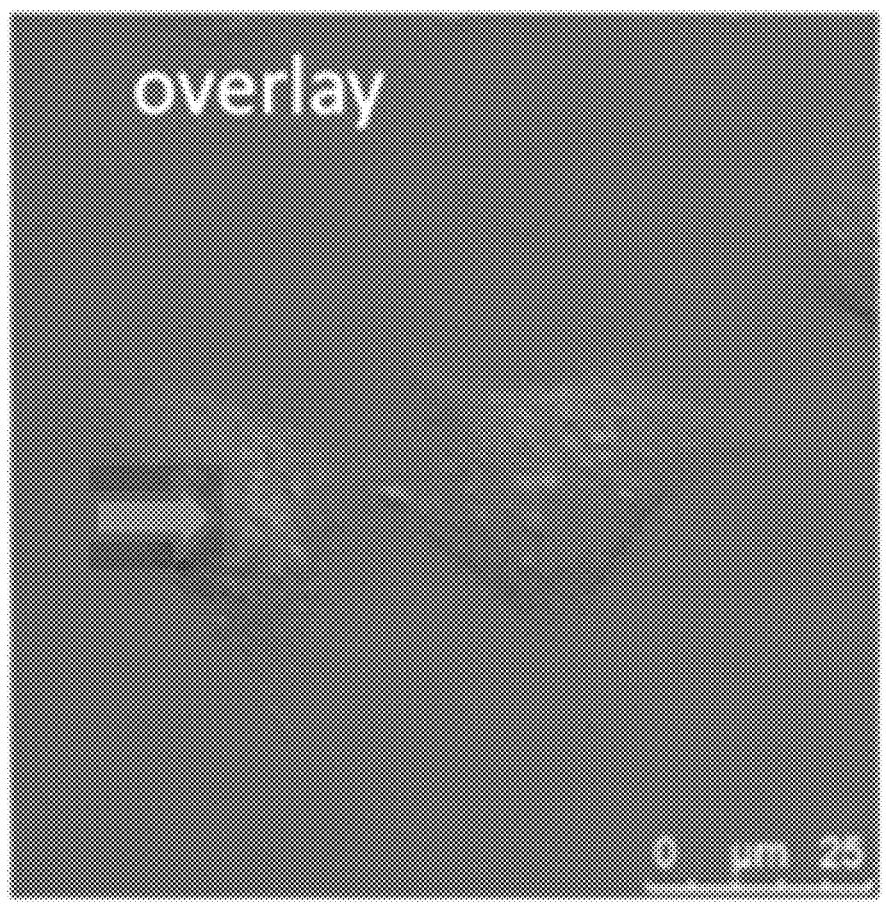
FIG. 3H shows the overlay images of fluorescence channel shown in FIG. 3D and bright field channel (Dosed concentration=10 μM, $\lambda_{ex}$=700 nm, filter Bandpass=550-665 nm). The red emission of HGEu001 (arrows) is localized in primary cilium.
Figure 20:
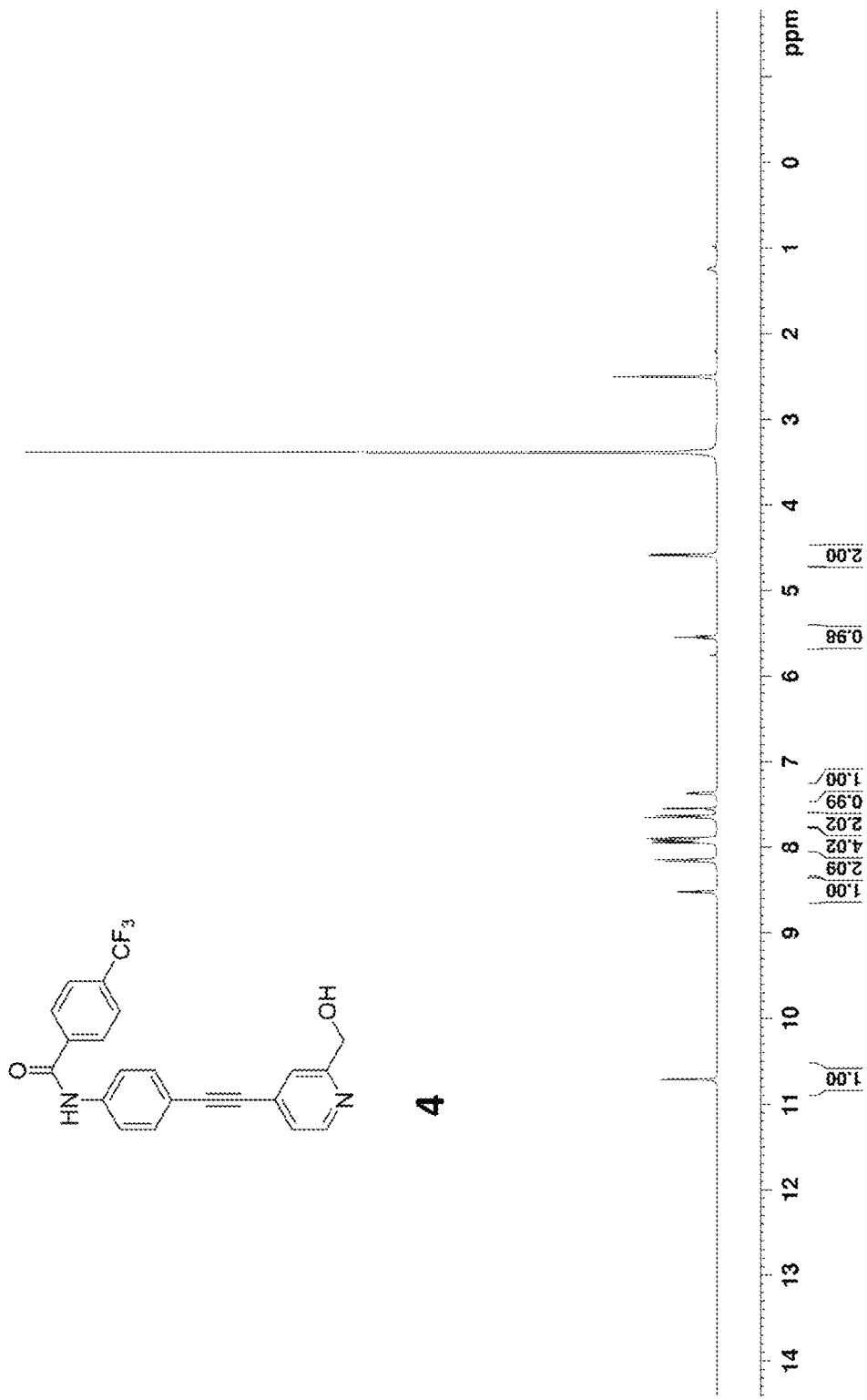
FIG. 20 shows H NMR spectrum of compound 4. (400 MHz, DMSO-d$_6$)
Figure 21:
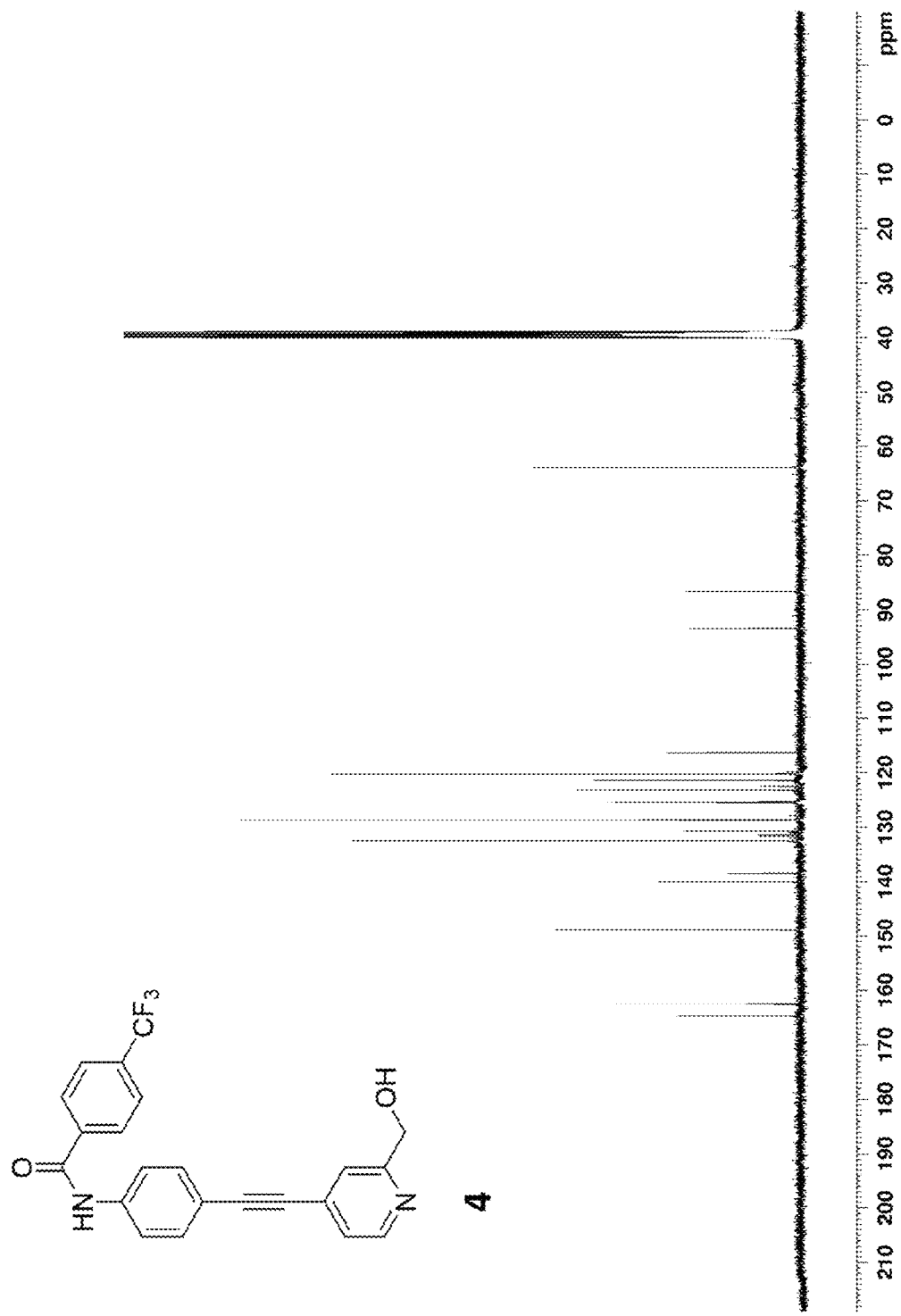

(4-ethynylpyridin-2-yl)methanol (1.13 g, 8.52 mmol) was added into the solution of N-(4-iodophenyl)-4-(trifluoromethyl)benzamide (Compound 2) (4 g, 10.22 mmol), Pd(PPh$_3$)$_4$ (197 mg, 0.17 mmol), CuI (65 mg, 0.34 mmol) and DIPEA (20 mL) in freshly distilled THF (200 mL). The resulting mixture was stirred at 45° C. for 6 hours under protection of N$_2$ gas. Silica gel flash column chromatography (DCM:MeOH=30:1) of the concentrated residue gave a white solid as the product. (3.10 g, 7.84 mmol, yield=92%) $^1$H NMR (400 MHz, DMSO-d$_6$): δ 10.71 (s, 1H), 8.52 (d, J=4 Hz, 1H), 8.15 (d, J=4 Hz, 2H), 7.93 (d, J=4 Hz, 2H), 7.90 (d, J=4 Hz, 2H), 7.64 (d, J=4 Hz, 2H), 7.55 (s, 1H), 7.36 (d, J=2 Hz, 1H), 5.54 (t, J=4 Hz, 1H), 4.14 (d, J=2 Hz, 2H); (FIG. 20) $^{13}$C NMR (100 MHz, DMSO-d$_6$): δ 164.7, 162.5, 148.9, 140.0, 138.5, 132.5, 131.7, 131.3, 130.70, 128.7, 125.4, 125.2, 123.2, 122.5, 121.4, 120.2, 116.3, 93.4, 86.6, 63.9; (FIG. 21) HRMS (MALDI-TOF) m/z calcd. for $C_{22}H_{16}F_3N_2O_2$ [M+H]$^+$ 397.1164 found 397.1168.

Synthesis of 2,2',2''-(1,4,7,10-tetraazacyclododecane-1,4,7-triyl)tris(N-(tert-butyl)acetamide) (Compound 5)

Figure 22:
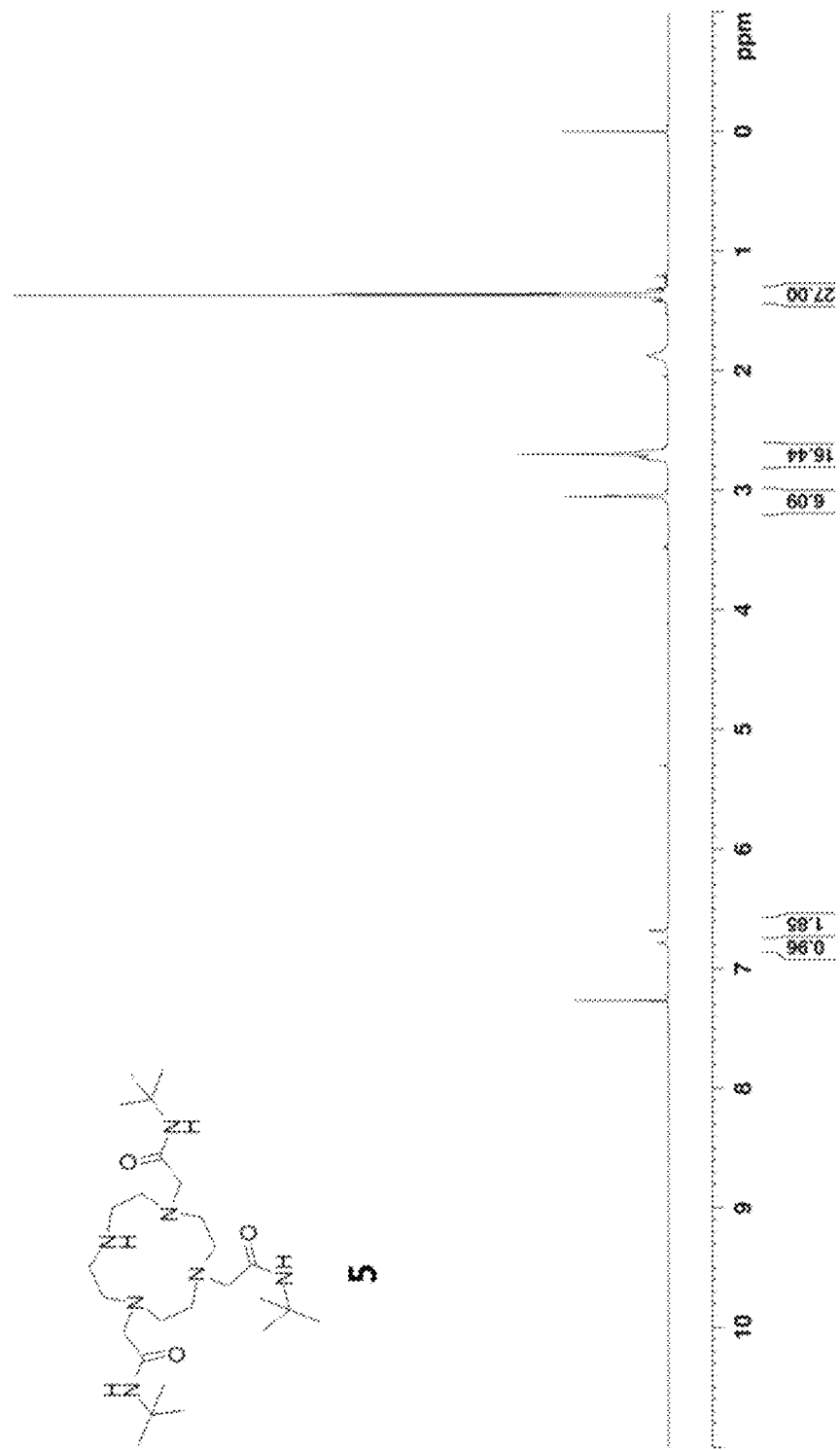
FIG. 22 shows H NMR spectrum of compound 5. (400 MHz, CDCl$_3$)
Figure 23:
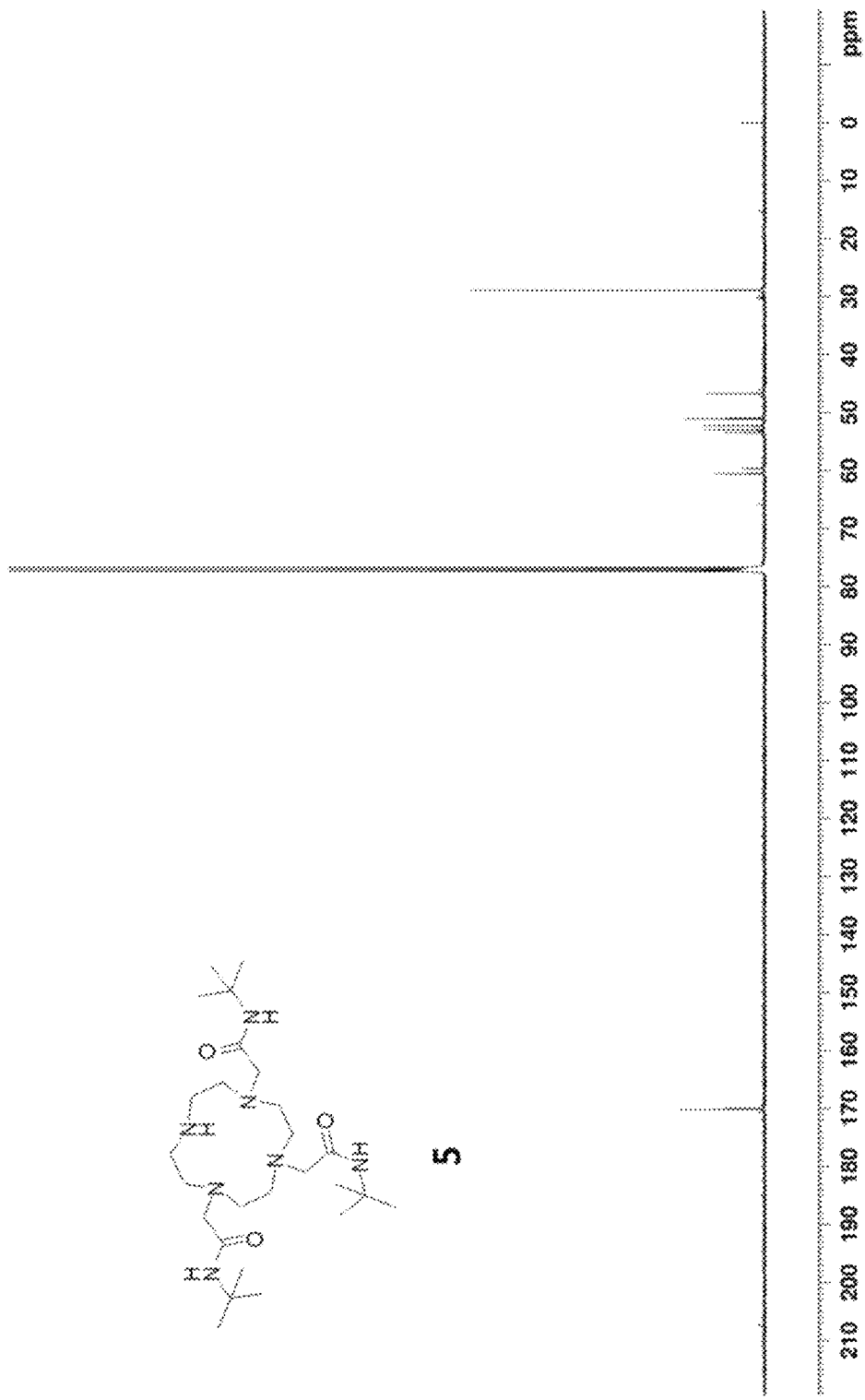
FIG. 23 shows C NMR spectrum of compound 5. (100 MHz, CDCl$_3$)

2-bromo-N-(tert-butyl)acetamide (10.1 g, 52.2 mmol) was added into the solution of 1,4,7,10-tetraazacyclododecane (3.0 g, 17.4 mmol) in anhydrous acetonitrile (80 mL), followed by NaHCO$_3$ (21.9 g, 261 mmol). The resulting solution was stirred at room temperature for 24 hours. After filtration of the resulting mixture, filtrate was concentrated and recrystallized from hot water to obtain a white solid as the product. (4.8 g, 8.7 mmol, yield=50%) $^1$H NMR (400 MHz, CDCl$_3$): δ 6.78 (s, 1H), 6.68 (s, 2H), 3.05 (s, 4H), 3.05 (s, 2H), 2.70 (m, 16H), 1.37 (s, 18H) 1.36 (s, 9H); (FIG. 22) $^{13}$C NMR (100 MHz, CDCl$_3$): δ 170.1, 170.0, 60.5, 59.6, 53.4, 52.9, 52.3, 51.1, 50.9, 46.7, 28.9, 28.8; (FIG. 23) HRMS (MALDI-TOF) m/z calcd. For $C_{26}H_{54}N_7O_3$ [M+H]$^+$ 512.4288 found 512.4285.

Synthesis of 2,2',2''-(10-((4-((4-benzamidophenyl)ethynyl)pyridin-2-yl)methyl-1,4,7,10-tetraazacyclododecane-1,4,7-triyl)tris(N-(tert-butyl)acetamide) (HGL001)

Figure 24:
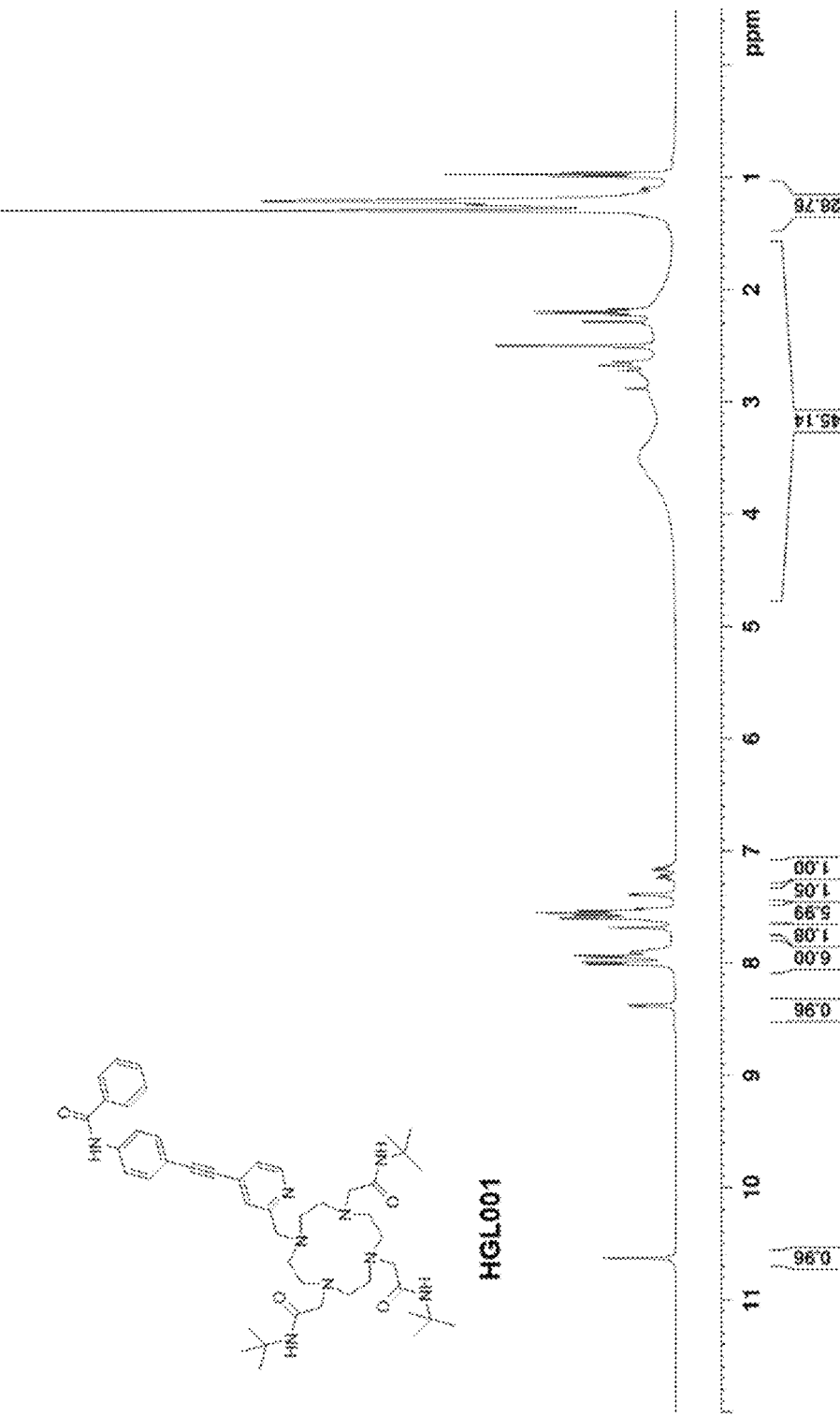
FIG. 24 shows H NMR spectrum of HGL001. (400 MHz, DMSO-d$_6$)
Figure 25:
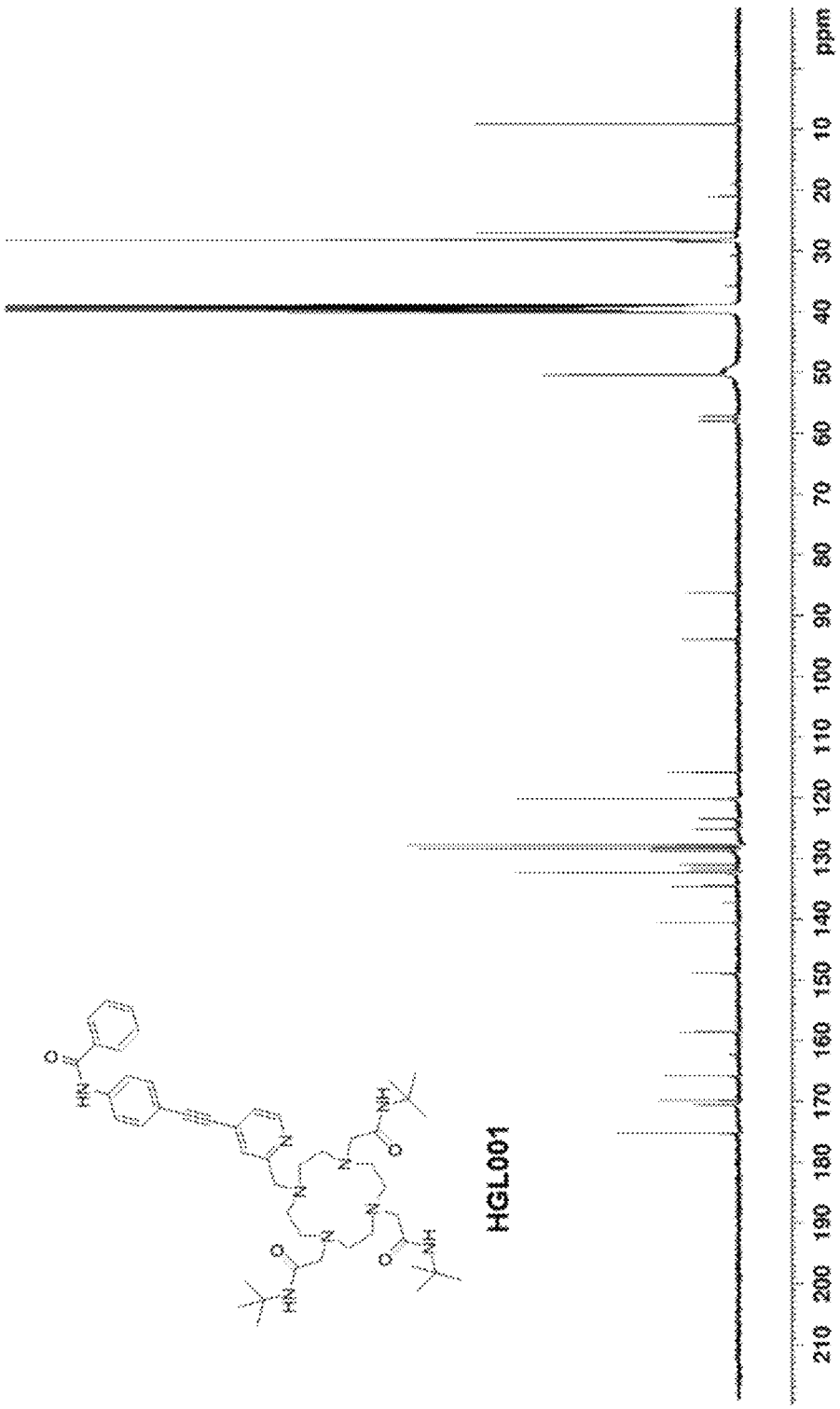
FIG. 25 shows C NMR spectrum of HGL001. (100 MHz, DMSO-d$_6$)

Methanesulfonyl chloride (0.22 mL, 2.73 mmol) was added into a stirred solution of N-(4-((2-(hydroxymethyl)pyridin-4-yl)ethynyl)phenyl)benzamide (Compound 3) (300 mg, 0.91 mmol) in anhydrous DCM (150 mL) and DIPEA (1.59 mL, 9.11 mmol). The resulting mixture was stirred at room temperature for 3 hours. The solution was then washed with saturated NaHCO$_3$ solution, saturated NH$_4$Cl solution and brine. The organic layer was dried over anhydrous Na$_2$SO$_4$ and concentrated to give a pale yellow solid as the intermediate compound, (4-((4-benzamidophenyl)ethynyl)pyridin-2-yl)methyl methanesulfonate, which was directly used in the next step without further purification. The pale yellow solid was dissolved in dry CH$_3$CN (50 mL). 2,2',2''-(1,4,7,10-tetraazacyclododecane-1,4,7-triyl)tris(N-tert-butyeacetamide) (Compound 5, 0.50 g, 0.61 mmol) and anhydrous K$_2$CO$_3$ (1.26 g, 9.1 mmol) were added. The resulting mixture was stirred at 50° C. for 12 hours under N$_2$ gas. The solids were filtered off, and the filtrate was concentrated. Silica gel flesh column chromatography (CH$_2$Cl$_2$: MeOH=12:1) of the residue gave a pale yellow solid as the product (378 mg, 0.46 mmol, yield=75%,). $^1$H NMR (400 MHz, DMSO-d$_6$): δ 10.53 (s, 1H), 8.38 (d, J=2 Hz, 1H), 7.97 (d, J=4 Hz, 2H), 7.94 (d, J=4 Hz, 2H), 7.83 (br, 2H), 7.60-7.53 (m, 7H), 7.38 (d, J=2 Hz, 1H), 3.66 (br, 2H), 3.20-2.07 (m, 22H), 1.30 (s, 9H), 1.22 (s, 18H); (FIG. 24) $^{13}$C NMR (100 MHz, DMSO-d$_6$): δ 170.5, 169.9, 165.9, 158.7, 149.0, 140.5, 134.7, 132.3, 131.8, 131.1, 128.5, 128.2, 127.8, 125.1, 123.5, 120.1, 115.9, 93.9, 86.3, 58.1, 57.9, 57.2, 50.4, 50.3, 28.3, 28.1; (FIG. 25) HRMS (MALDI-TOF) m/z calcd. for $C_{47}H_{68}N_9O_4$ [M+H]$^+$ 822.5394, found 822.5390.

Synthesis of 2,2',2''-(10-((4-((4-(4-(trifluoromethyl)benzamido)phenyl)ethynyl)pyridin-2-yl)methyl)-1,4,7,10-tetraazacyclododecane-1,4,7-triyl)tris(N-(tert-butyl)acetamide) (HGL002)

Figure 26:
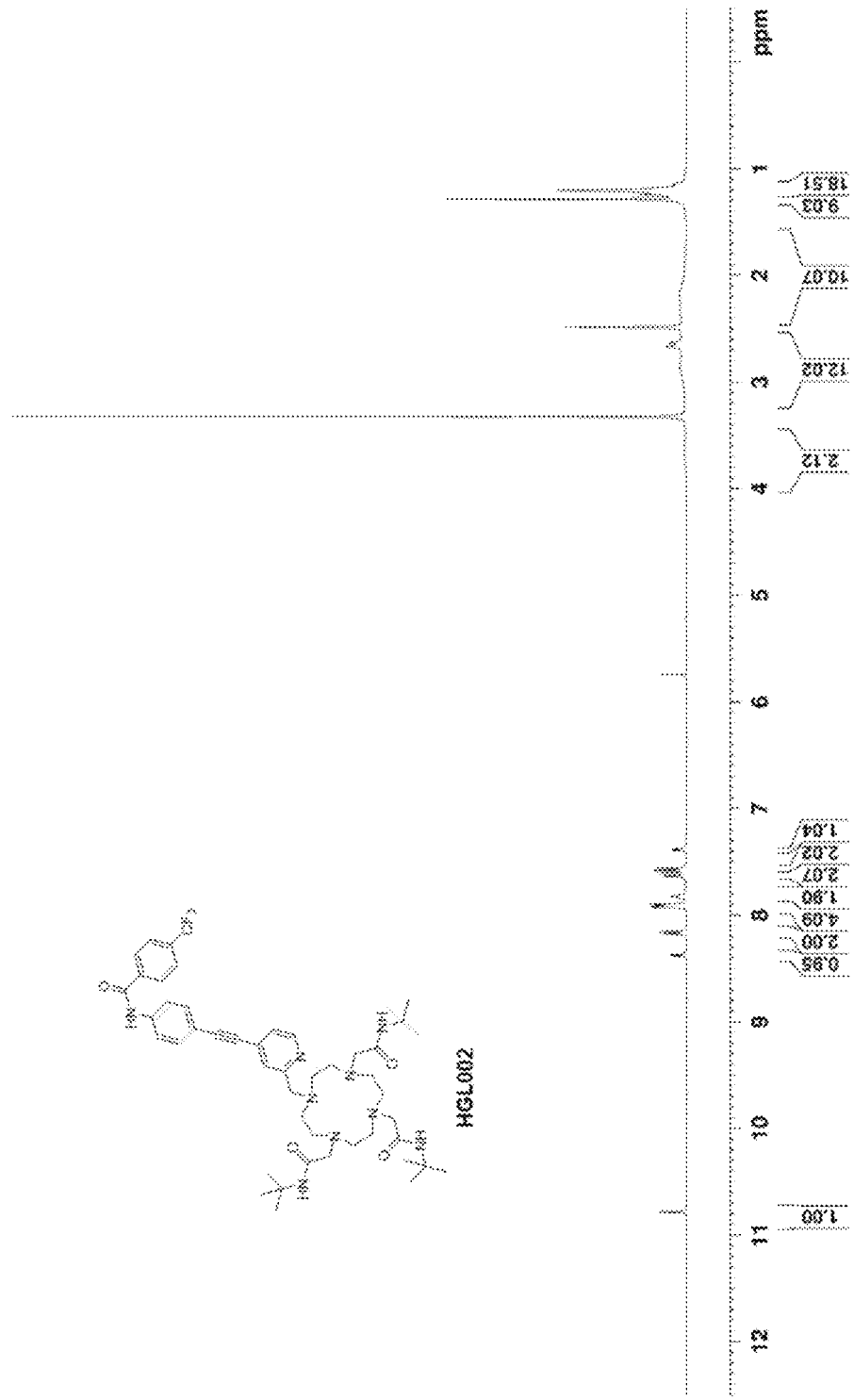
FIG. 26 shows H NMR spectrum of HGL002. (400 MHz, DMSO-d$_6$)
Figure 27:
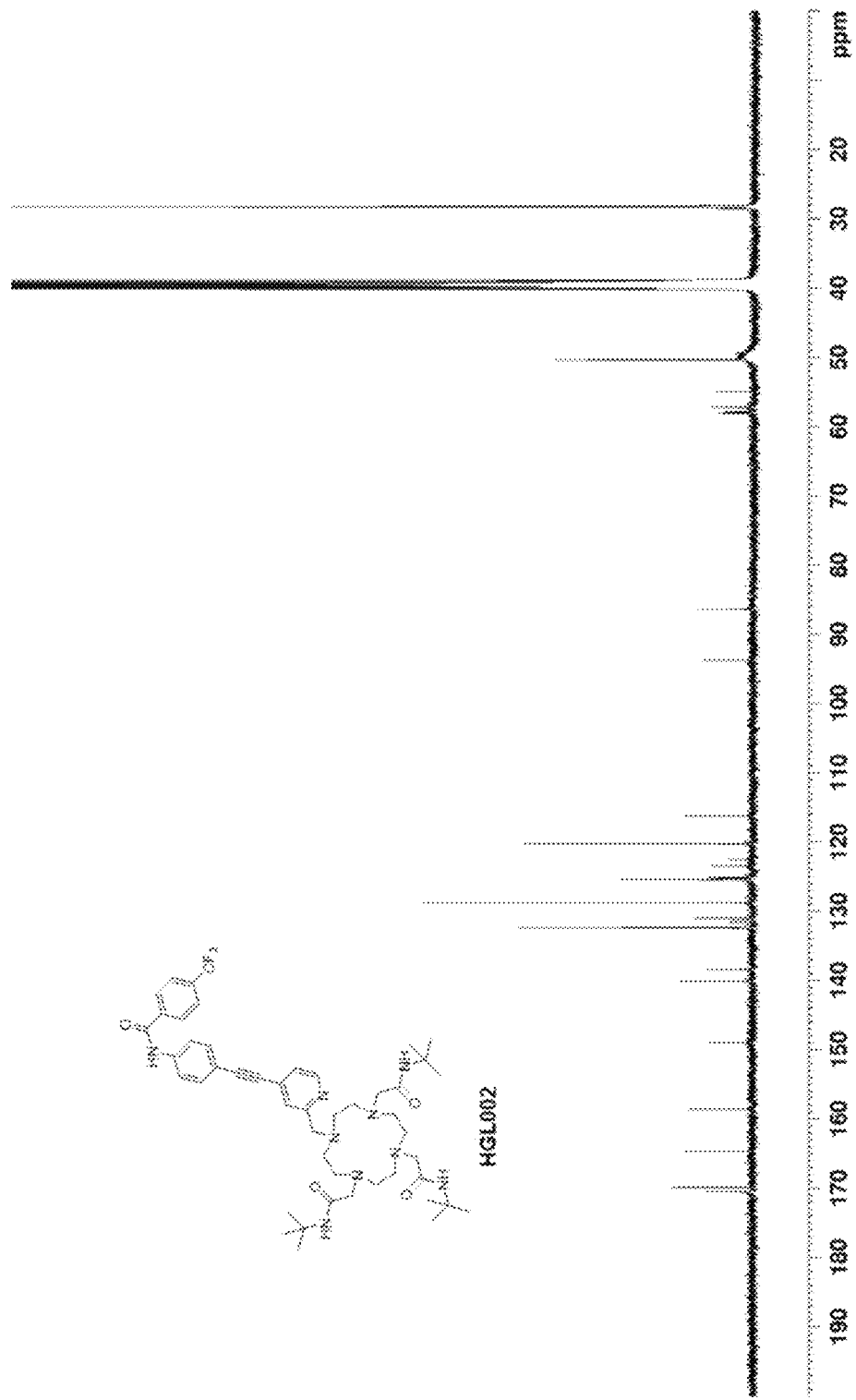
FIG. 27 shows C NMR spectrum of HGL002. (100 MHz, DMSO-d$_6$)

Methanesulfonyl chloride (0.18 mL, 2.28 mmol) was added into a stirred solution of N-(4-((2-(hydroxymethyl)pyridin-4-yl)ethynyl)phenyl)-4-(trifluoromethyl)benzamide (Compound 4) (300 mg, 0.76 mmol) in anhydrous DCM (150 mL) and DIPEA (1.33 mL, 7.61 mmol). The resulting mixture was stirred at room temperature for 3 hours. After that the solution was then washed with saturated NaHCO$_3$ solution, saturated NH$_4$Cl solution and brine. The organic layer was dried over anhydrous Na$_2$SO$_4$ and concentrated to give a pale yellow solid as the intermediate compound, (4-((4-(4-(trifluoromethyl)benzamido)phenyl)ethynyl)pyridin-2-yl)methyl methanesulfonate, which was directly used in the next step without further purification. The pale yellow solid was dissolved in dry $CH_3CN$ (50 mL). 2,2',2"-(1,4,7,10-tetraazacyclododecane-1,4,7-triyl)tris(N-(tert-butyl)acetamide) (Compound 5, 0.42 g, 0.51 mmol) and anhydrous $K_2CO_3$ (1.05 g, 7.6 mmol) were added. The resulting mixture was stirred at 50° C. for 12 hours under $N_2$ gas. The solids were filtered off, and the filtrate was concentrated. Silica gel flesh column chromatography ($CH_2Cl_2$:MeOH=12:1) of the residue gave a pale yellow solid as the product (354 mg, 0.40 mmol, yield=78%). $^1$H NMR (400 MHz, DMSO-$d_6$): δ 10.78 (s, 1H), 8.38 (d, J=2 Hz, 1H), 8.18 (s, 1H), 8.16 (s, 1H), 7.91 (d, J=4 Hz, 4H), 7.82 (br, 2H), 7.62 (d, J=8 Hz, 2H), 7.57 (d, J=4 Hz, 2H), 7.39 (d, J=2 Hz, 1H), 3.71 (br, 2H), 2.87-2.17 (m, 22H), 1.29 (s, 9H), 1.27 (s, 18H); (FIG. 26) $^{13}$C NMR (100 MHz, DMSO-$d_6$): δ 170.5, 169.8, 164.7, 158.6, 148.9, 140.1, 138.4, 132.3, 131.6, 131.3, 131.0, 128.7, 125.4, 125.2, 125.1123.4, 122.5, 120.2, 116.2, 93.7, 86.4, 58.1, 57.9, 57.2, 54.9, 50.4, 50.3, 49.4, 28.3, 28.1; (FIG. 27) HRMS (MALDI-TOF) m/z calcd. for $C_{48}H_{67}F_3N_9O_4$ $[M+H]^+$ 890.5268 found 890.5264.

Synthesis of Complex HGEu001

Figure 7A:
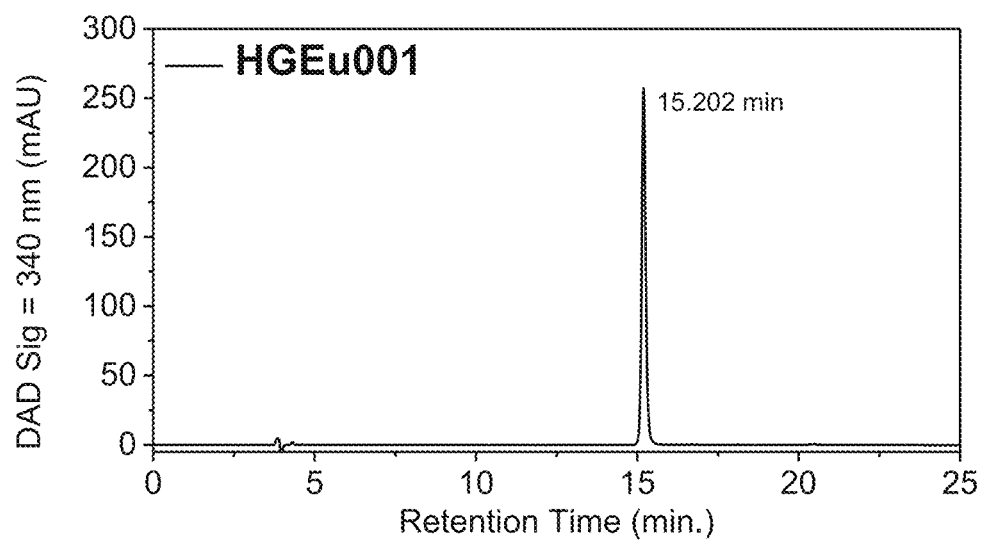
FIG. 7A shows HPLC spectra of HGEu001.
Figure 7B:
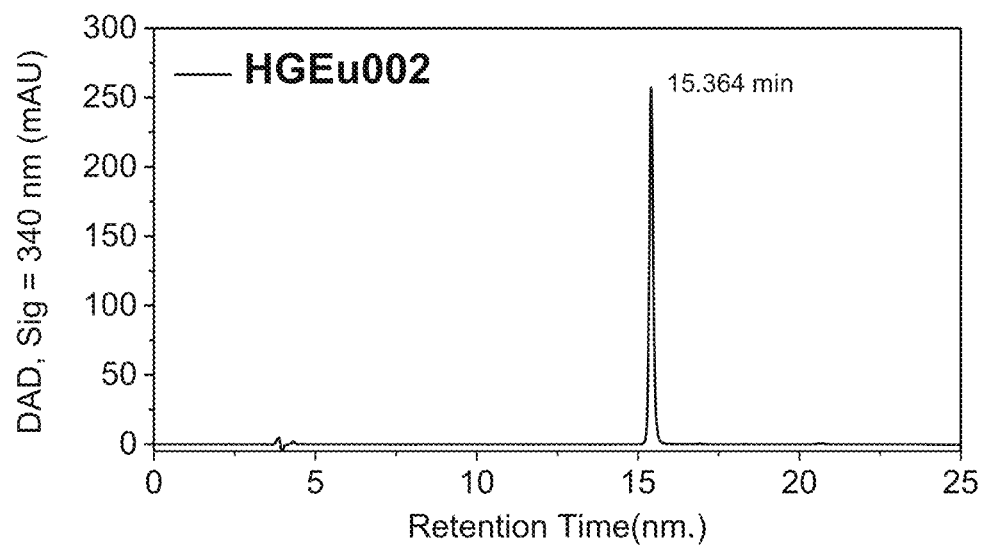
FIG. 7B shows HPLC spectra of HGEu002.
Figure 8:
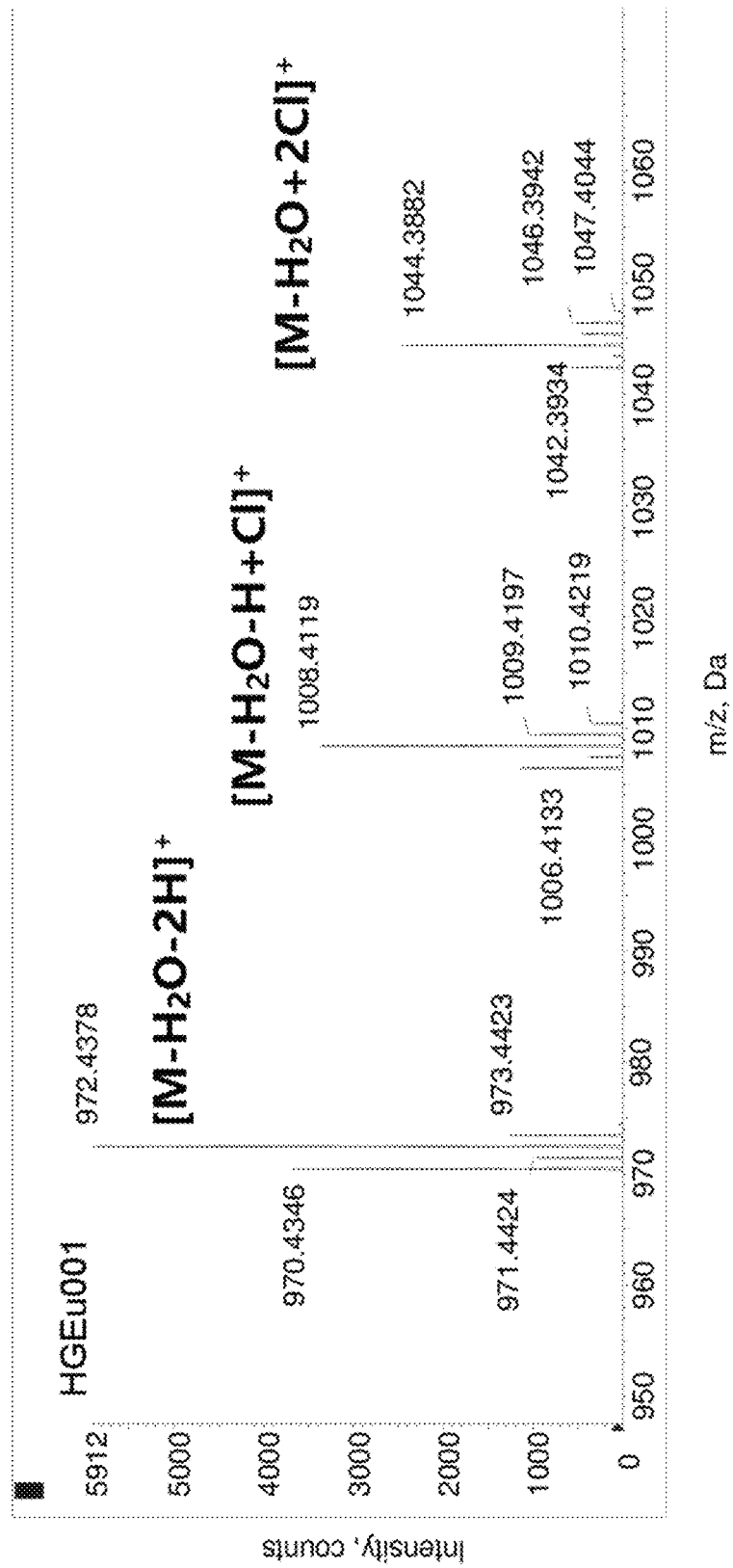
FIG. 8 shows HRMS(+ESI) spectrum of the complex HGEu001. (m/z calcd. for $C_{47}H_{65}EuN_9O_4$ [M−H2O−2]+ 972.4372, found 972.4378, calcd. for $C_{47}H_{66}ClEuN_9O_4$ [M−H2O−H+Cl-]+ 1008.4139, found 1008.4119, calcd. for $C_{47}H_{67}Cl_2EuN_9O_4$ [M−H2O+2Cl]+1044.3905, found 1044.3882.).

Europium (III) chloride hexahydrate (77 mg, 0.21 mmol) was added to the solution of the ligand (HGL001, 0.20 mmol) in MeOH/$H_2O$ (100 mL, v:v=1:1). The resulting solution was maintained in a pH range of 6.0-6.5 with NaOH solution (0.4 M) and stirred at room temperature for 24 hours. The solvents were removed under vacuum; the residue was dissolved in 1 mL of methanol and dropped into ethyl ether (50 mL). The precipitates were filtered, washed with diethyl ether and dried under vacuum at room temperature. White solids were collected as the products. (222 mg, 0.19 mmol, yield=90%). HRMS (+ESI) m/z calcd. for $C_{47}H_{65}EuN_9O_4$ $[M-H_2O-2H]+$ 972.4372, found 972.4378, calcd. for $C_{47}H_{66}ClEuN_9O_4$ $[M-H_2O-H+Cl^-]^+$ 1008.4139, found 1008.4119, calcd. for $C_{47}H_{67}Cl_2EuN_9O_4$ $[M-H_2O+2Cl]^+$ 1044.3905, found 1044.3882 (FIG. 8) HPLC characterization: Retention time=15.20 min. (Table 1 and FIGS. 7A-7B). The chemical structure of HGEu001 can be represented by the following formula:

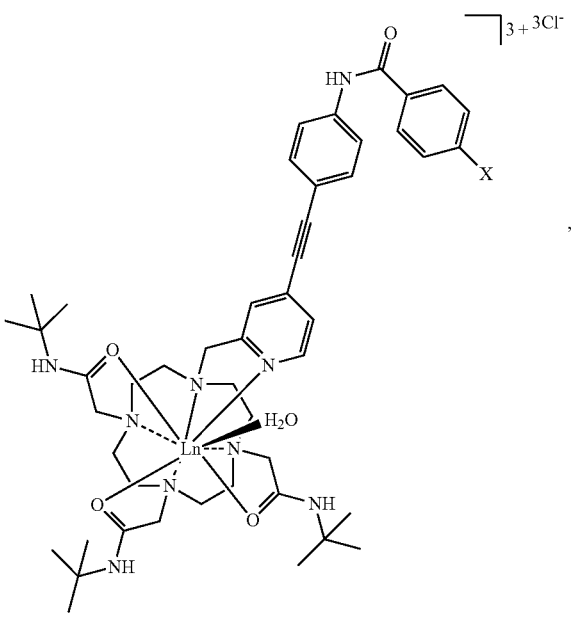

(III)

wherein X is H; Ln is Eu.

Synthesis of Complex HGEu002

Figure 9:
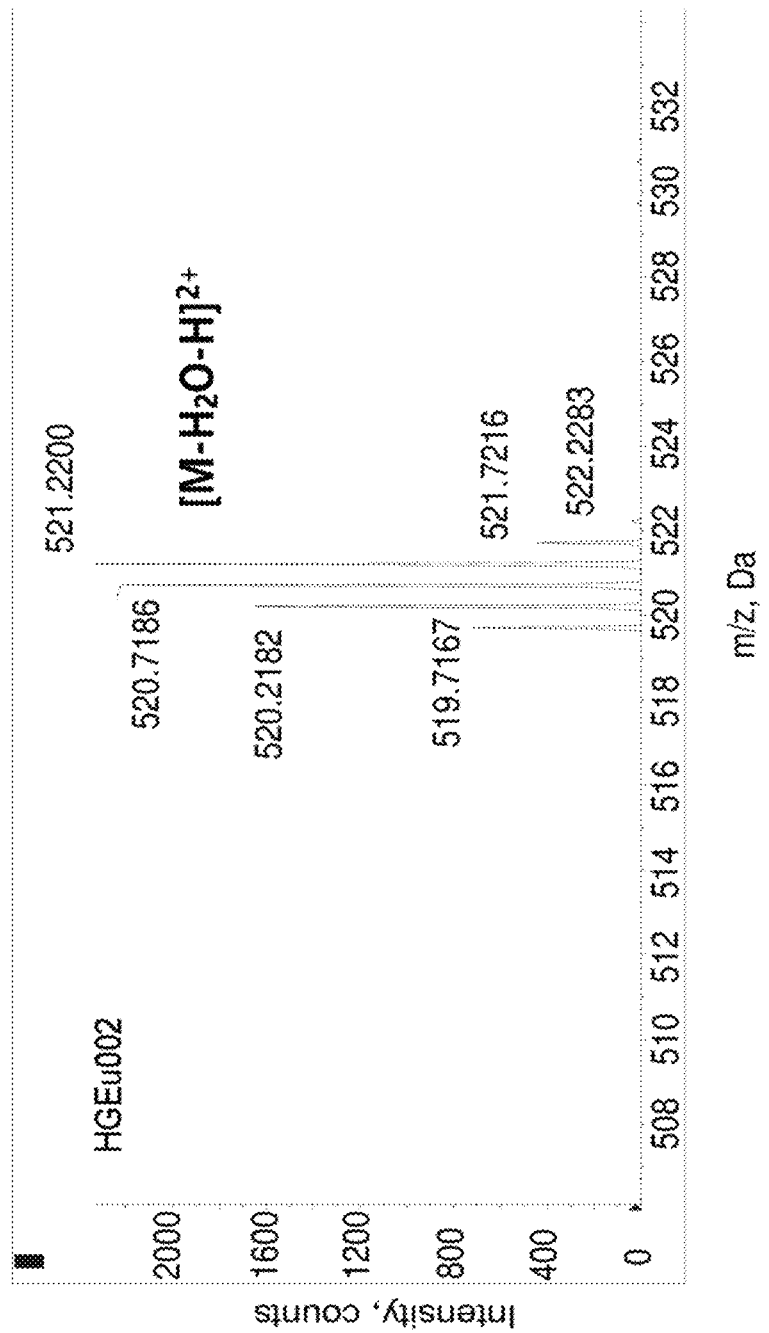
FIG. 9 shows HRMS(+ESI) spectrum of the complex HGEu002. (m/z calcd. for $C_{48}H_{65}EuF_3N_9O_4$ [M−H2O−H]$^{2+}$ m/z=1041.4324/2=520.7162, found 520.7186.

HGEu002 was obtained from ligand HGL002 with same procedures as HGEu001 (204 mg, 0.19 mmol, yield=95%). HRMS (+ESI) m/z m/z calcd. for $C_{48}H_{65}EuF_3N_9O_4$ $[M-H]^{2+}$ m/z=1041.4324/2=520.7162, found 520.7186. (FIG. 9); HPLC characterization: Retention time=15.36 min. (Table 1 and FIGS. 7A-7B). The chemical structure of HGEu002 can be represented by the formula (II), wherein X is $CF_3$; Ln is Eu.

TABLE 1

Solvent gradient of HPLC for the characterization of HGEu001 and HGEu002.

| Time/min | 0.05% TFA in water/% | 0.05% TFA in $CH_3CN$/% |
|---|---|---|
| 0.0 | 90 | 10 |
| 5 | 90 | 10 |
| 15 | 40 | 60 |
| 20 | 90 | 10 |
| 25 | 90 | 10 |

Flow rate = 1 mL/min

Photophysical Studies

UV-Visible absorption spectra in the spectral range 200 to 1100 nm were recorded by an HP Agilent UV-8453 Spectrophotometer. The emission spectra and the emission decay lifetimes of HGEu001 and HGEu002 were measured by Horiba Fluorolog-3 spectrophotometer and also measured by Edinburgh instrument FLS920 spectrophotometer for cross checking. (Two spectrophotometers are equipped with a 450 W continuous xenon lamp for steady state emission measurement, 60 W xenon flashlamp for emission life time measurement and an UV-Vis PMT detector—Hamamatsu-R928 cooled 216 at −20° C.)

Stability Test Via Europium Emission Titration

Kinetic stability of the europium complexes were conducted to investigate the stability of the complexes in the diluted solution and in the present of 100 times of $[EDTA]^{2-}$ and $Ca^{2+}$. EDTA was chose as a competitive ligand for the $Eu^{3+}$ ion. $Ca^{2+}$ cation serves as competitive ions for the ligand which can bind to the cyclen based macrocyclic ligand. 10 μM of europium complex was co-incubated 1 mM of EDTA or $Ca^{2+}$ at room temperature, and the europium emission spectra were measured at different time point (1, 24 and 48 hours).

Materials

Tissue Culture

Human cervical cancer HeLa cells were grown in Dulbecco's Modified Eagle Medium (DMEM). Human lung normal diploid fibroblasts MRC-5 and neuroblastoma cells SK-N-SH were provided by Cell resource center of Shanghai Institute of Biological Sciences, Chinese Academy of Sciences; and cultured in MEM (GIBCO 41500034); Human derived liver cells QSG-7701 cells were grown in RPMI-1640 (GIBCO 31800022); all cells were supplemented with 10% (v/v) fetal bovine serum, 1% penicillin and streptomycin at 37° C. and 5% $CO_2$.

MTT Cell Cytotoxicity Assays

HeLa, SK-N-SH, QSG-7701 or MRC-5 cells treated with testing complexes for 24 hours were further incubated with MTT, 3-(4, 5-dimethylthiazol-2-yl)-2 and 5-diphenyltetrazolium bromide (0.5 mg/ml) for 4 hours, to produce formazan during cell metabolism. Then, formazan was thoroughly dissolved by dimethyl sulfoxide (DMSO), and the absorbance of solutions was measured in Bio-Rad iMark microplate reader (570 nm). Quadruplicates were performed. Data analysis and plotting were operated by the GraphPad Prism 5 software.

Two-Photon Confocal In Vitro Imaging

Cells were seeded on coverslip in 35-mm culture dishes overnight. And then incubated with HGEu001 or HGEu002 (10 µM) for 6 hours, and the cells were washed by PBS 3 times before imaging. For the two-photon time lapses in vitro images of HGEu001 and HGEu002 were observed with different incubation time (3, 6, 18 and 24 hours). Then the unabsorbed complexes were washed out with PBS buffer and the cells were subject to microscopic imaging. The in vitro imaging of HGEu001 and HGEu002 were undertaken on a linear fluorescence microscopy under 375 nm UV light excitation or a confocal laser scanning microscope, Leica TCS SP8, equipped with a Ti:sapphire laser (Libra II, coherent). The excitation beam produced by 690 nm to 1080 nm (fs laser) was focused on the adherent cells through a 63× oil immersion objective.

3D images obtained by the Z-stacks form the two-photon confocal microscopy and the 3D reconstruction was done with built-in programs of Leica TCS SP8 confocal microscope.

Co-Localization Imaging (a) 3D Co-Localization Imaging of HGEu001 and HGEu002 with Primary Cilia Markers ARTL13B and IFT88.

Full length ARTL13B (ADP-ribosylation factor-like protein 13B) was PCR amplified from cDNA library and inserted into multiple cloning sites (MCS) of pEGFP-C3 (CLONETECH, #6082-1) using restriction digestion sites of XhoI/EcoRI for GFP-ARTL13B expression. The positive recombinant was selected through kanamycin proved by sequencing. Plasmid mEmerald-IFT88-N-18 (intraflagellar transport protein 88 homolog) expressing GFP-IFT88 was a gift from Michael Davidson (Addgene plasmid #54125). Plasmids were amplified in E. coli (DH5α) and purified using a StarPrep Plasmid Miniprep Kit (Genstar). Both GFP-ARL13B and GFP-ITF88 for primary cilium tracking were expressed in HeLa cells through lipofectamine2000 (Cat. No. 11668-019, Invitrogen) mediated transfection. Briefly, a 3.5 cm dish of HeLa cells (with 70-80% confluent) was transfected with 4 µg DNA plus 4 µL lipofectamine2000 mixture according to the manufacturer instructions. After incubation for 8 hours, 10 µM of HGEu001 or HGEu002 were added and incubated for 6 hours.

(b) Co-Localization Imaging of HGEu001 and HGEu002 with Organelles.

Live cell labeling probes of organelles (mitochondria, lysosome and Golgi apparatus) MitoTracker® Green FM (M-7514), LysoTracker® Green DND-26 (L-7526) and GolgiTracker® Oregon Green (W6748, Wheat Germ Agglutinin) were respectively purchased from ThermoFisher Scientic Inc. and stocked in −20° C.

Three dishes of HeLa cells ($1 \times 10^5$) were first incubated with 10 µM HGEu001/HGEu002 for 6 hours. Then organelles probes (50 nM, each) were added in parallel to the cells and further incubated for 15 minutes. The cells were washed by PBS 3 times before imaging on the linear fluorescence microscopy. Under the excitation of UV light (375 nm) emission from the channel (610-630 nm) were collected for the emission signals from HGEu001/HGEu002. Under 488 nm blue light excitation, imaging channel in the range between 505 and 555 nm were collected from the emission signal of organelles dyes.

Results

Figure 10:
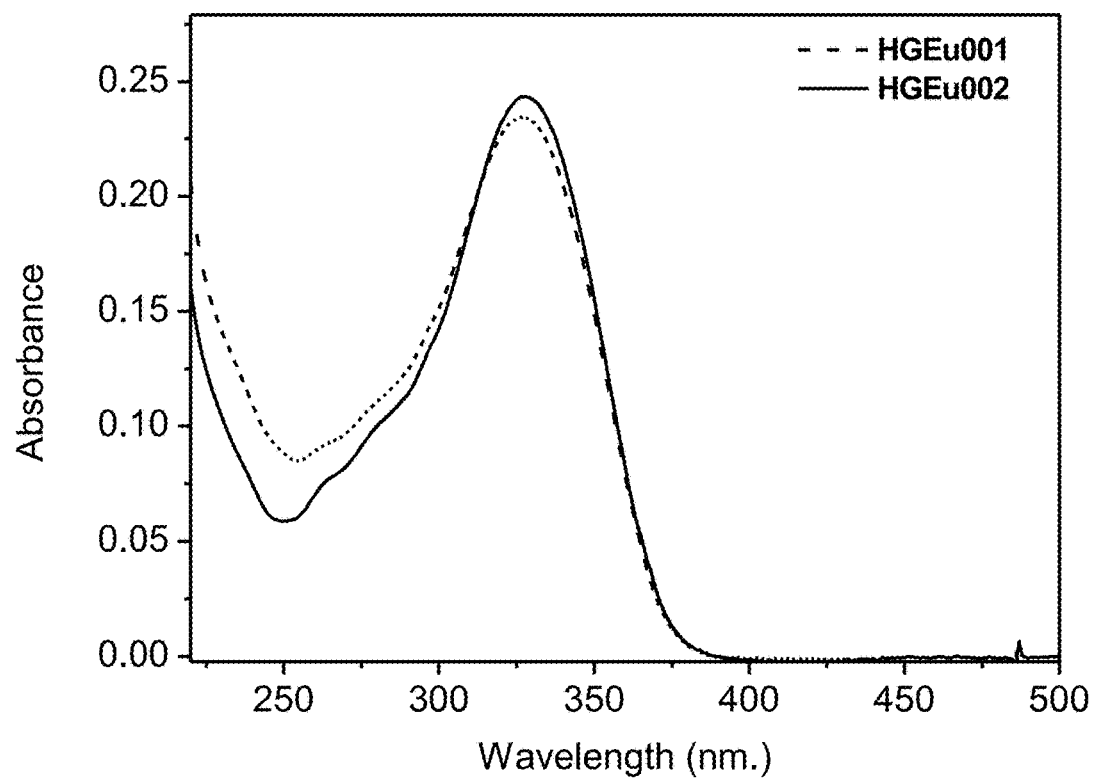
FIG. 10 shows the absorption spectra of HGEu001 and HGEu002 in aqueous solution (10 μM).
Figure 11A:
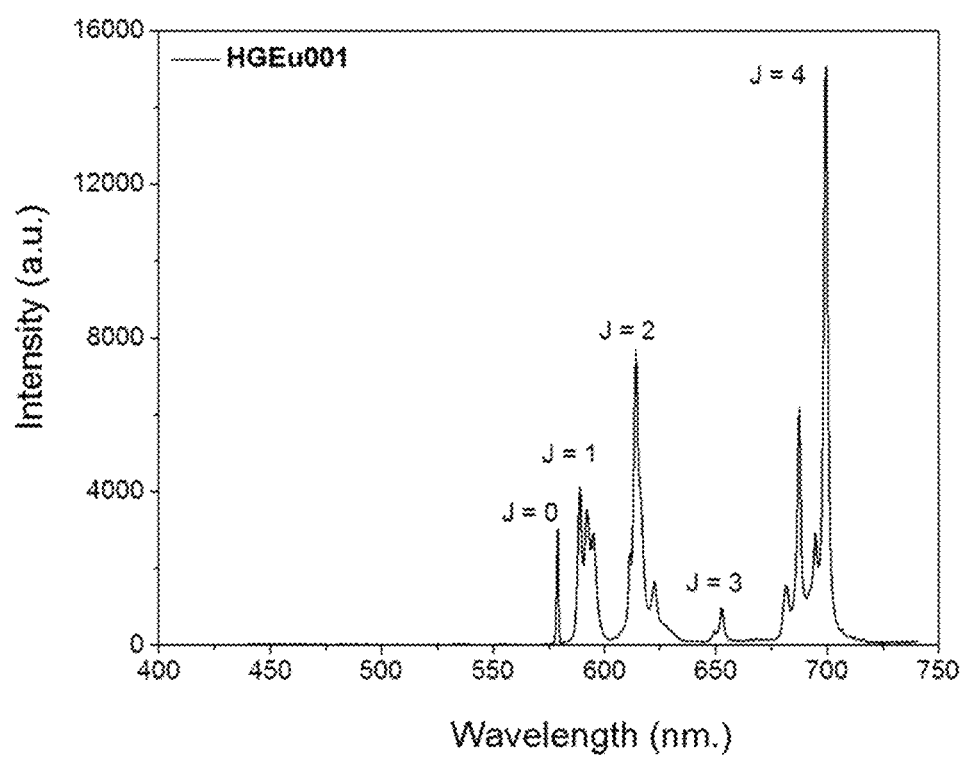
FIG. 11A shows the emission spectra of HGEu001 aqueous solution (10 μM, $\lambda_{ex}$=340 nm). The spectra were recorded on Horiba Flurolog-3 spectrophotometer. The same emission bands and ratios obtained are compared with the emission spectra measured with Edinburgh instrument FLS920 spectrophotometer as in FIGS. 1A-1B.
Figure 11B:
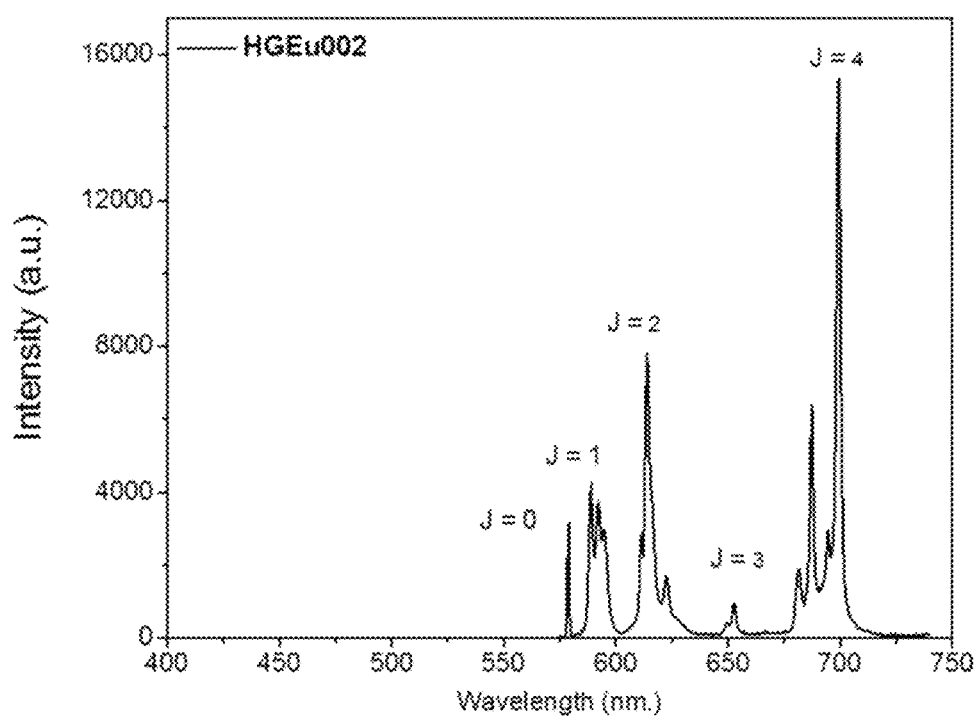
FIG. 11B shows the emission spectra of HGEu002 aqueous solution (10 μM, $\lambda_{ex}$=340 nm). The spectra were recorded on Horiba Flurolog-3 spectrophotometer. The same emission bands and ratios obtained are compared with the emission spectra measured with Edinburgh instrument FLS920 spectrophotometer as in FIGS. 1A-1B.

Two europium complexes HGEu001 and HGEu002 were synthesized by similar procedures as shown in Scheme 1 (FIG. 29). Recrystallization of the crude europium complexes with diethyl ether gave HGEu001 and HGEu002 in a yield of ~95%. All the intermediates were well characterized by $^1$H-NMR, $^{13}$C-NMR and HRMS. The europium complexes, HGEu001 and HGEu002, were purified and verified by high-performance liquid chromatography and HRMS (FIGS. 7A-7B, 8-9). The strong absorption bands of the complex HGEu001 in water can be found peaking at 340 nm ($\varepsilon$>20,000 cm$^{-1}$, Table 2), corresponding to the $\pi \rightarrow \pi^*$ transition (FIG. 10).

The photo-physical properties of HGEu001 and HGEu002 were recorded in aqueous solution and have similar europium emission quantum yields ($\phi$=~10%). The five europium f-f emission $^5D_j \rightarrow ^7F_J$ bands (J=0-4) were observed and the ratio of these f-f transition intensity is consistent with literature reports of a typical cyclen-based europium complexes with a D2h symmetry (FIGS. 1A-1B, FIGS. 11A-11B and Table 2). Showing similar molecular structures and photo-physical properties, the toxicity of HGEu001 and HGEu002 is also similarly low in HeLa, SK-N-SH, QSG-7701 and MRC-5 cells (IC50 are ~390-440 µM, Table 3). However, the in vitro subcellular localization of HGEu001 and HGEu002 is vastly different, especially HGEu001—the red emission of HGEu001 in vitro did not correlate with common commercial organelle-specific markers, such as mitochondria, lysosome and Golgi apparatus in fluorescence microscopy (FIGS. 2A-2I).

TABLE 2

Photophysical properties of the europium complexes HGEu001 and HGEu002.

| Complex | $\lambda_{max}$/nm [a] | $\varepsilon$/M$^{-1}$ cm$^{-1}$ [a] | $\tau$(H$_2$O)/ms [b] | $\tau$(D$_2$O)/ms [b] | q[c] | $\Phi_L^{Eu}$/% [d] |
|---|---|---|---|---|---|---|
| HGEu001 | 327 | 23400 | 0.56 | 1.78 | 0.9 | 10.5 |
| HGEu002 | 327 | 22200 | 0.56 | 1.78 | 0.9 | 10.3 |

Figure 12A:
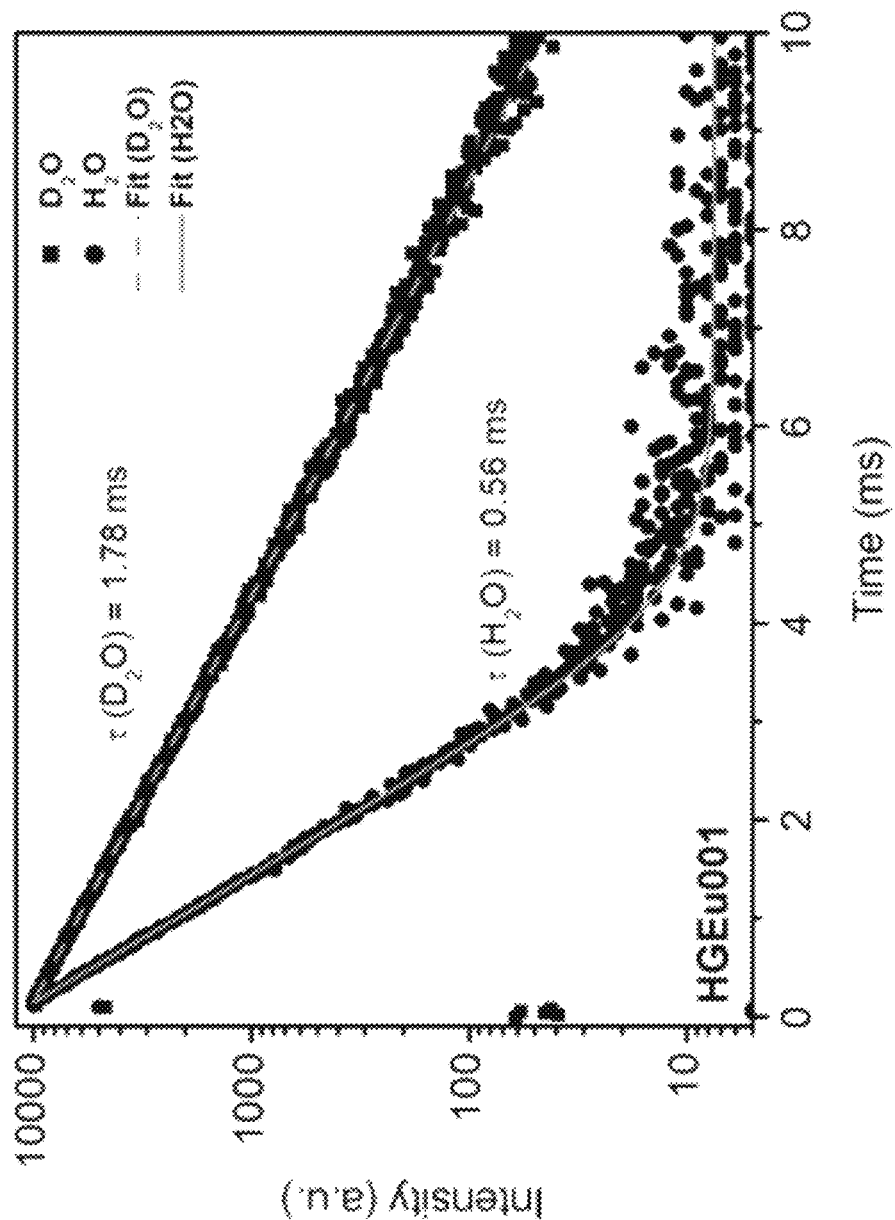
FIG. 12A shows the emission decay curve of the complex HGEu001 and in D$_2$O and H$_2$O. ($\lambda_{em}$=614 nm. $^5D_0 \rightarrow {}^7F_2$. $\lambda_{ex}$=355 nm).
Figure 12B:
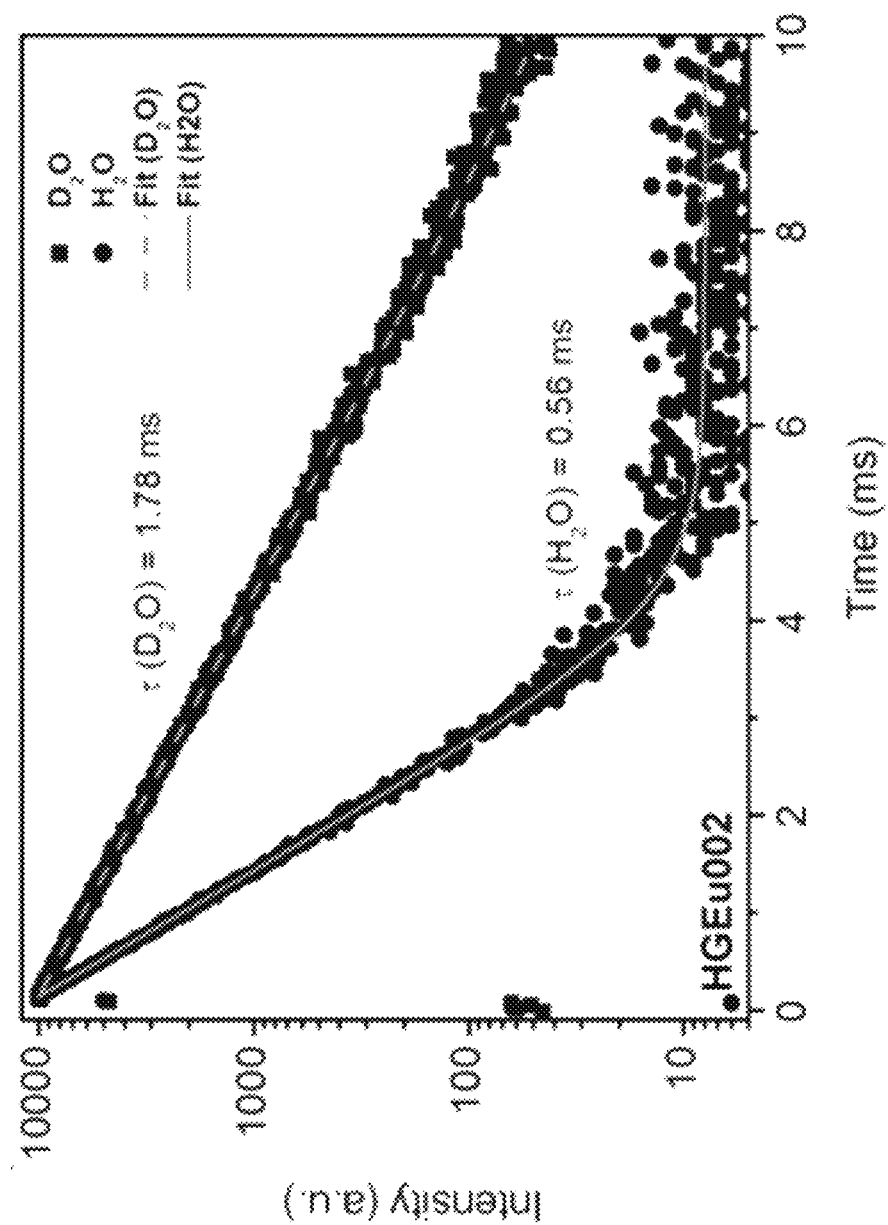
FIG. 12B shows the emission decay curve of the complex HGEu002 in D$_2$O and H$_2$O. ($\lambda_{em}$=614 nm. $^5D_0 \rightarrow {}^7F_2$. $\lambda_{ex}$=355 nm).

[a] Absorption coefficient in H$_2$O, 298 K;
[b] Europium emission decay in FIGS. 12A-12B ($\lambda_{em}$ = 614 nm. $^5D_0 \rightarrow ^7F_2$. $\lambda_{ex}$ = 340 nm);
[c]Derived hydration numbers, q (±20%) q = 1.2[(k(H$_2$O) k(D$_2$O)) − (0.25 + 0.07x)] (k = $\tau^{-1}$, x = number of carbonyl-bound amide NH oscillators);
[d] Overall europium emission quantum yield in H$_2$O, by integrated sphere.

TABLE 3

Cytotoxicity of the complexes HGEu001 and HGEu002 against HeLa, SK-N-SH, QSG-7701 and MRC-5 cell line. (IC$_{50}$/µM)

| Complex | HeLa | SK-N-SH | QSG-7701 | MRC-5 |
|---|---|---|---|---|
| HGEu001 | 411 | 389 | 395 | 395 |
| HGEu002 | 417 | 437 | 410 | 402 |

Figure 13A:
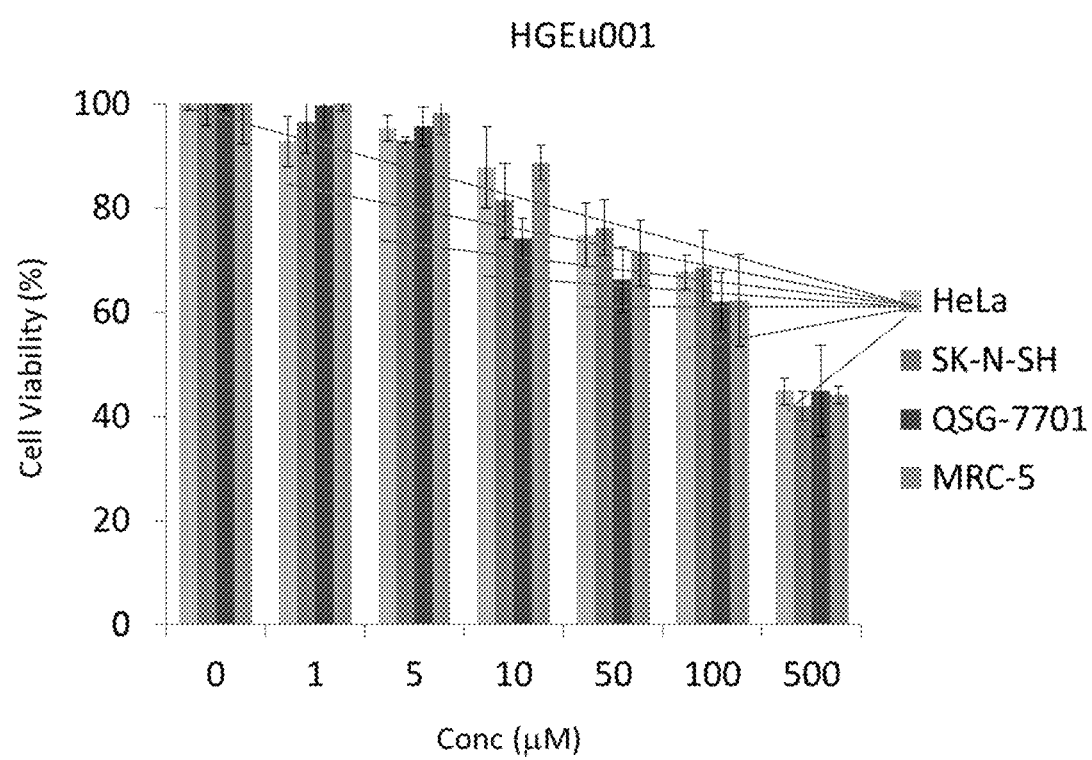
FIG. 13A shows the raw data of cytotoxicity of HGEu001 in Table 3.
Figure 13B:
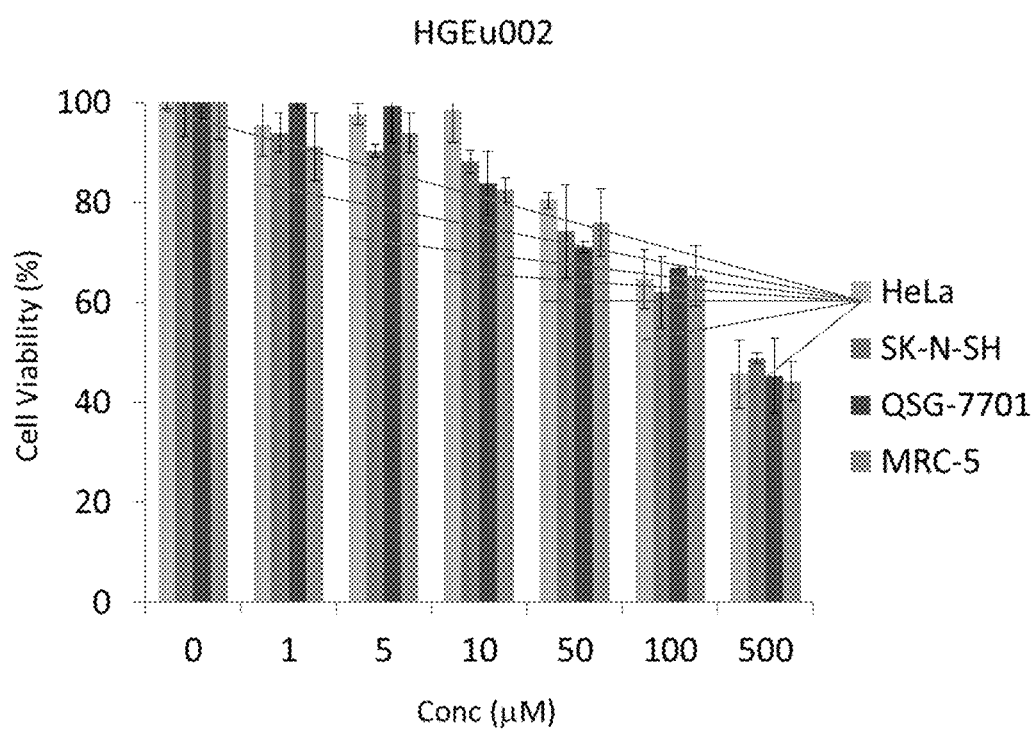
FIG. 13B shows the raw data of cytotoxicity of HGEu002 in Table 3.
Figure 14A:
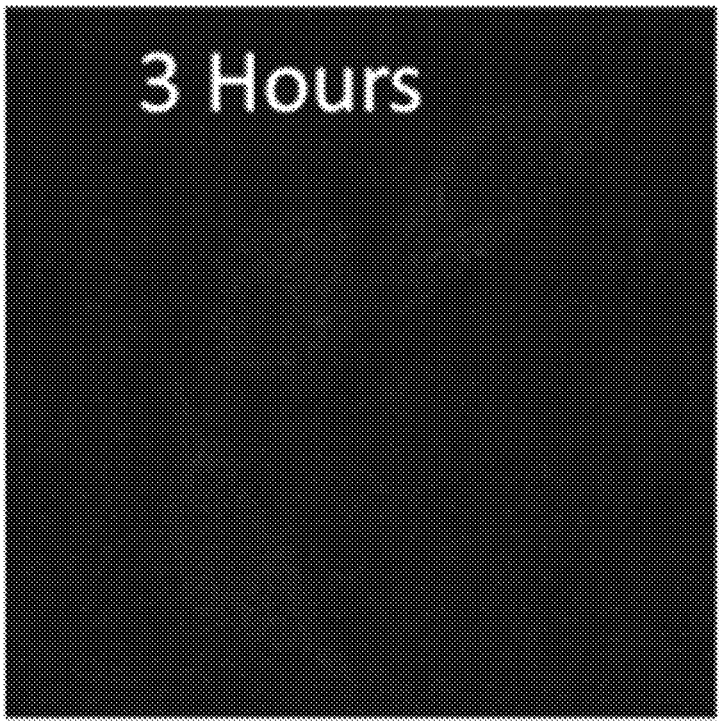
FIG. 14A shows the two-photon time lapses in vitro images of HGEu002 in HeLa cells which the images were taken at 3 hours incubation time points; The red emission of HGEu002 is localized in cytoplasm. (In parallel with FIG. 3A).
Figure 14B:
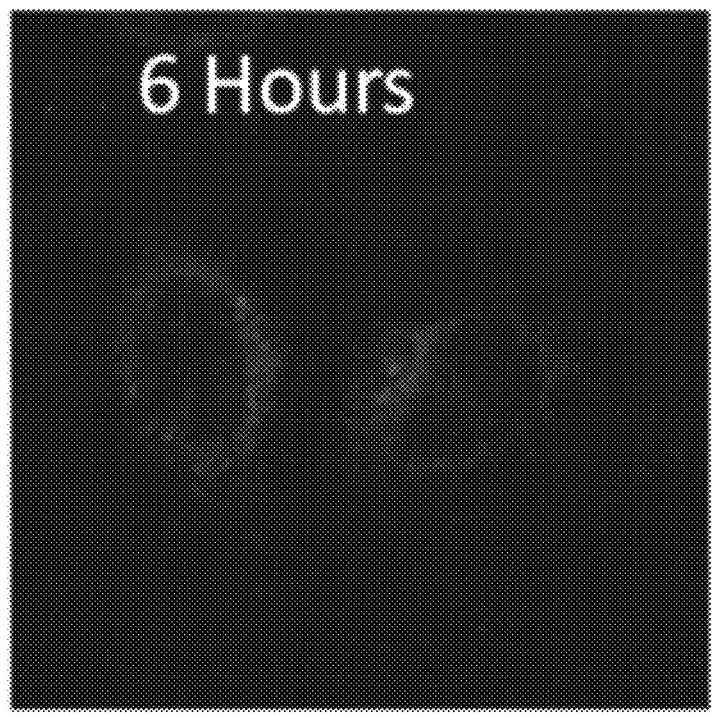
FIG. 14B shows the two-photon time lapses in vitro images of HGEu002 in HeLa cells which the images were taken at 6 hours incubation time points; The red emission of HGEu002 is localized in cytoplasm. (In parallel with FIG. 3B).
Figure 14C:
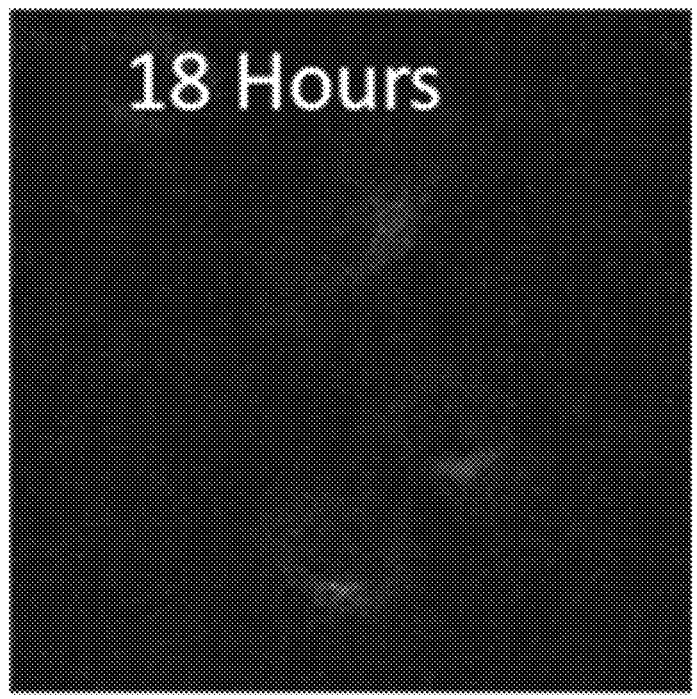
FIG. 14C shows the two-photon time lapses in vitro images of HGEu002 in HeLa cells which the images were taken at 18 hours incubation time points; The red emission of HGEu002 is localized in cytoplasm. (In parallel with FIG. 3C).
Figure 14D:
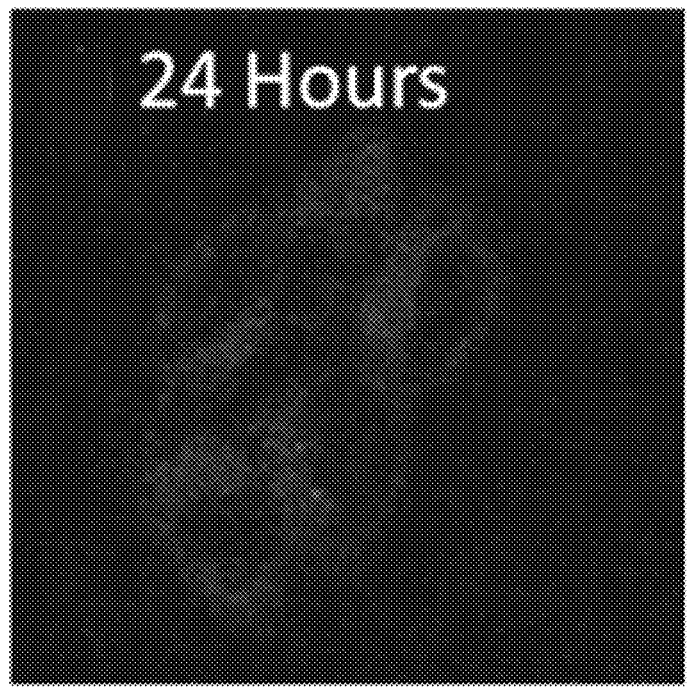
FIG. 14D shows the two-photon time lapses in vitro images of HGEu002 in HeLa cells which the images were taken at 24 hours incubation time points; The red emission of HGEu002 is localized in cytoplasm. (In parallel with FIG. 3D).
Figure 14E:
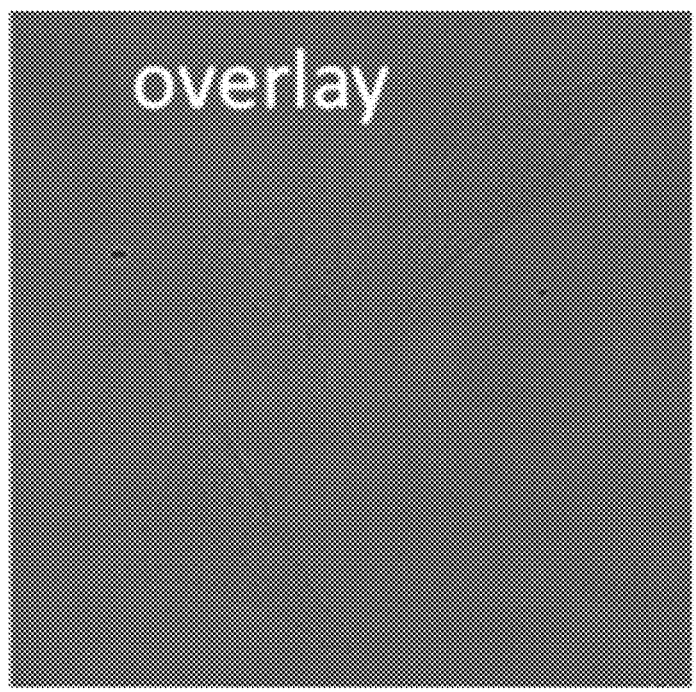
FIG. 14E shows the overlay images of fluorescence channel shown in FIG. 14A and bright field channel (Dosed concentration=10 μM, $\lambda_{ex}$=700 nm, filter Bandpass=550-665 nm); The red emission of HGEu002 is localized in cytoplasm. (In parallel with FIG. 3E).
Figure 14F:
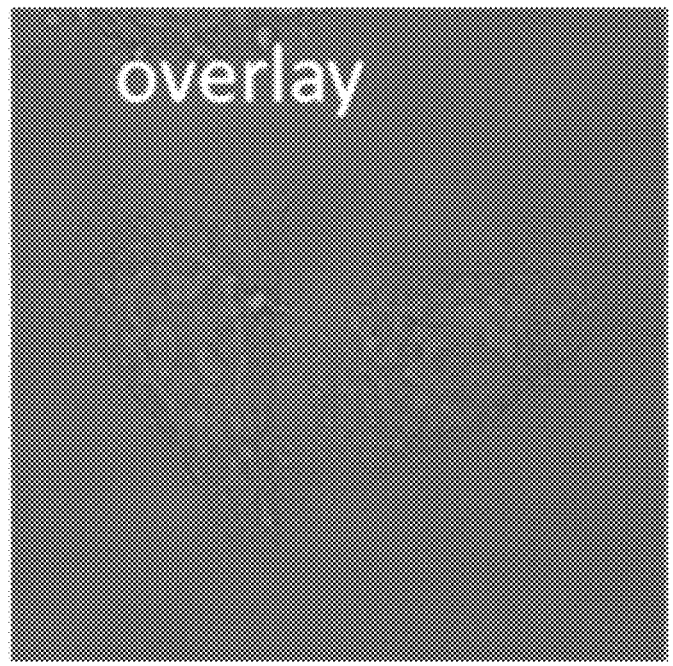
FIG. 14F shows the overlay images of fluorescence channel shown in FIG. 14B and bright field channel (Dosed concentration=10 μM, $\lambda_{ex}$=700 nm, filter Bandpass=550-665 nm); The red emission of HGEu002 is localized in cytoplasm. (In parallel with FIG. 3F).
Figure 14G:
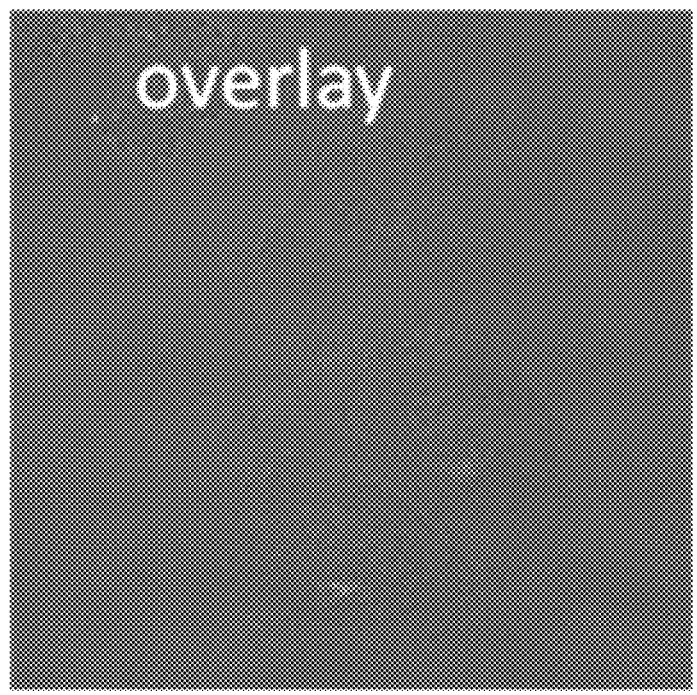
FIG. 14G shows the overlay images of fluorescence channel shown in FIG. 14C and bright field channel (Dosed concentration=10 μM, $\lambda_{ex}$=700 nm, filter Bandpass=550-665 nm); The red emission of HGEu002 is localized in cytoplasm. (In parallel with FIG. 3G).
Figure 14H:
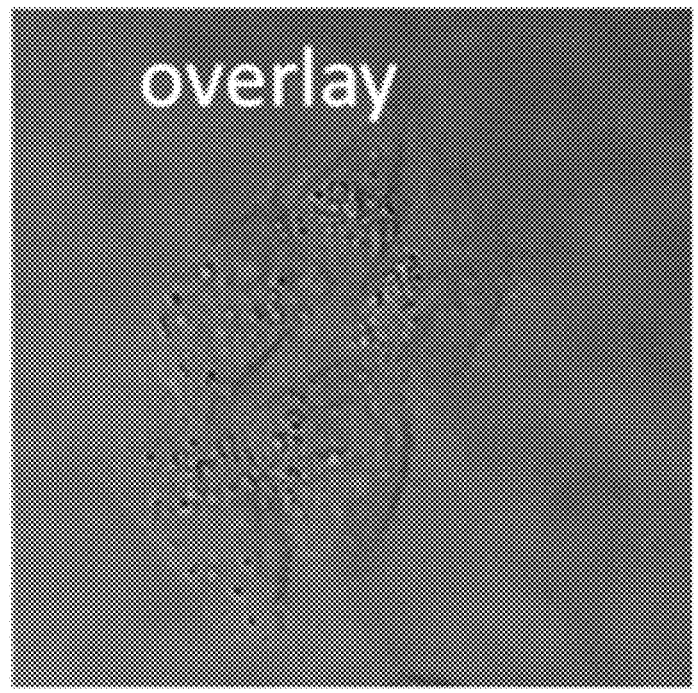
FIG. 14H shows the overlay images of fluorescence channel shown in FIG. 14D and bright field channel (Dosed concentration=10 μM, $\lambda_{ex}$=700 nm, filter Bandpass=550-665 nm); The red emission of HGEu002 is localized in cytoplasm. (In parallel with FIG. 3H).
Figure 15A:
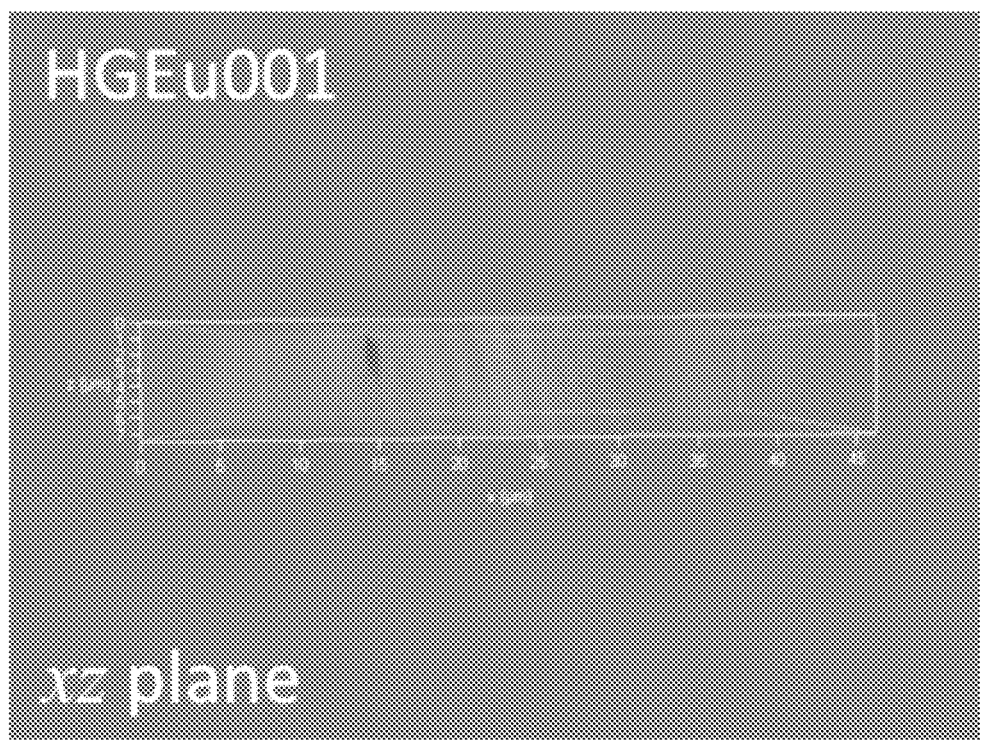
FIG. 15A shows the three dimensional in vitro imaging of 10 μM in xz plan for HGEu001 incubated in MRC-5 cells with 6 hours. ($\lambda_{ex}$=700 nm, In parallel with FIG. 5A).
Figure 15B:
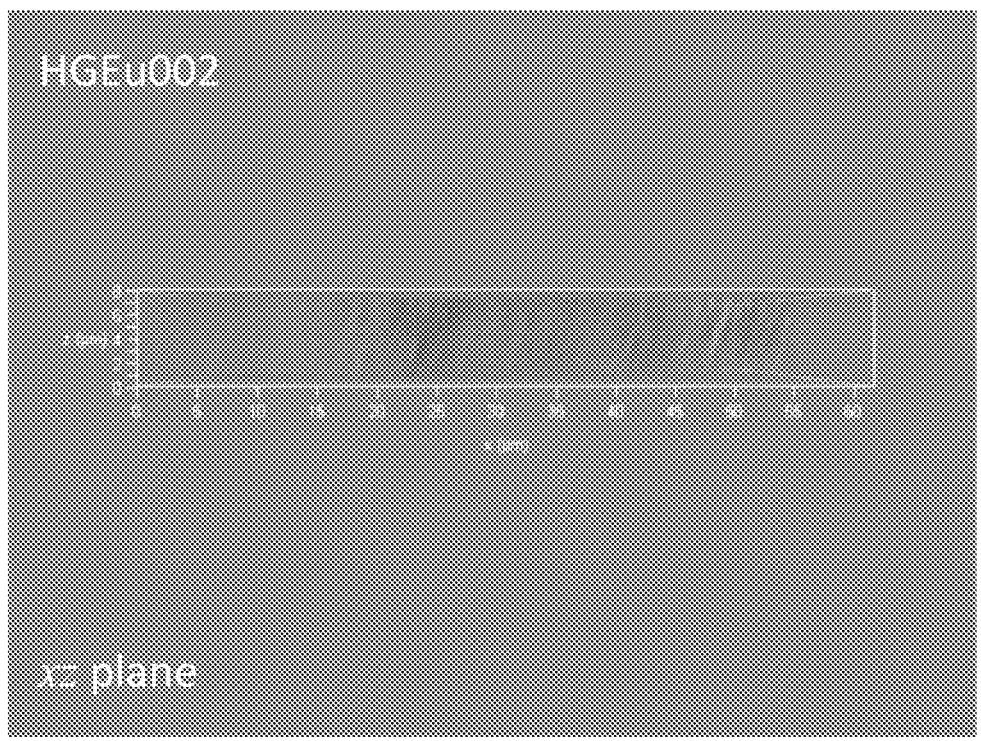
FIG. 15B shows the three dimensional in vitro imaging of 10 μM in xz plan for HGEu002 incubated in MRC-5 cells with 6 hours. ($\lambda_{ex}$=700 nm, In parallel with FIG. 5B).
Figure 15C:
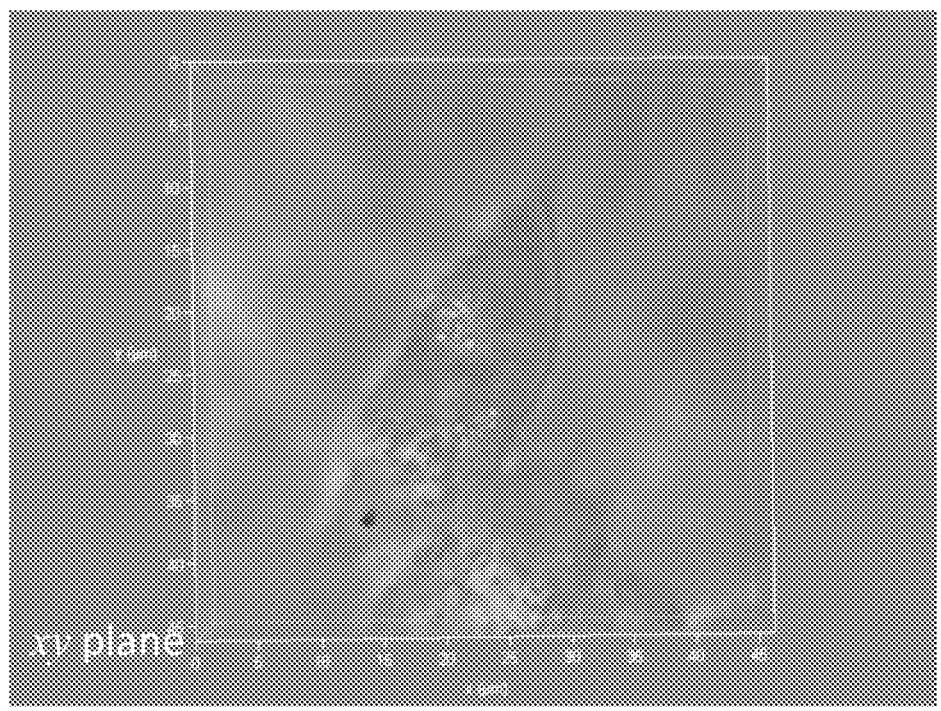
FIG. 15C shows the three dimensional in vitro imaging of 10 μM in xy plan for HGEu001 incubated in MRC-5 cells with 6 hours. ($\lambda_{ex}$=700 nm, In parallel with FIG. 5C).
Figure 15D:
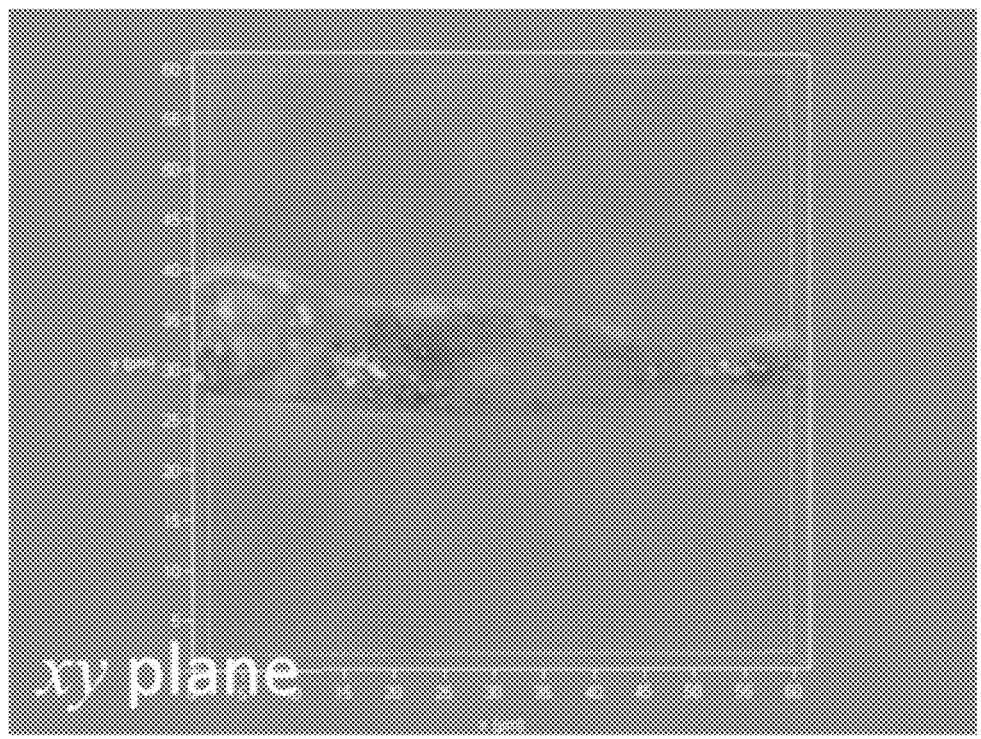
FIG. 15D shows the three dimensional in vitro imaging of 10 μM in xy plan for HGEu002 incubated in MRC-5 cells with 6 hours. ($\lambda_{ex}$=700 nm, In parallel with FIG. 5D).
Figure 15E:
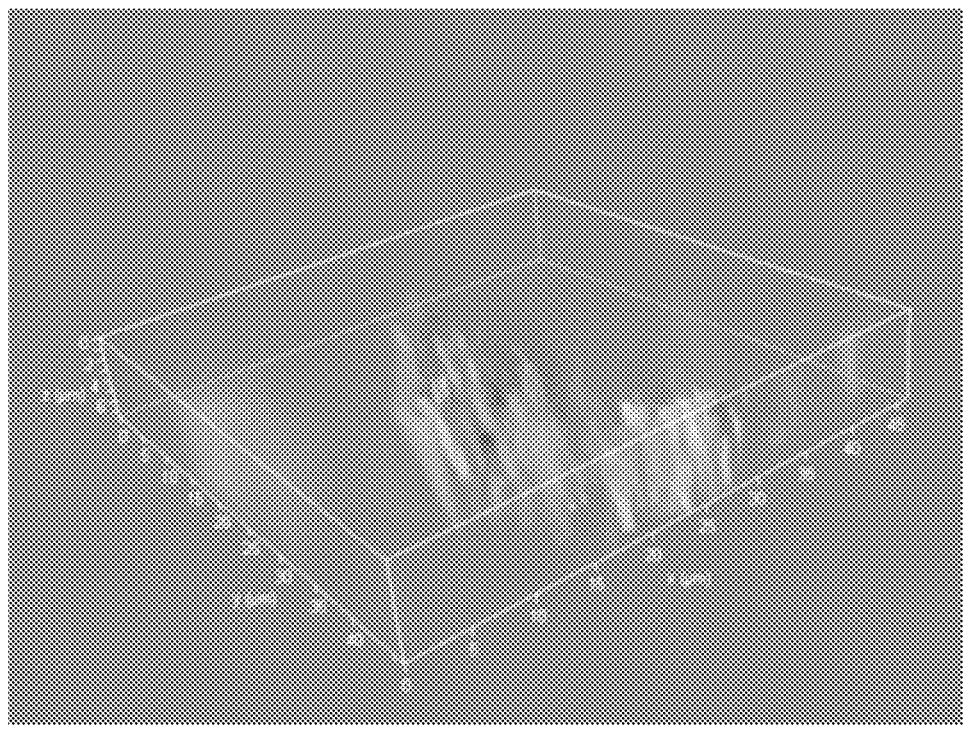
FIG. 15E shows the three dimensional in vitro imaging of 10 μM in xyz plane for HGEu001 incubated in MRC-5 cells with 6 hours. ($\lambda_{ex}$=700 nm, In parallel with FIG. 5E).
Figure 15F:
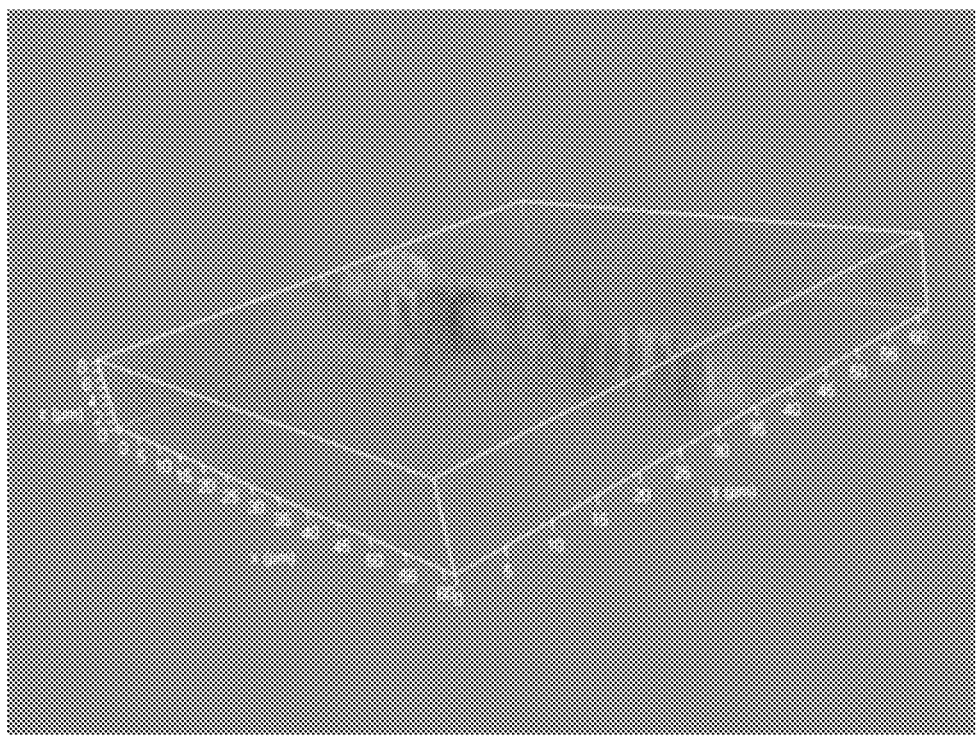
FIG. 15F shows the three dimensional in vitro imaging of 10 μM in xyz plane for HGEu002 incubated in MRC-5 cells with 6 hours. ($\lambda_{ex}$=700 nm, In parallel with FIG. 5F).

Incubation time = 24 hours;
Raw data are shown in FIGS. 13A-13B.

Discussion

To further confirm the reputation of the primary cilia-specific in vitro subcellular localization of HGEu001, in vitro imaging of HGEu001 was performed on a multi-photon confocal microscope (FIGS. 3A-3H). With 3 hours of incubation in HeLa cells, red europium emission of HGEu001 was found in a particularly focused area in the primary cilium under two photon excitation ($\lambda_{ex}$=700 nm, FIGS. 3A-3H) and optimum emission intensity lasted for 24 hours. However, the red emission of HGEu002 was found dispersed in the cytoplasm (FIGS. 14A-14H and 15A-15F). The in vitro subcellular localization of HGEu001 and HGEu002 are the same in number of cell lines, such as HeLa, SK-N-SH and MRC-5 (FIGS. 13A-13B).

Aiming to confirm this subcellular localization of HGEu001, a positive control has been done. The co-localization experiments have been done by Green Fluorescent Protein-fused with primary cilia marker ARL13B (GFP-ARL13B). The advantages of using Green Fluorescent Protein "GFP" are its bright luminescence and availability to trace the localization of cellular proteins, such as antibody, at the targets in vitro. However, GFP also gives scientists a lot of hassle in molecular imaging, such as its complicated process in cloning, transfection and their broad emission profile and short emission lifetime presents a low signal to noise ratio problem. There are no commercially available simple primary cilia markers, therefore, the present invention could only compare the subcellular localization between HGEu001 and GFP-ARL13B (ARL13B is the cilium-specific protein required for culinary axoneme structure) and with HGEu002 as a negative control (FIGS. 2A-2I).

Figure 4A:
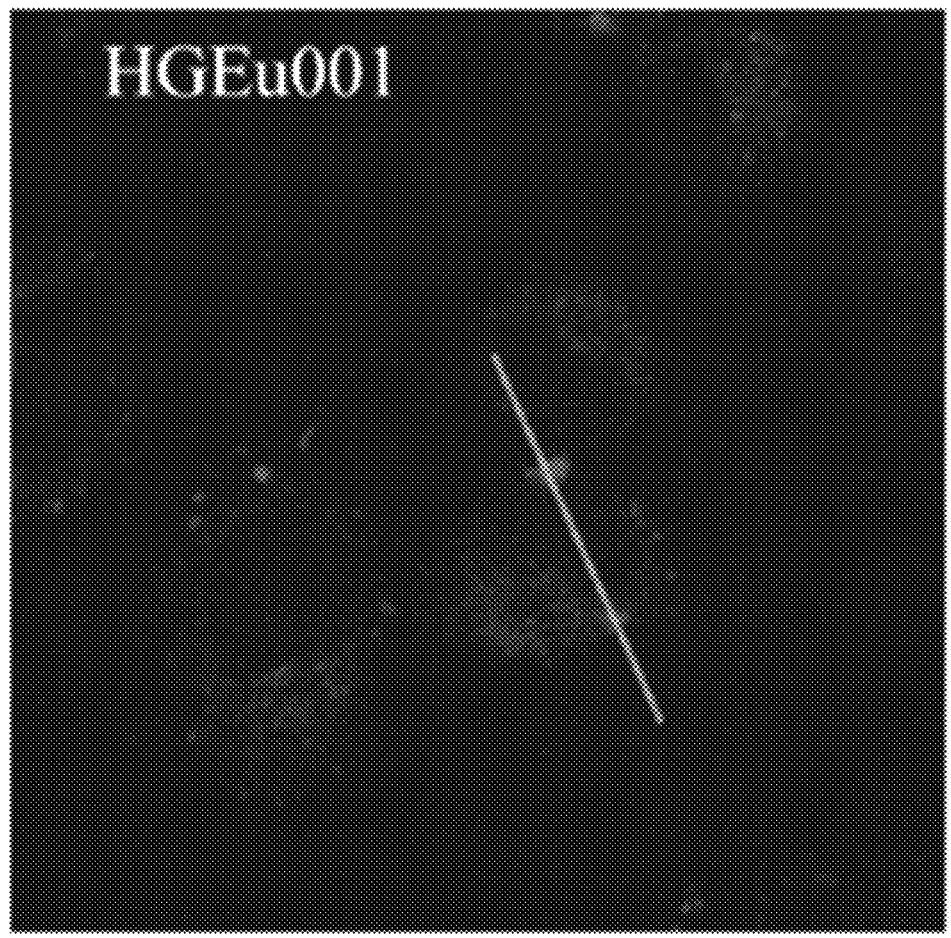
FIG. 4A shows the co-staining experiments of red HGEu001 in fluorescence microscope with marked distance for primary cilium (Green line) (Dosed concentration 10 μM HGEu001, 6 hours incubation after GFP-ARL13B was transfected and expressed).
Figure 4B:
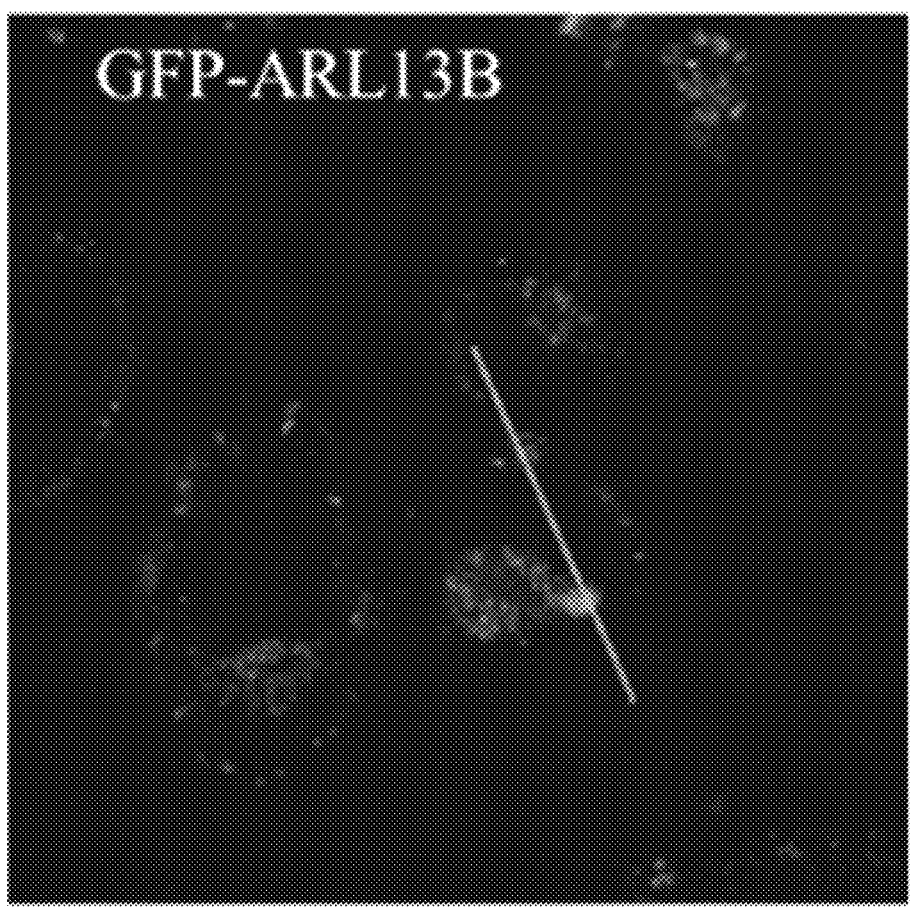
FIG. 4B shows the green GFP-ARL13B in fluorescence microscope with marked distance for primary cilium (Green line).
Figure 4C:
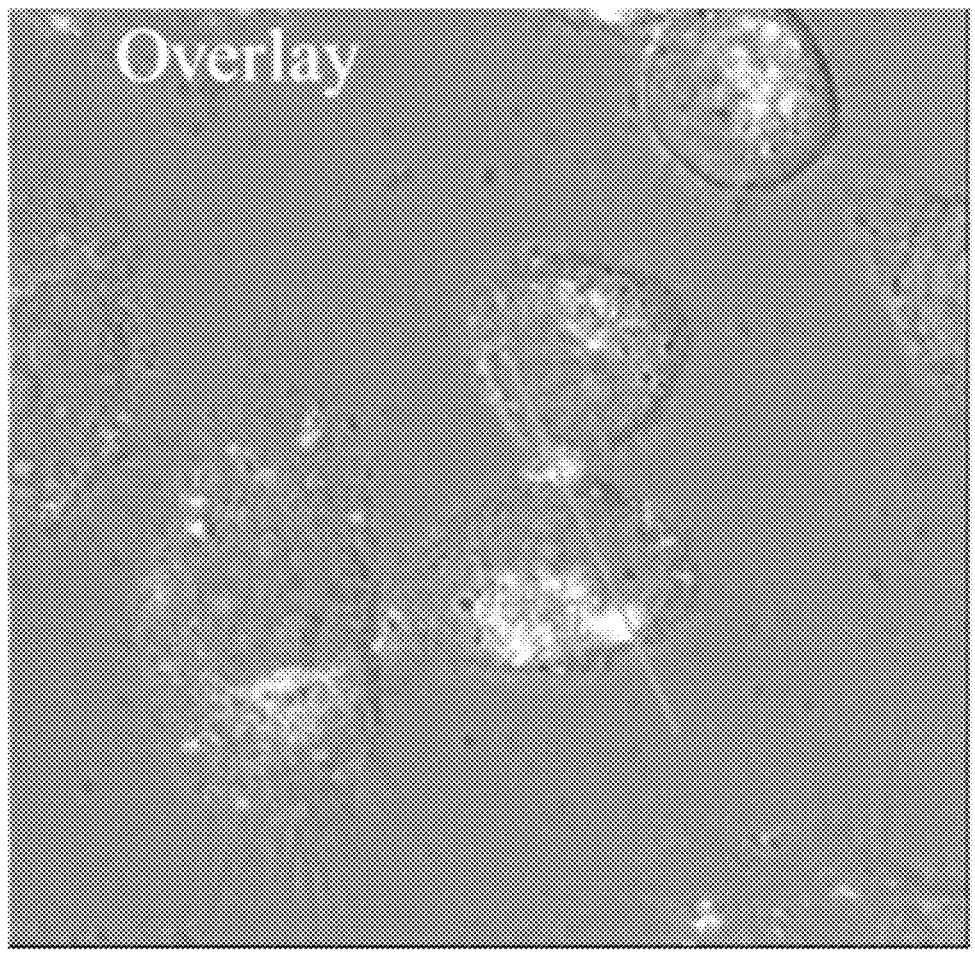
FIG. 4C shows the overlay of FIGS. 4A and 4B in fluorescence microscope with marked distance for primary cilium (Green line).
Figure 4D:
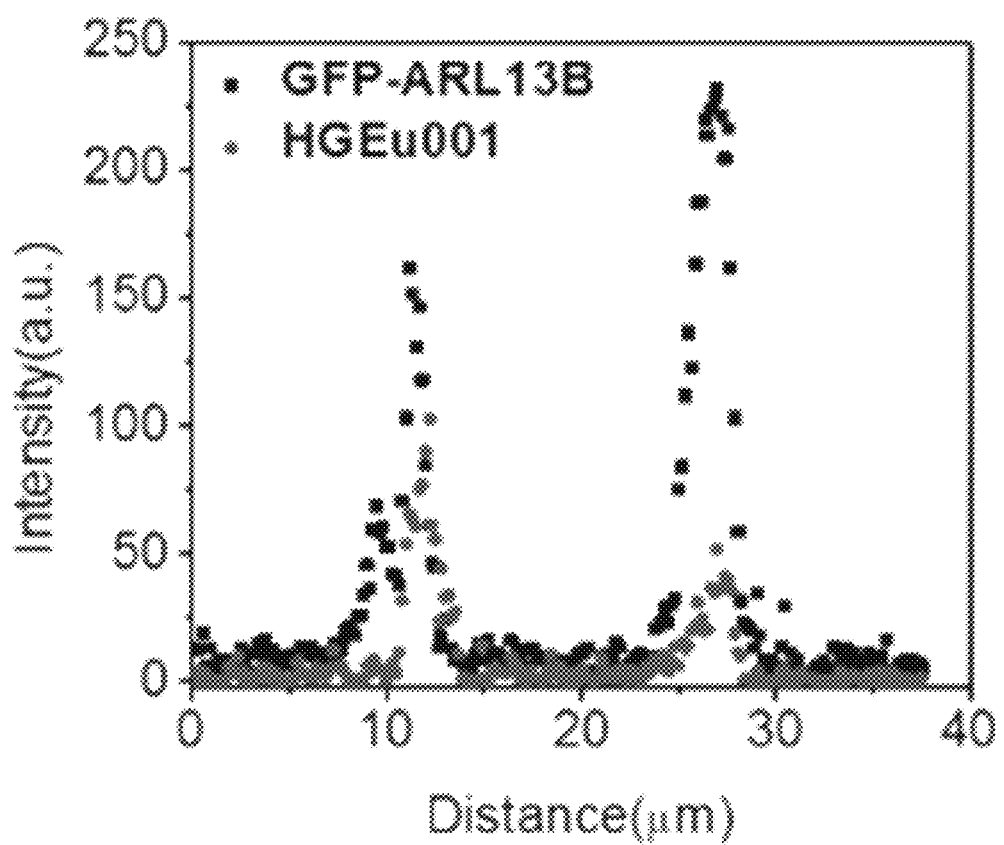
FIG. 4D shows the intensity of HGEu001.
Figure 4E:
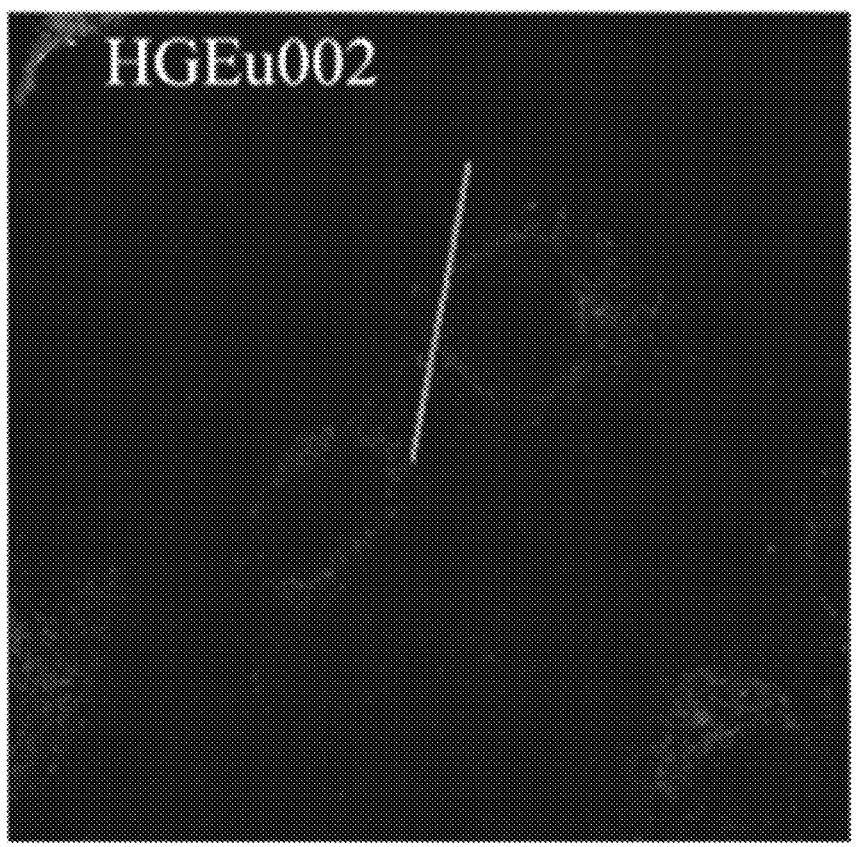
FIG. 4E shows the co-staining experiments of red HGEu002 (control) in fluorescence microscope with marked distance for primary cilium (Green line) (Dosed concentration 10 μM HGEu002, 6 hours incubation after GFP-ARL13B was transfected and expressed).
Figure 4F:
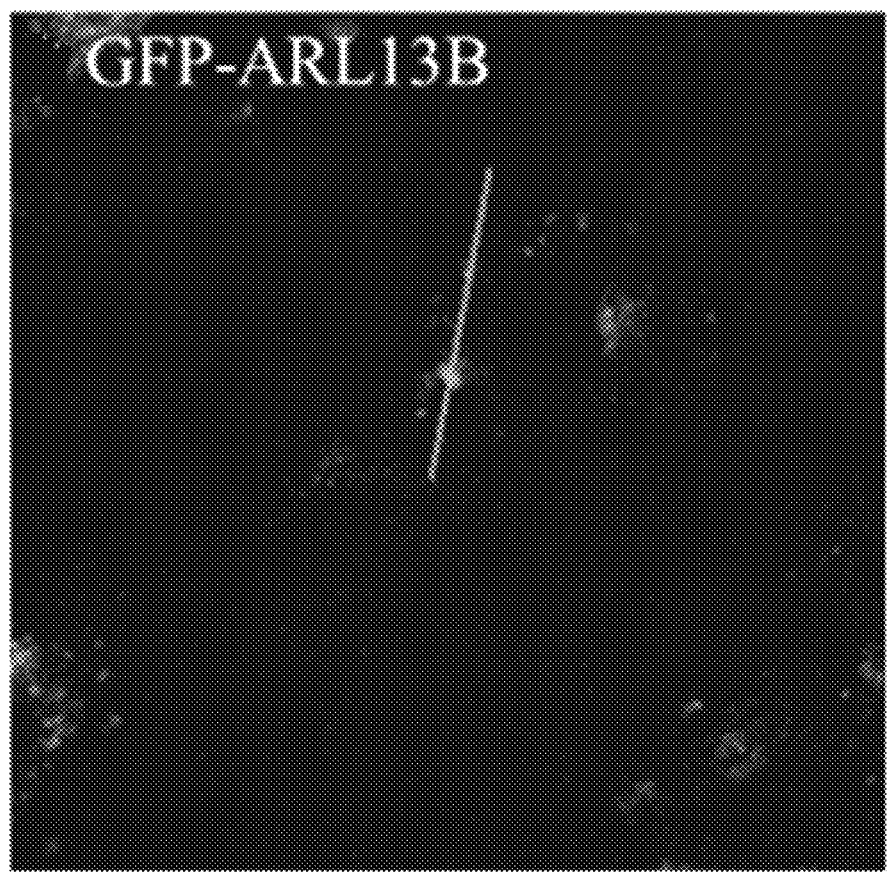
FIG. 4F shows the green GFP-ARL13B in fluorescence microscope with marked distance for primary cilium (Green line).
Figure 4G:
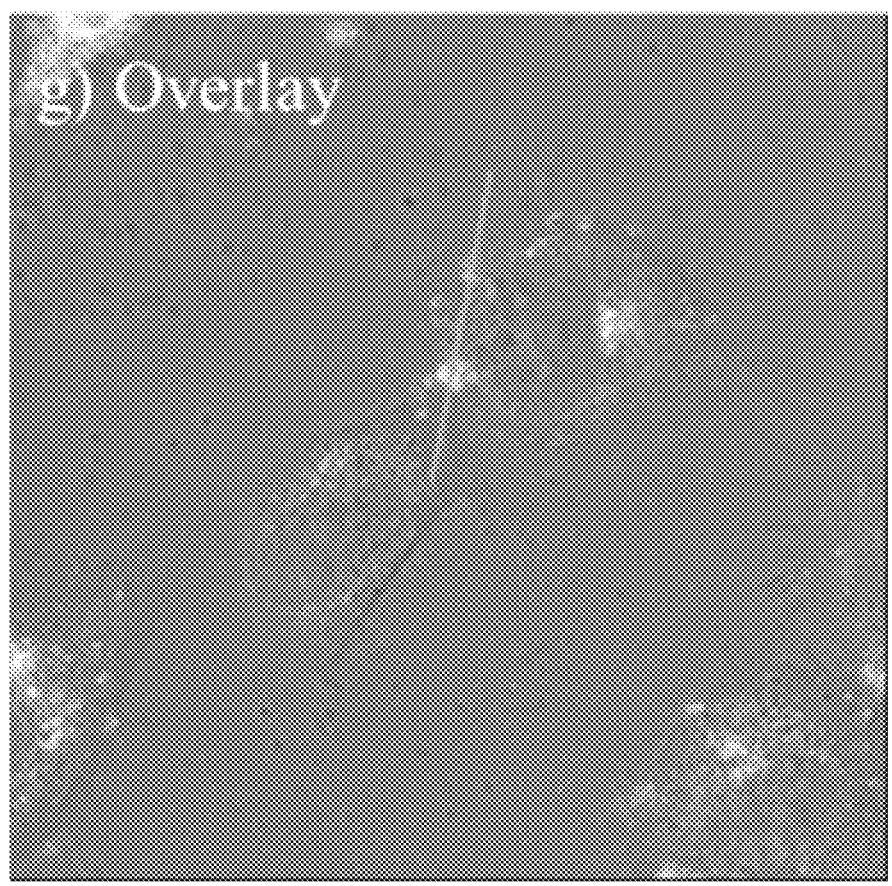
FIG. 4G shows the overlay of FIGS. 4E and 4F in fluorescence microscope with marked distance for primary cilium (Green line).
Figure 4H:
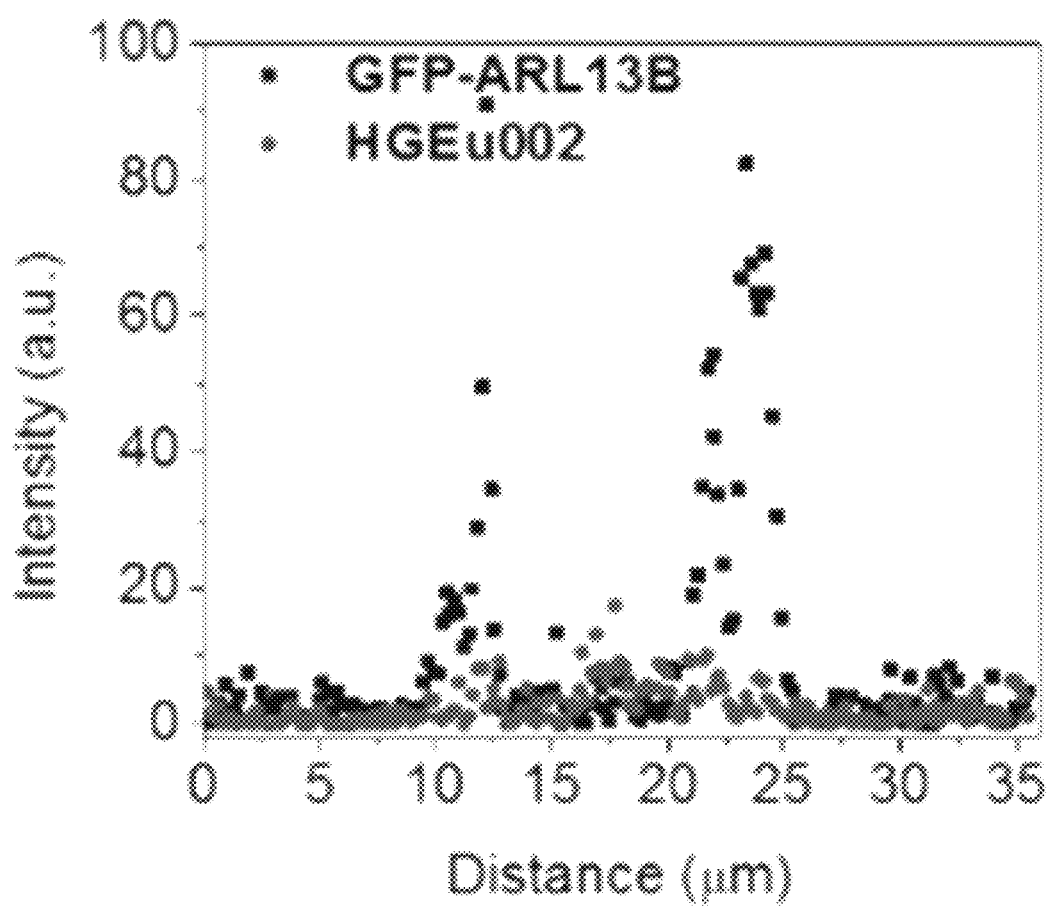
FIG. 4H shows the intensity of HGEu002.
Figure 5A:
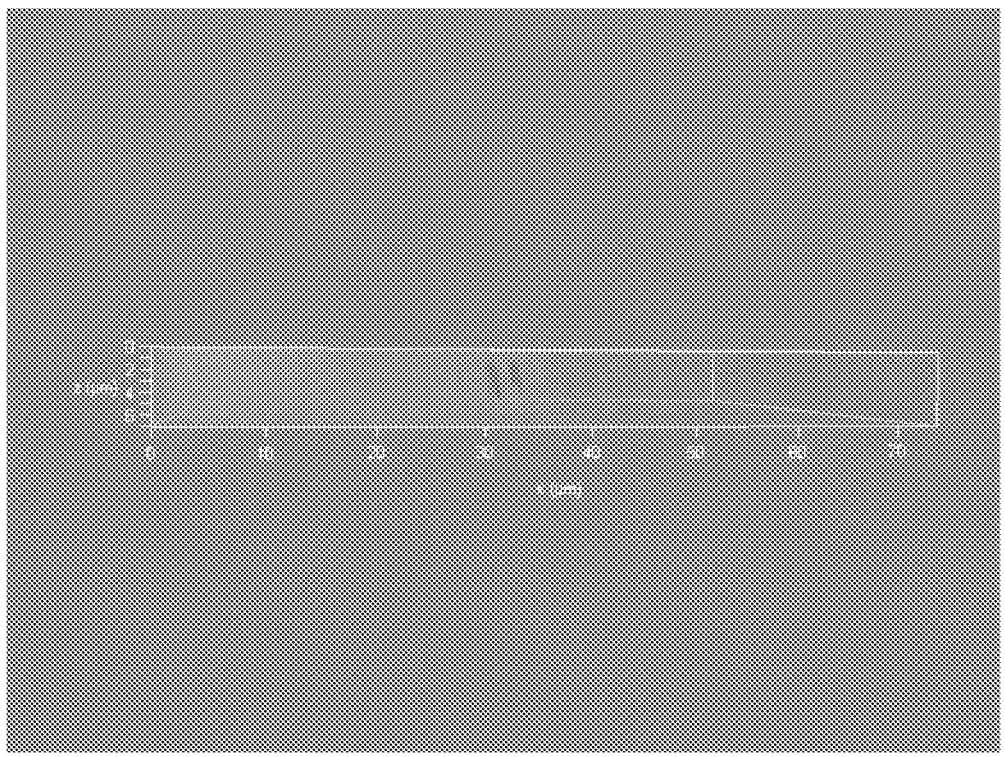
FIG. 5A shows the three dimensional in vitro imaging and emission spectra of 10 μM in xz plane for HGEu001 incubated in HeLa cells for 6 hours. ($\lambda_{ex}$=700 nm).
Figure 5B:
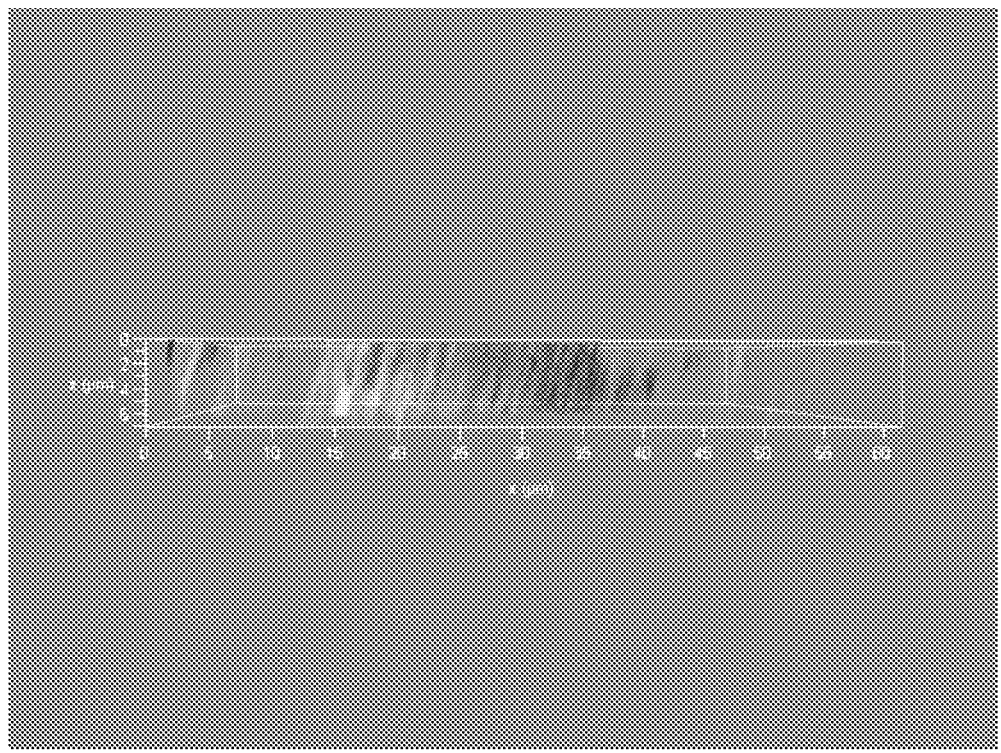
FIG. 5B shows the three dimensional in vitro imaging and emission spectra of 10 μM in xz plane for HGEu002 incubated in HeLa cells for 6 hours. ($\lambda_{ex}$=700 nm).
Figure 5C:
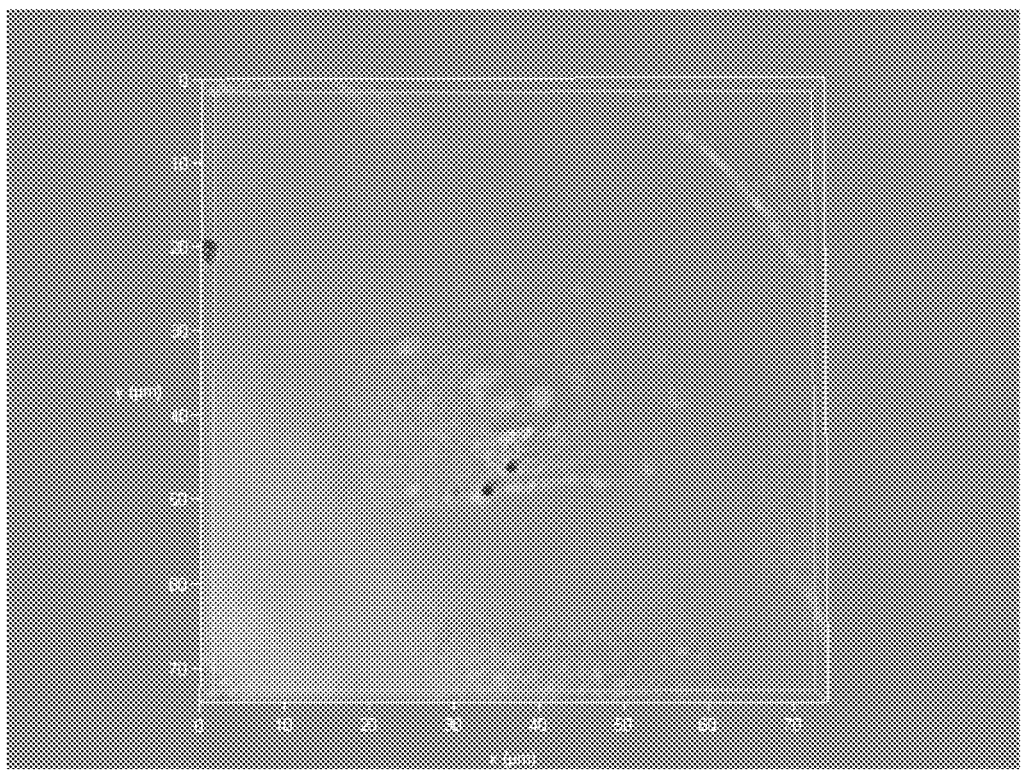
FIG. 5C shows the three dimensional in vitro imaging and emission spectra of 10 μM in xy plane for HGEu001 incubated in HeLa cells for 6 hours. ($\lambda_{ex}$=700 nm).
Figure 5D:
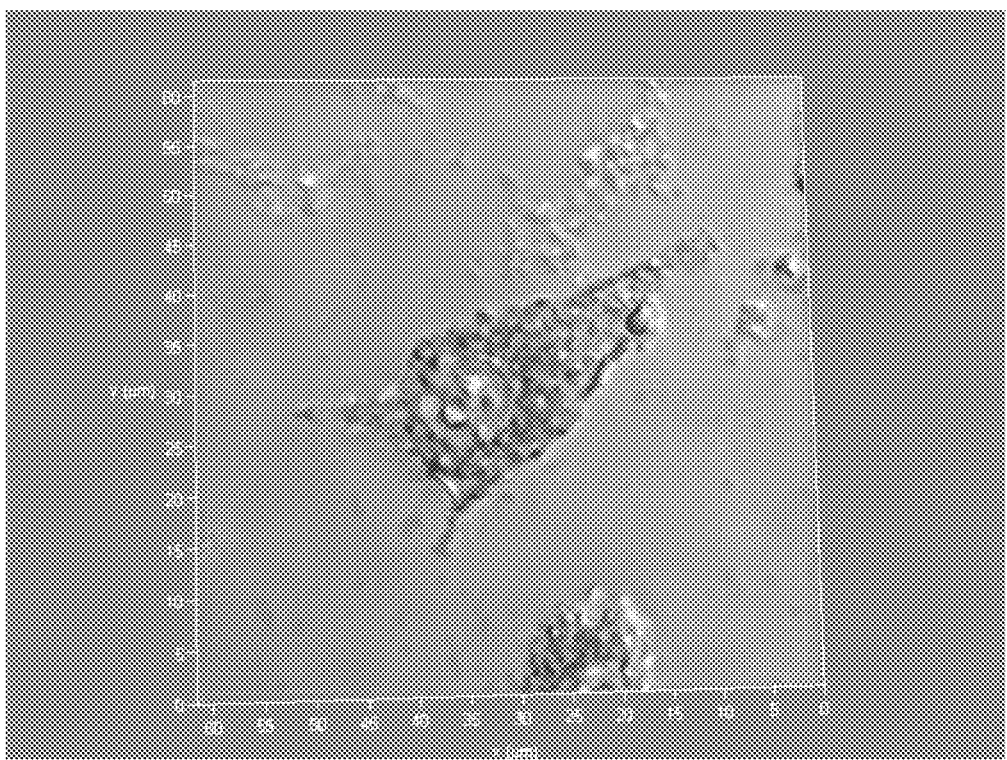
FIG. 5D shows the three dimensional in vitro imaging and emission spectra of 10 μM in xy plane for HGEu002 incubated in HeLa cells for 6 hours. ($\lambda_{ex}$=700 nm).
Figure 5E:
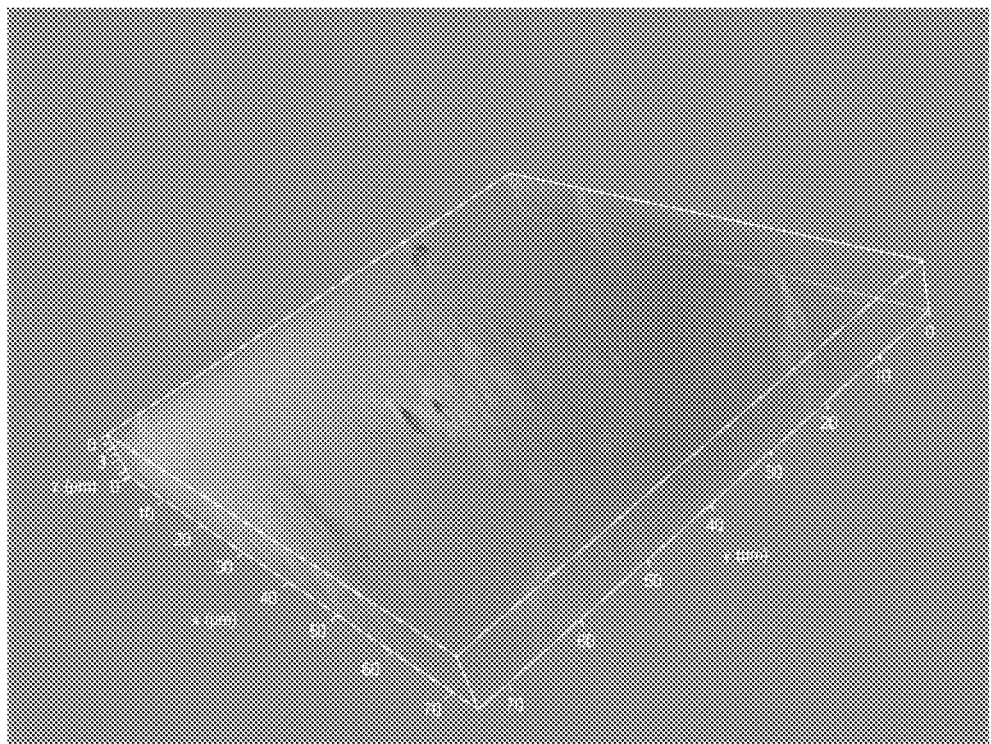
FIG. 5E shows the three dimensional in vitro imaging and emission spectra of 10 μM in xyz plane for HGEu001 incubated in HeLa cells for 6 hours. ($\lambda_{ex}$=700 nm).
Figure 5F:
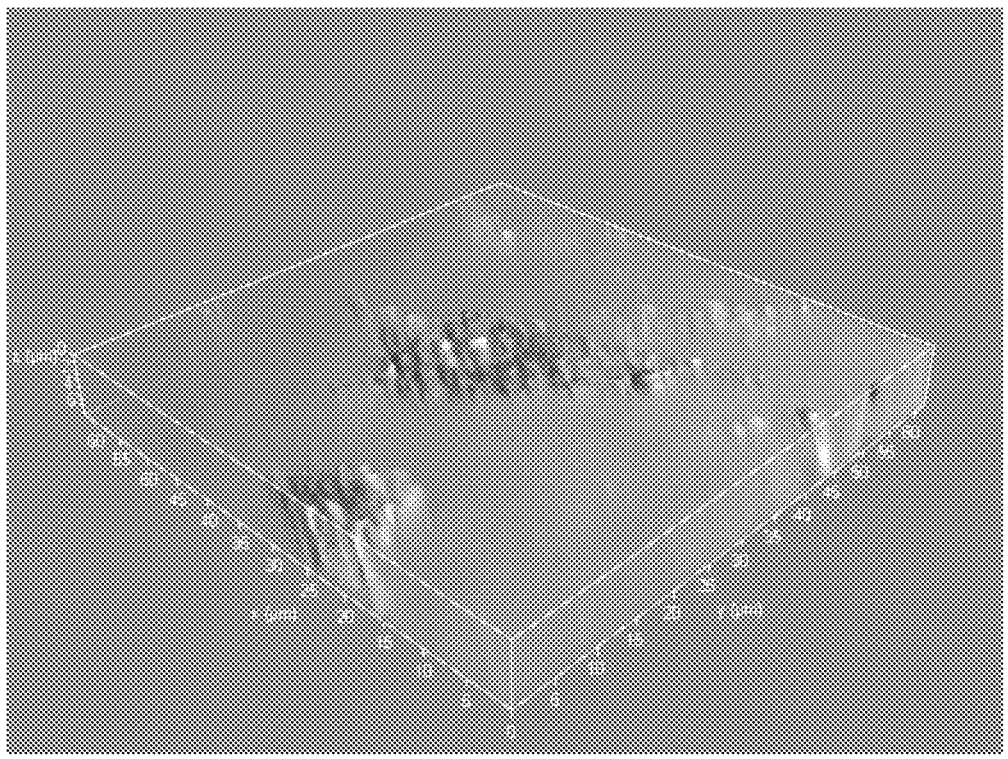
FIG. 5F shows the three dimensional in vitro imaging and emission spectra of 10 μM in xyz plane for HGEu002 incubated in HeLa cells for 6 hours. ($\lambda_{ex}$=700 nm).
Figure 6A:
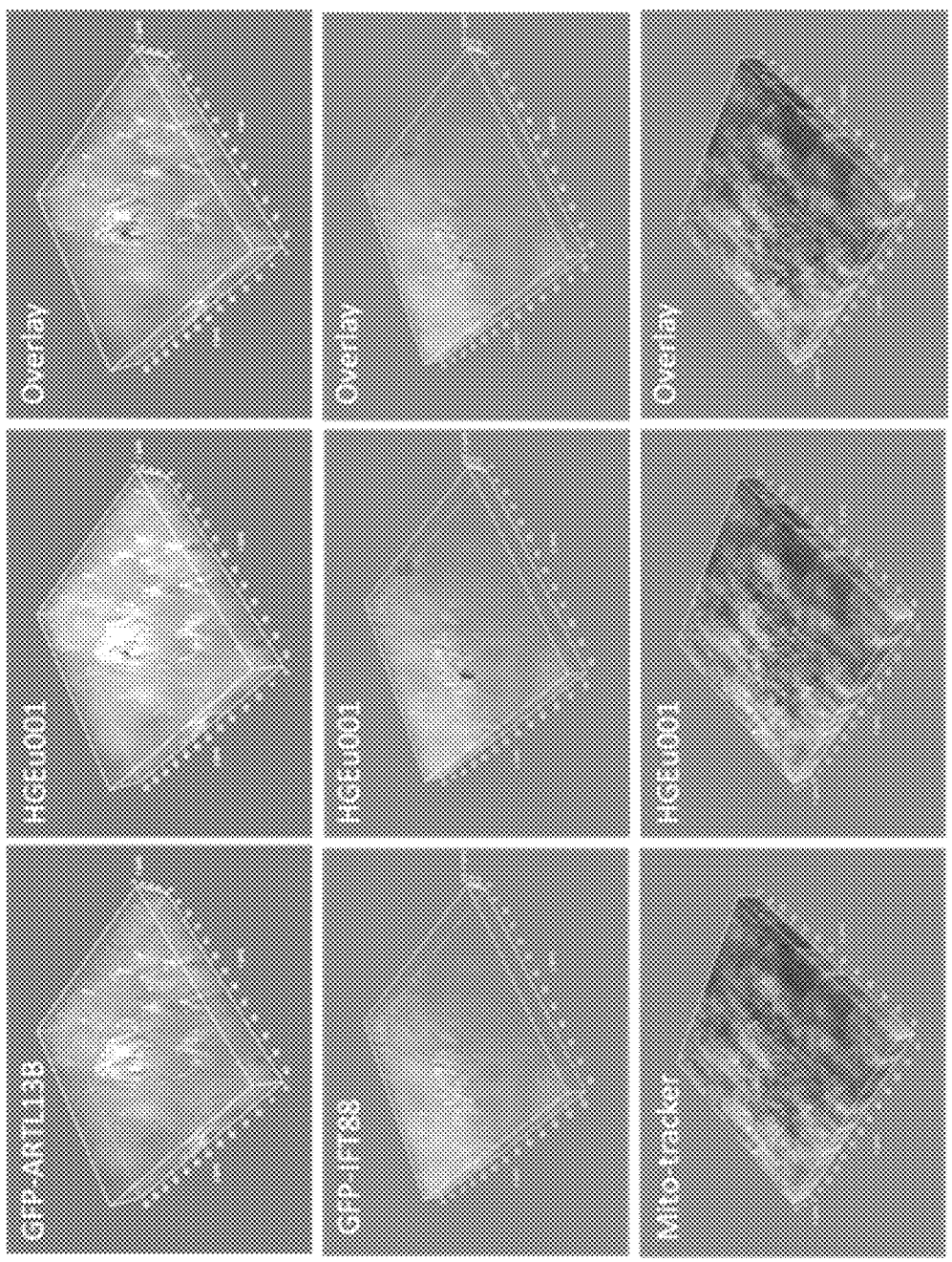
FIG. 6A shows the three dimensional (by z stack) two-photon confocal in vitro images of HGEu001 with co-localization of green GFP-ARL14B/GFP-IFT88/MitoTracker® Green FM (M-7514) in HeLa cells. ($\lambda_{ex}$=700 nm) HeLa cells were first transfected with GFP-ARL13B/GFP-IFT88 or incubated with MitoTracker® Green FM (M-7514) for 15 minutes and further incubated 6 hours with 10 μM of HGEu001.
Figure 68:
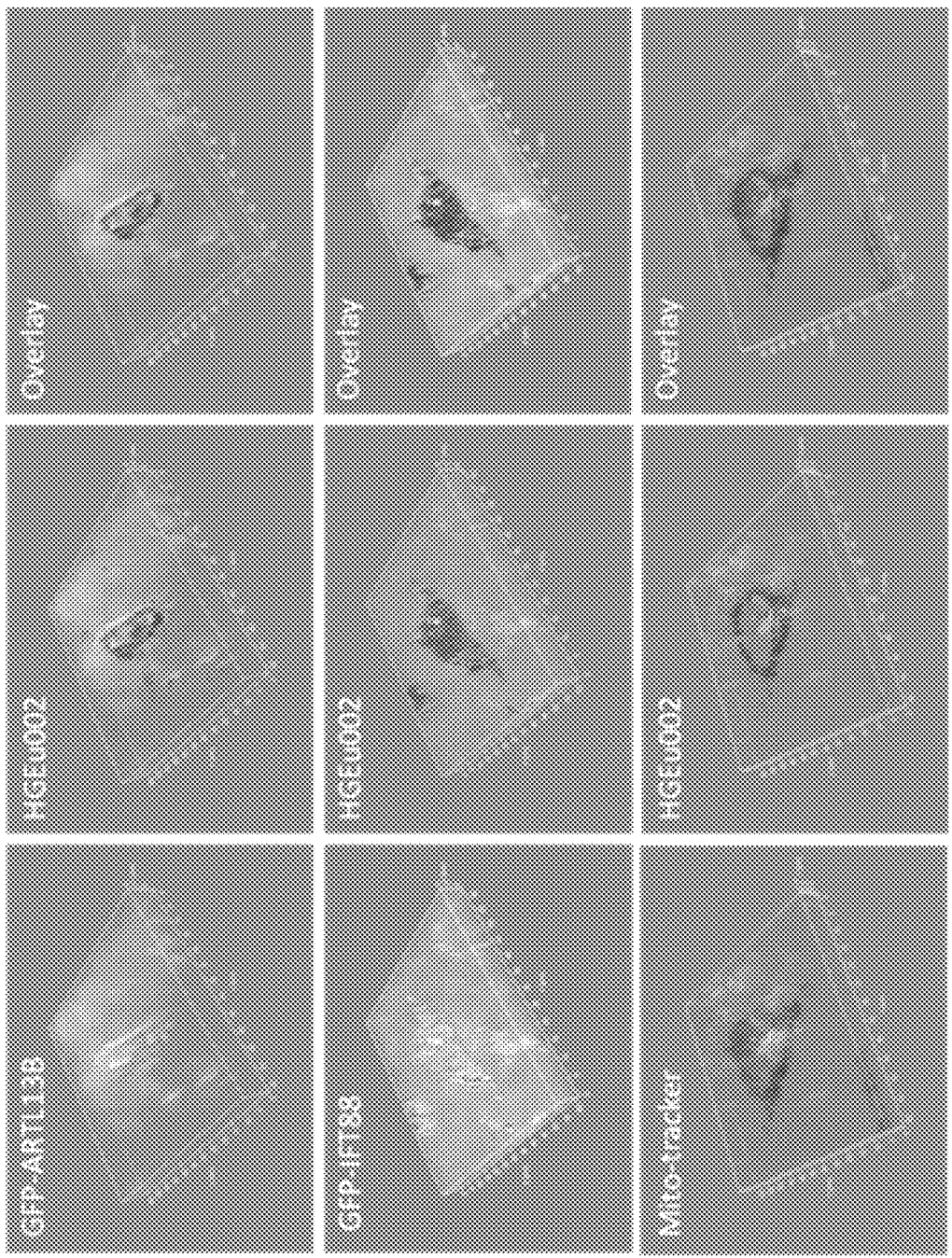
Figure 6C:
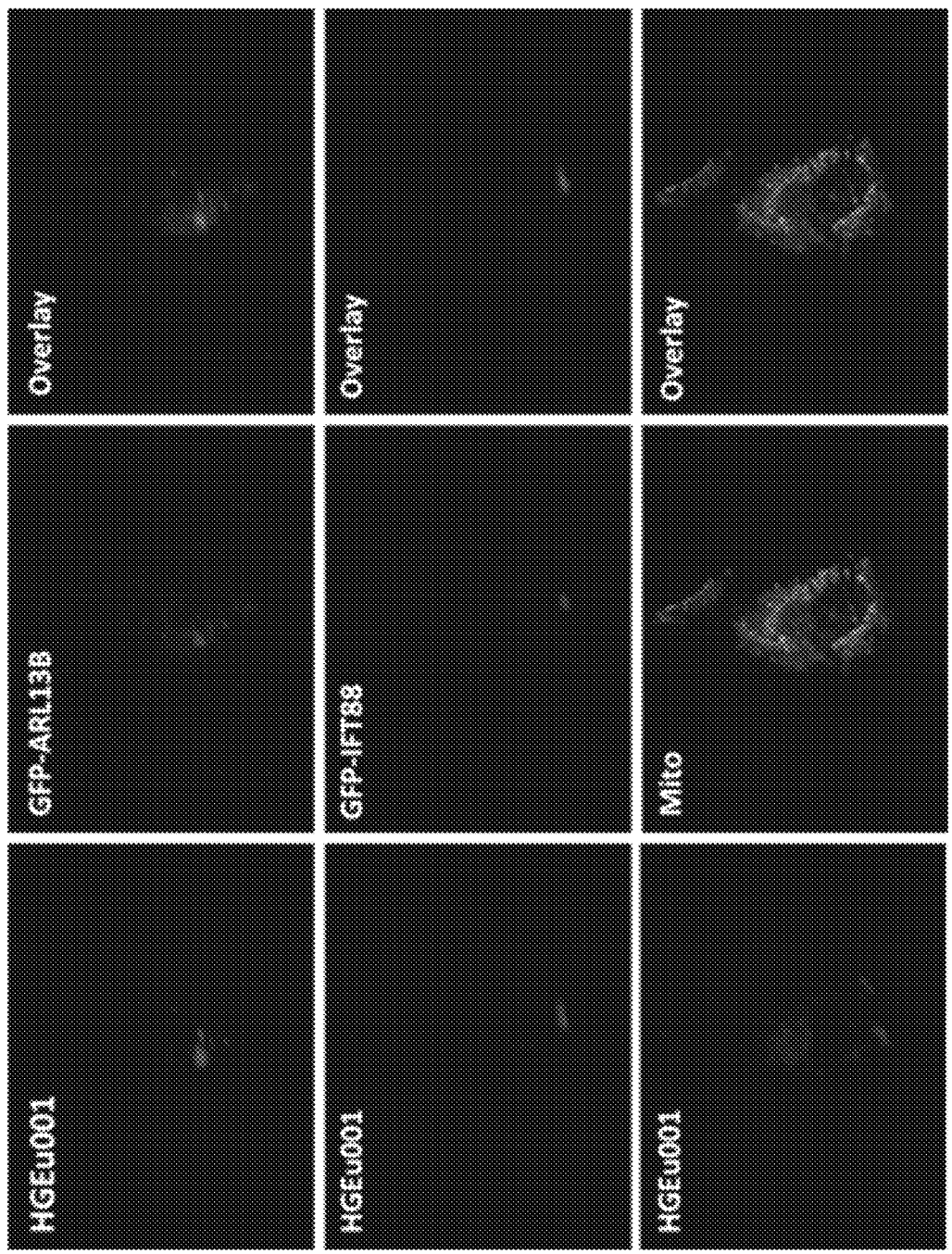
FIG. 6C shows the three dimensional (by z stack) two-photon confocal in vitro images of Dark field of HGEu001 with co-localization of green GFP-ARL14B/GFP-IFT88/MitoTracker® Green FM (M-7514) in HeLa cells. ($\lambda_{ex}$=700 nm) HeLa cells were first transfected with GFP-ARL13B/GFP-IFT88 or incubated with MitoTracker® Green FM (M-7514) for 15 minutes and further incubated 6 hours with 10 μM of HGEu001.
Figure 6D:
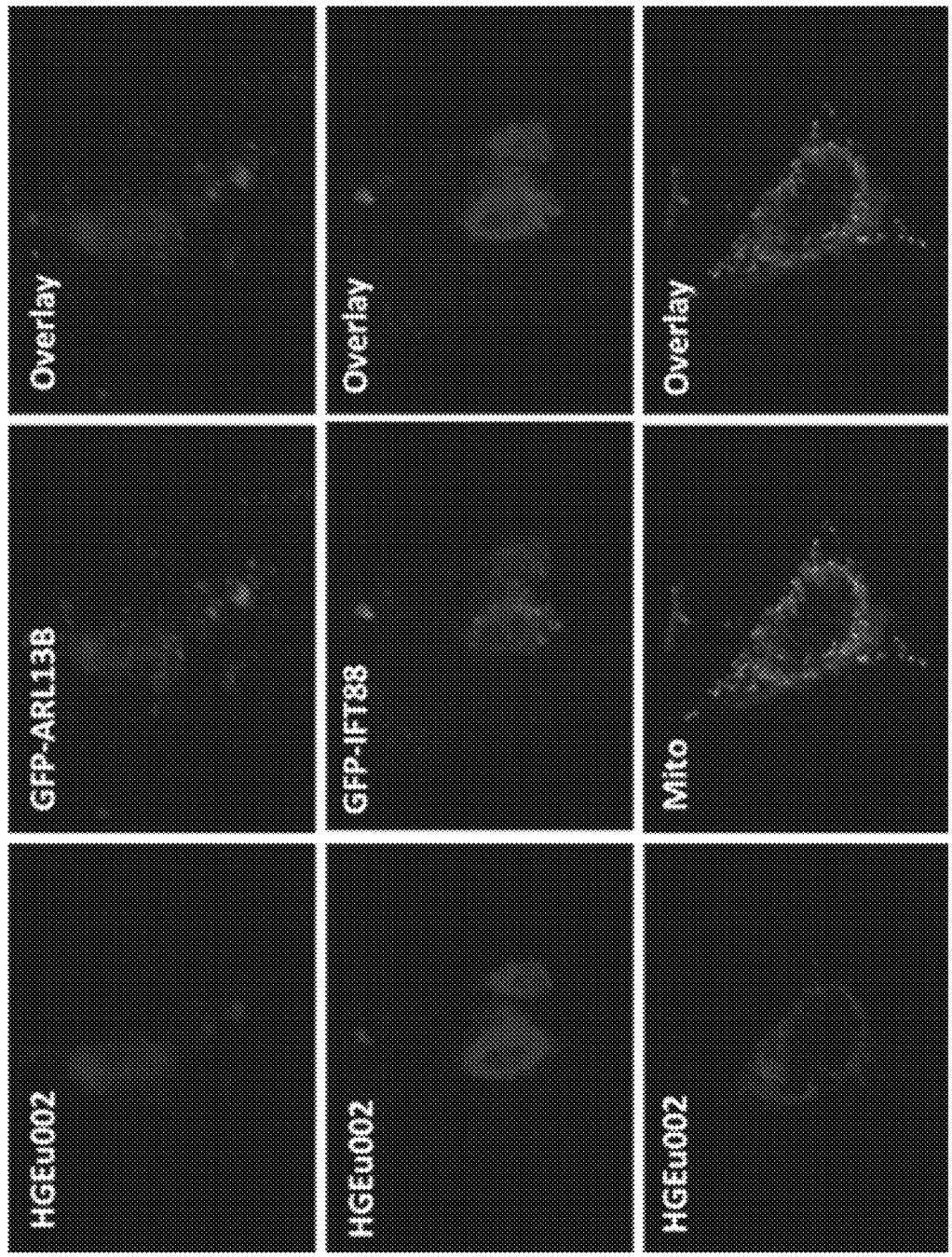
FIG. 6D shows the three dimensional (by z stack) two-photon confocal in vitro images of Dark field of HGEu002 (negative control) with co-localization of green GFP-ARL14B/GFP-IFT88/MitoTracker® Green FM (M-7514) in HeLa cells. ($\lambda_{ex}$=700 nm) HeLa cells were first transfected with GFP-ARL13B/GFP-IFT88 or incubated with MitoTracker® Green FM (M-7514) for 15 minutes and further incubated 6 hours with 10 μM of HGEu002.

The perfect overlapping of the in vitro red emission from HGEu001 (dosage concentration=10 μM, incubated for 6 hour after GFP was transfected and expressed) with the green emission from GFP-ARL13B (transfection procedure see ESI) is shown in FIGS. 4A-4H. The yellow emission of the merged images is shown as well (HGEu001, $\lambda_{ex}$ 700 nm, BP 550-665 nm, and GFP-ARL13B $\lambda_{ex}$=488 nm, BP 505-555 nm). On the other hand, the red emission of HGEu002 and green emission of GFP-ARL13B are localized in different parts in the cytoplasm and only slight yellow emission can be found in their merged images (FIG. 4G). This can confirm the selectivity of HGEu001 in primary cilia, but not HGEu002. As primary cilium is a rod-like organelle, two dimensional florescence images or confocal images are not good enough to show the specificity of the HGEu001 localization. With their two photon induced emission properties, three dimensional confocal images of HGEu001 and HGEu002 were obtained in HeLa cells by two photon confocal microscope (z stack) with excitation at 700 nm (FIGS. 5A-5H and 6A-6D). Red emission can be found in the HeLa cells and is shown as the red column (FIG. 5A). In control experiments, HGEu002 did not show any europium emission in the rod-like organelles (FIG. 5B). However, HGEu002 appears to localize in certain part of the cytoplasm instead of primary cilia.

To further confirm the selective primary cilia subcellular localization of HGEu001, three dimensional red in vitro imaging of HGEu001 and its motif control HGEu002 were compared with the primary cilia-specific green GFP-ARL13B and also with another primary cilia marker GFP-IFT88 (IFT88 is the component of IFT complex B involved in cilium biogenesis) (FIGS. 6A-6D). Only HGEu001 showed the yellow merged in vitro emission with the co-staining with GFP-ARL13B or GFP-139 IFT88. Besides, HGEu001 did not show merged yellow in vitro emission with green mito-tracker. HGEu002 also did not show merged yellow in vitro emission with neither GFP-ARL13B, GFP-IFT88 nor green mito-tracker. The 3D video of in vitro imaging in FIGS. 5A-5F and 6A-6D are shown in the supporting information.

In general, with comprehensive co-staining subcellular localization in vitro imaging studies, the selectivity of HGEu001 in primary cilia in vitro can be confirmed with good confidence. HGEu001 and HGEu002 have very similar structures, however, only HGEu001 preferentially localizes in primary cilium. Since HGEu001 did not show any non-specific staining on other organelles such as lysosome, mitochondria, or Golgi apparatus (FIGS. 2A-2I), binding to the structural components of primary cilium (e.g. cilium membrane, microtubules and associated proteins) or its associated factors, shall be a possible explanation for the specifically localization on the primary cilium of HGEu001.

The binding mechanism of the present molecules could be studied by analytical means such as proteomics mass spectrometry. Hence the present invention provides a blueprint or strategy for developing a set of primary cilia targeting probes with special functions or delivering purposes towards primary cilia by simple conjugation with the HGEu001 motif structure. In fact, the imaging protocol established in the present invention can also be used to validate the specific binding of any future probes to primary cilium, with emphasis on visualizing the rod-like structure by 3D imaging.

There is provided in the present invention a direct imaging tool for primary cilia which is specific, and can be excited by light in the near infrared (NIR) region. Comprehensive in vitro studies and several control experiments were done to confirm the specific primary cilium localization of HGEu001, showing a great degree of agreement with GFP-conjugated primary cilia markers ARL13B and IFT88 in co-localization experiments. These novel primary cilium marker could help to understand the functions and roles of primary cilium in life science, such as tumorigenesis.

Figure 28:
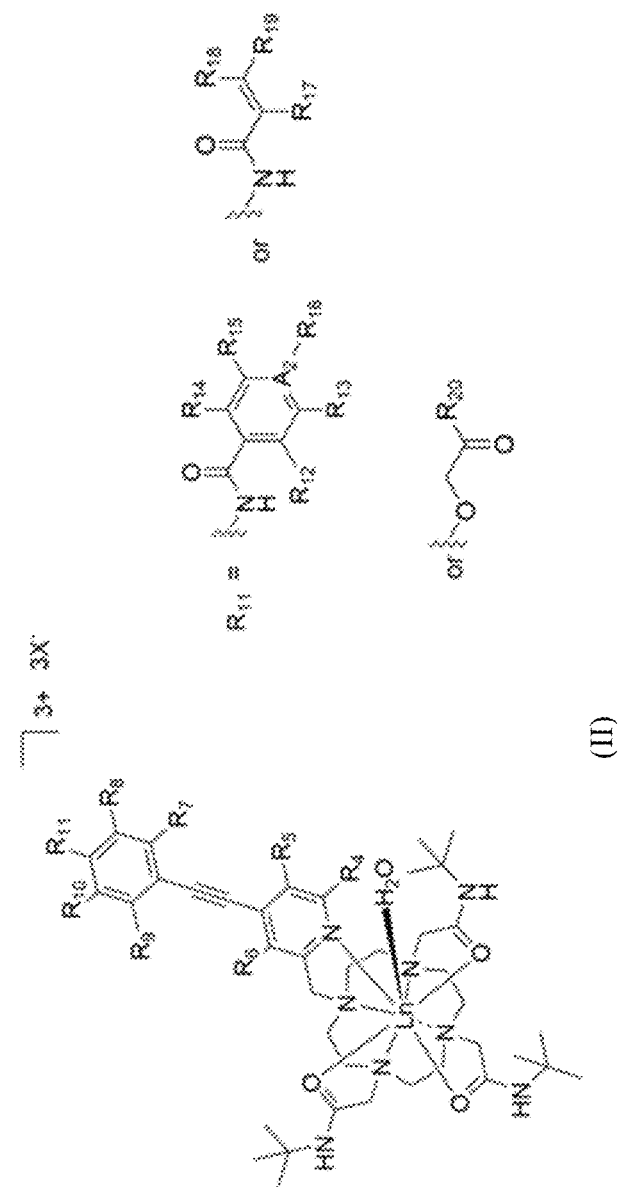
FIG. 28 shows molecular library of the europium complexes which have similar structures with HGEu001 for primary cilium specific imaging screening.

There is also provided in the present invention a possible template for designing primary cilium-specific molecules with potential modification to become target-specific drug delivery vehicles to help understand the functions of primary cilium and evolve into cancer or diseases treatment applications. A molecular library, HGEu003-HGEu016 (structures shown in FIG. 28) based on the complex HGEu001 has been developed and primary cilium imaging screening has been undertaken. Proteomic mass spectroscopy studies could also be carried out to evaluate the specific binding of HGEu001 with particular proteins in primary cilium.

INDUSTRIAL APPLICABILITY

The presently claimed invention provides a water-soluble, simple, stable tris(N-(tert-butyl)acetamide) cyclen-based europium complex HGEu001 which exhibits the specific subcellular localization in the primary cilium with a quantum yield as high as 10% in water and a lifetime of 0.56 ms lifetime. In particular, the present invention provides simplicity of the design and synthesis of a complex HGEu001. The present molecules or complexes are useful in imaging primary cilium in biological cells which serve as an organelle-specific probe for primary cilium in order to identify any disorder, disease or cancer that is associated with this particular organelle. Currently there is no such organelle-specific probe in place, which the present invention can meet this need.

What is claimed is:

1. A compound represented by formula (I):

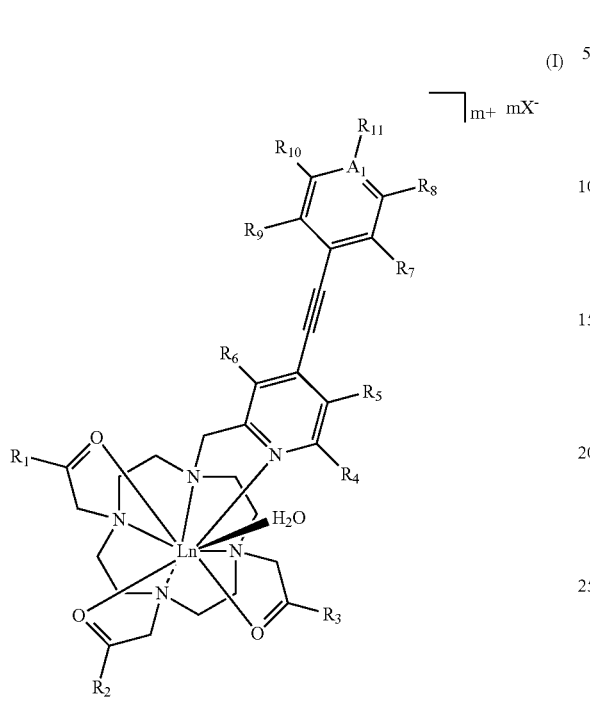

wherein Ln is selected from Eu, Tb, Gd, Yb, Er, Dy, Sm, La, Ce, Pr, Nd, Pm, Tm, and Y;

X is selected from $Cl^-$, $NO_3^-$, $CH_3COO^-$, $ClO_4^-$ or other anions;

$A_1$ is C, N, or Si;

$R_1$, $R_2$, and $R_3$ are jointly or separately selected from NHtertbutyl, or other amine;

$R_4$, $R_5$, $R_6$, $R_7$, $R_8$, $R_9$, and $R_{10}$ are jointly or separately H, $CF_3$, OMe, OEt, OH, or $NMe_2$;

$R_{11}$ is selected from alkyl, aryl ether, ester, amide or aromatic rings; and m is an integer selected from 0, 1, 2, and 3.

2. The compound according to claim 1, wherein m is 3, the molecule is represented by formula (II):

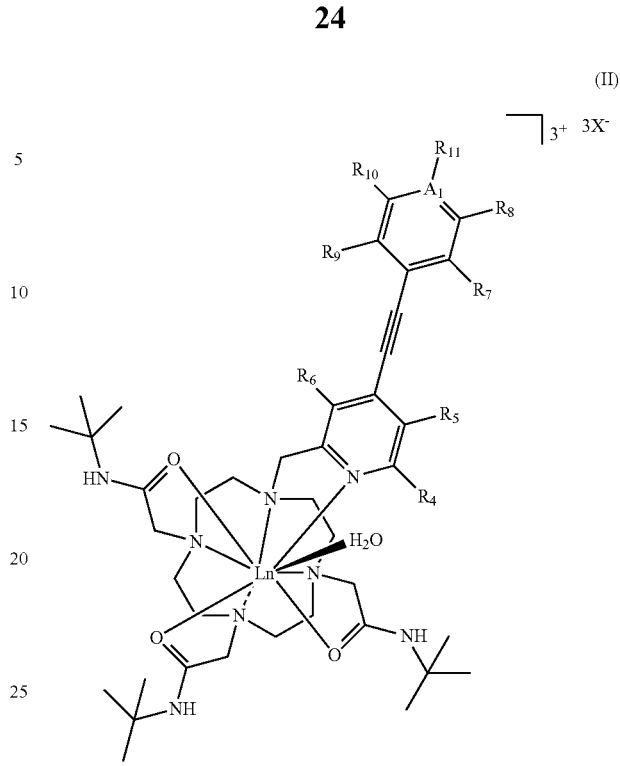

wherein $R_{11}$ is selected from:

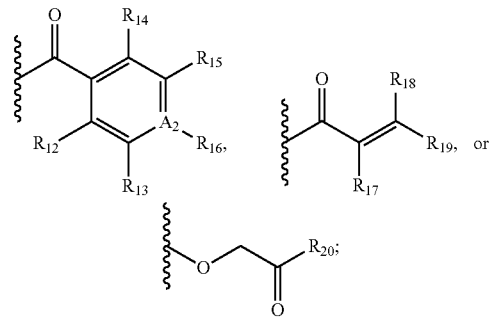

$R_{12}$, $R_{13}$, $R_{14}$, $R_{15}$, $R_{16}$, $R_{17}$, $R_{18}$, $R_{19}$, and $R_{20}$ are jointly or separately H, $CF_3$, OMe, OEt, OH, or $NMe_2$; and $A_2$ is selected from C, N or Si.

3. The compound according to claim 1, wherein the compound is selected from the group consisting of:

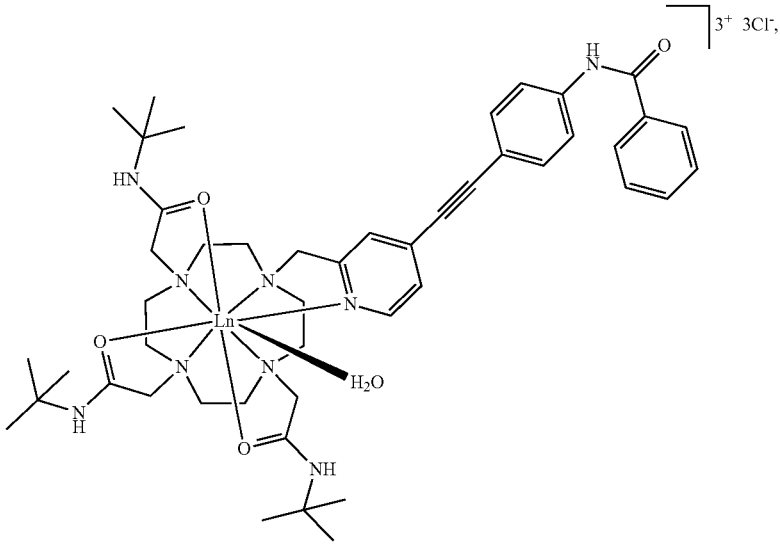

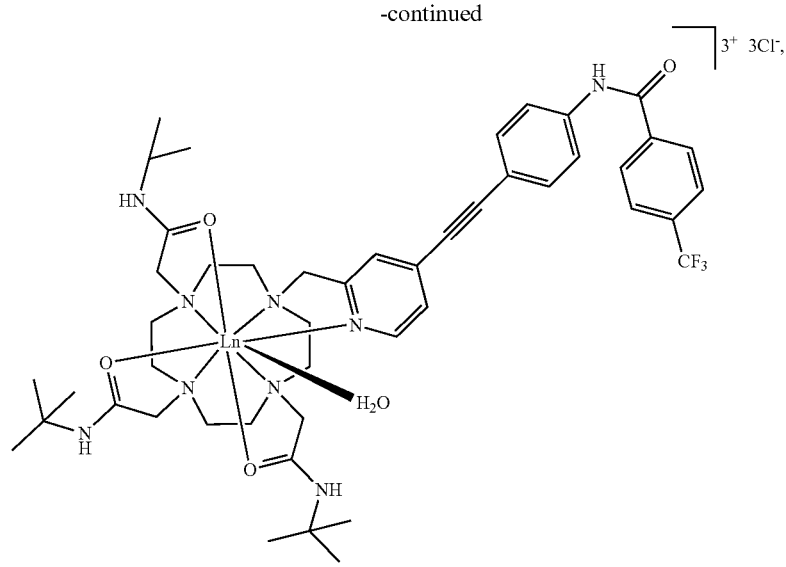
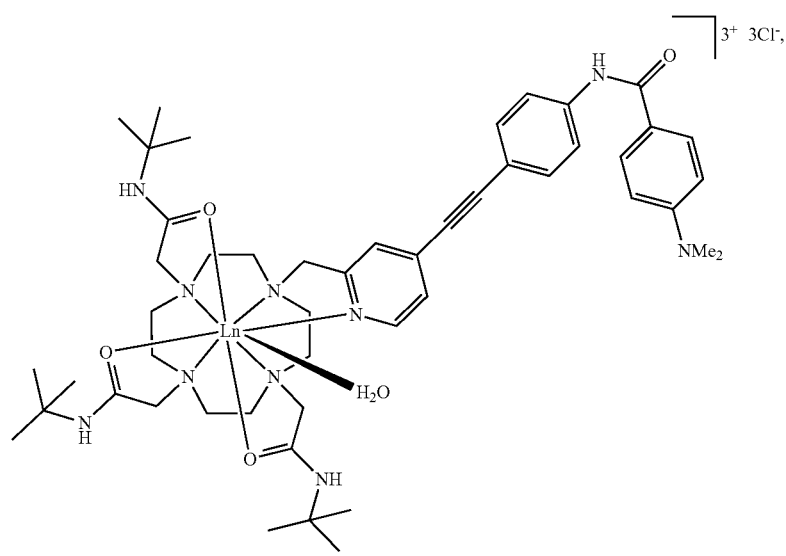
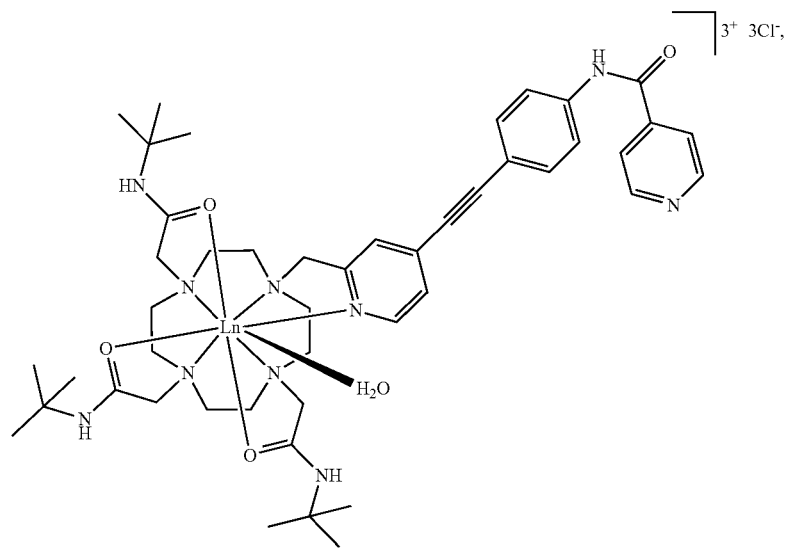

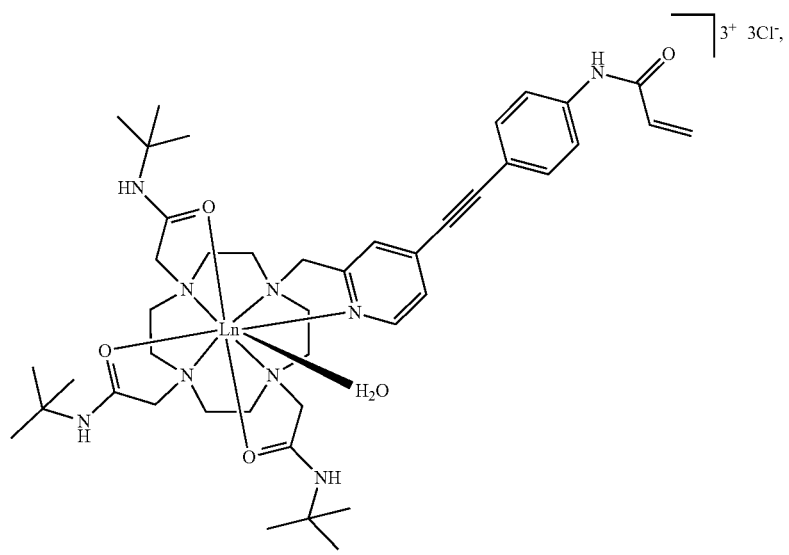
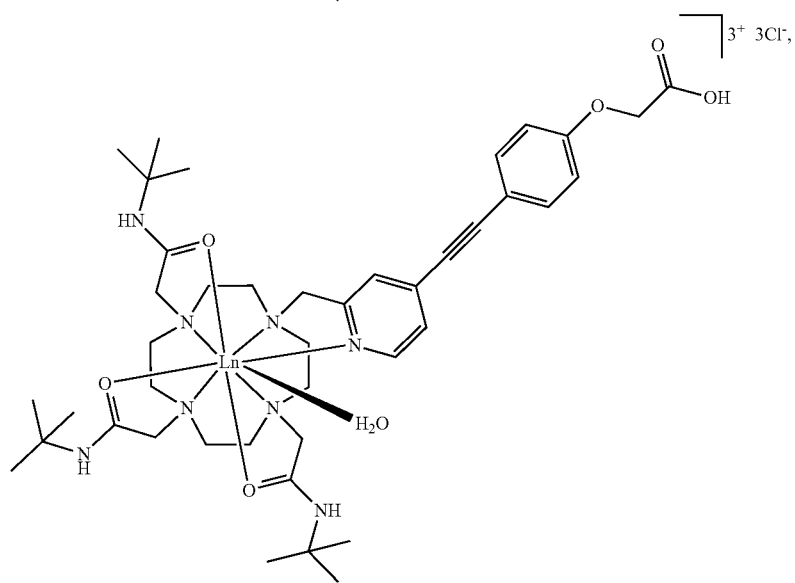
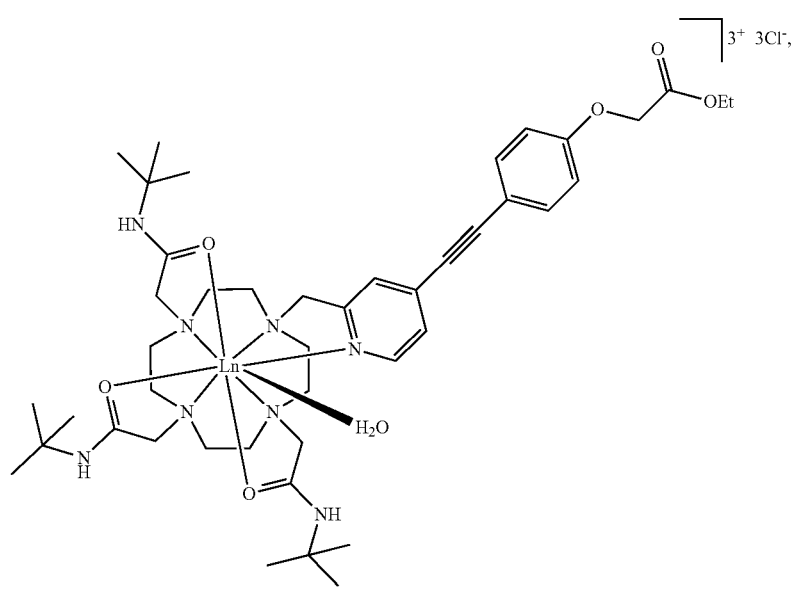

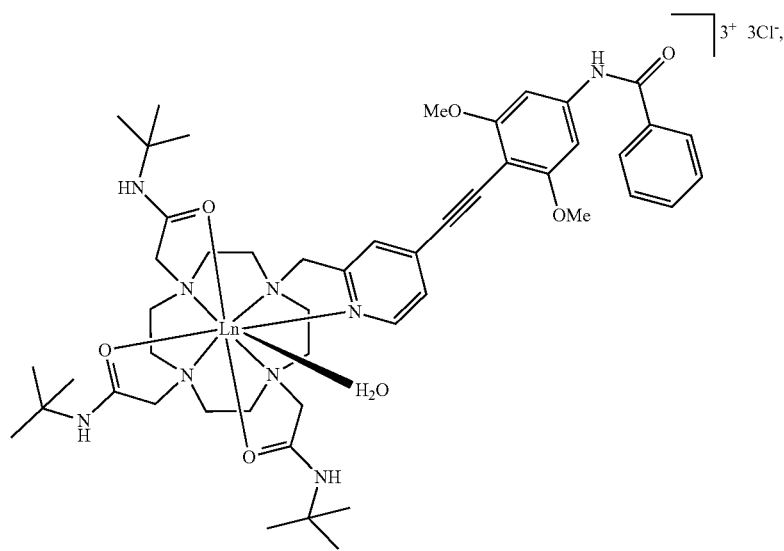
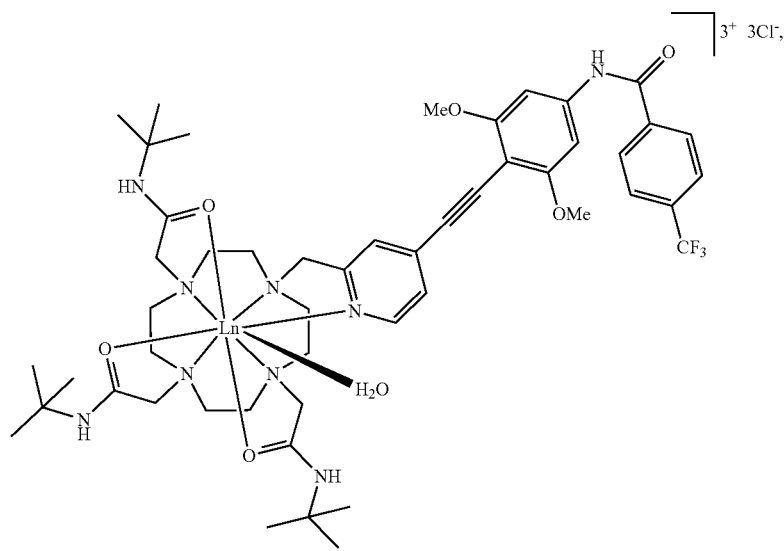
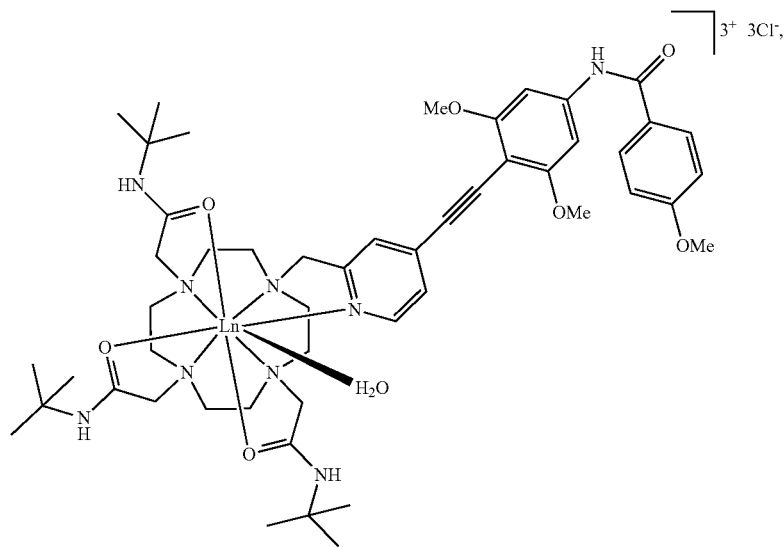

-continued
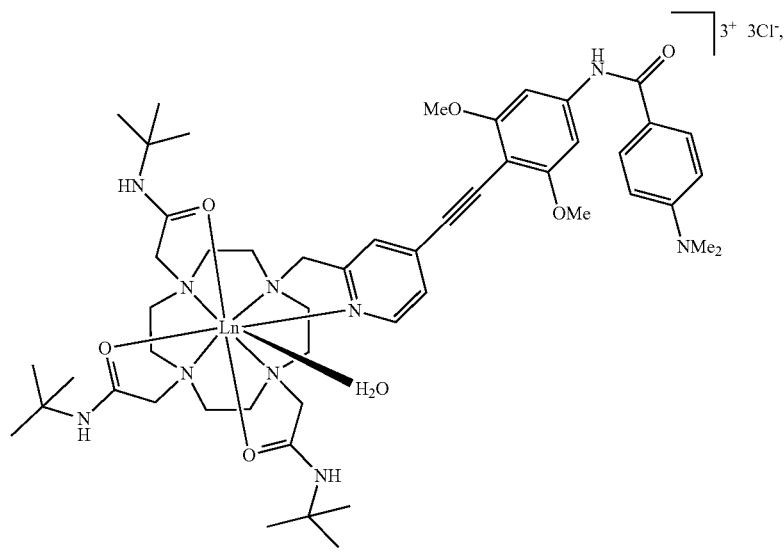
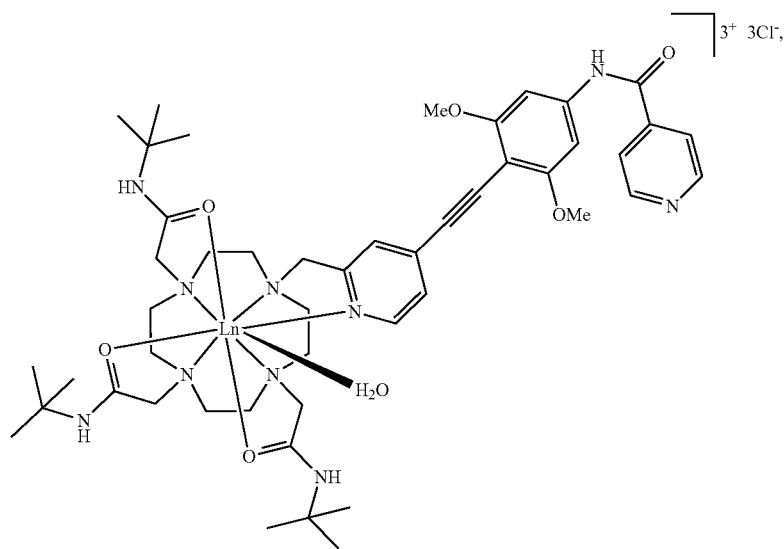
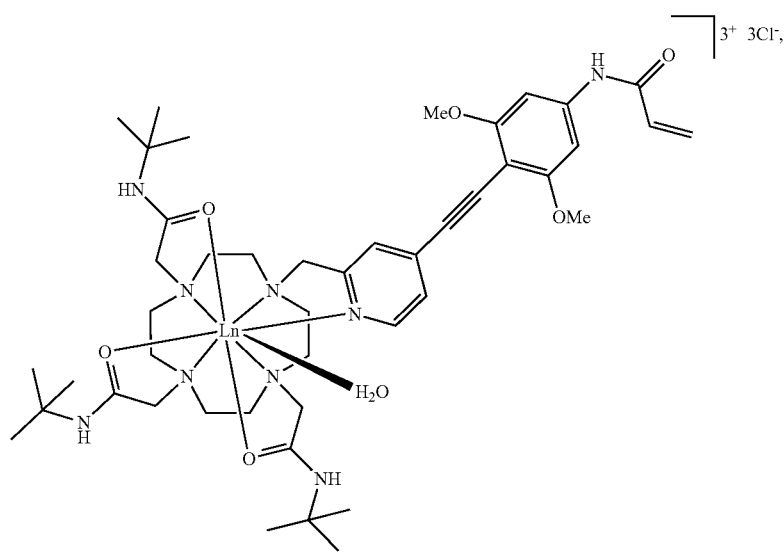

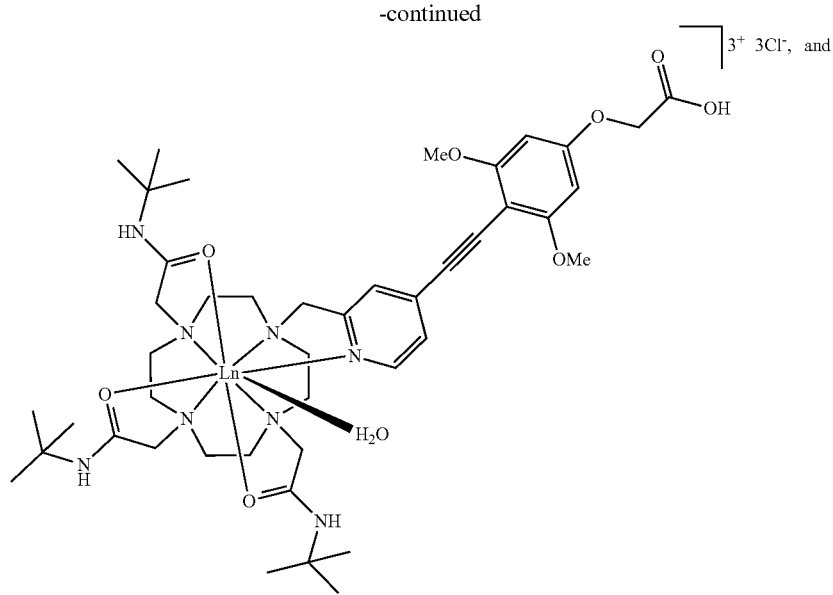

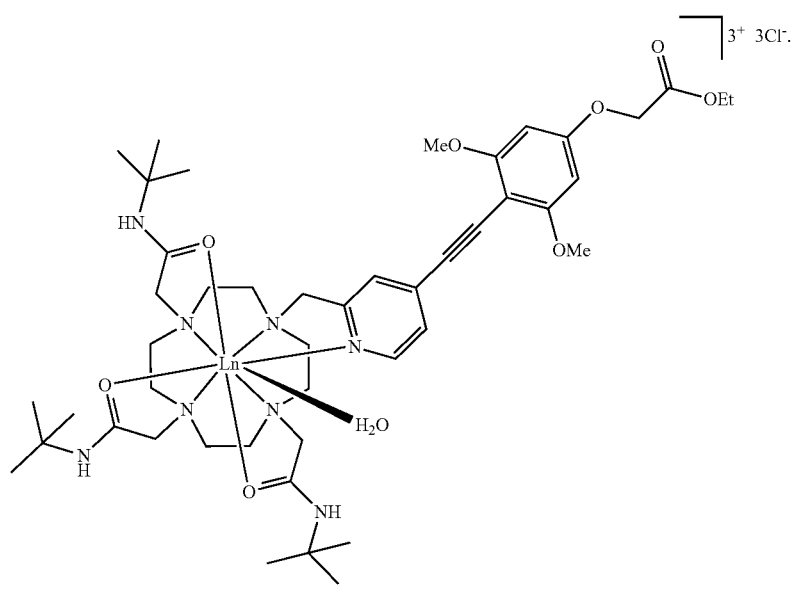

4. The compound according to claim 1, wherein said molecule selectively binds to primary cilium.

5. A method for imaging primary cilium in a biological cell comprising the steps of contacting the biological cell with the compound according to claim 1 and imaging the biological cell.

6. The method according to claim 5 wherein the imaging is performed using a linear fluorescence microscopy under UV light excitation or a two-photon confocal laser scanning microscope.

7. The method according to claim 5 wherein the imaging is done in living cells.

8. The compound of claim 1, wherein said molecule is represented by the following formula:

(III)

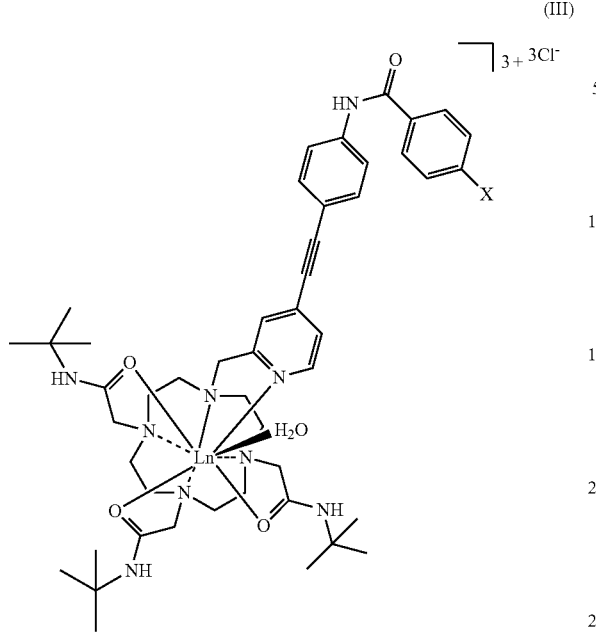

wherein X is H; Ln is Eu.

9. A method for imaging primary cilium in a biological cell comprising the steps of contacting the biological cell with the compound according to claim 8 and imaging the biological cell.

10. The method according to claim 9 wherein imaging is performed using a linear fluorescence microscopy under UV light excitation or a two-photon confocal laser scanning microscope.

11. The method according to claim 9 wherein the imaging is done in living cells.

12. A method for preparing the compound of claim 8 comprising the steps of:
contacting a compound of formula (IV)

(IV)

with EuCl$_3$ and water thereby forming the compound of claim 8.

13. The method of claim 12 further comprising the step of contacting a compound of formula (V)

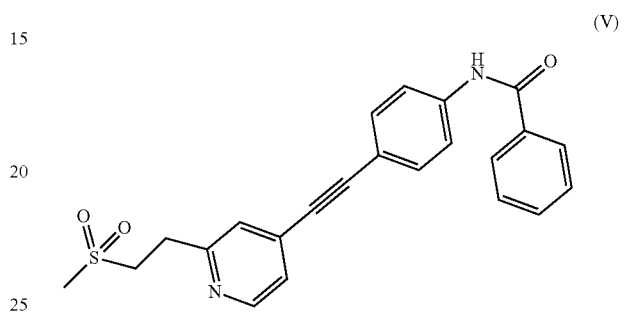

with a compound having formula (VI)

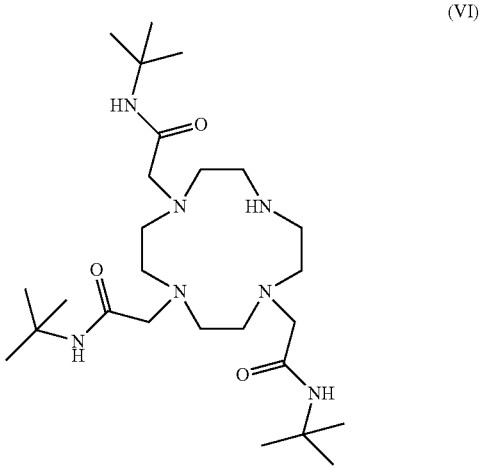 [SMILES: CC(C)(C)NC(=O)CN1CCNCCN(CC(=O)NC(C)(C)C)CCN(CC(=O)NC(C)(C)C)CC1]

thereby forming a compound of formula (IV).

* * * * *